US011441190B2

(12) United States Patent
Levine et al.

(10) Patent No.: US 11,441,190 B2
(45) Date of Patent: Sep. 13, 2022

(54) COMPOSITIONS AND METHODS FOR THE DIAGNOSIS AND TREATMENT OF OVARIAN CANCERS THAT ARE ASSOCIATED WITH REDUCED SMARCA4 GENE EXPRESSION OR PROTEIN FUNCTION

(71) Applicant: Memorial Sloan Kettering Cancer Center, New York, NY (US)

(72) Inventors: Douglas A. Levine, New York, NY (US); Michael F. Berger, New York, NY (US); Robert A Soslow, New York, NY (US); Petar Jelinic, New York, NY (US)

(73) Assignee: MEMORIAL SLOAN KETTERING CANCER CENTER, New York, NY (US)

( * ) Notice: Subject to any disclaimer, the term of this patent is extended or adjusted under 35 U.S.C. 154(b) by 0 days.

(21) Appl. No.: 16/237,692

(22) Filed: Jan. 1, 2019

(65) Prior Publication Data

US 2019/0309371 A1 Oct. 10, 2019

Related U.S. Application Data

(63) Continuation of application No. 15/109,403, filed as application No. PCT/US2014/073077 on Dec. 31, 2014, now abandoned.

(60) Provisional application No. 61/973,759, filed on Apr. 1, 2014, provisional application No. 61/922,710, filed on Dec. 31, 2013.

(51) Int. Cl.
*C12Q 1/6886* (2018.01)
*A61K 31/7088* (2006.01)

(52) U.S. Cl.
CPC ........ *C12Q 1/6886* (2013.01); *A61K 31/7088* (2013.01); *C12Q 2600/106* (2013.01); *C12Q 2600/118* (2013.01); *C12Q 2600/136* (2013.01); *C12Q 2600/156* (2013.01); *C12Q 2600/158* (2013.01)

(58) Field of Classification Search
CPC ............ C12Q 1/6886; C12Q 2600/106; C12Q 2600/118; C12Q 2600/156
See application file for complete search history.

(56) References Cited

U.S. PATENT DOCUMENTS

| 6,465,629 B1 | 10/2002 | Wong et al. | |
| 9,895,390 B2 * | 2/2018 | Fillmore | A61P 35/00 |
| 2015/0320779 A1 * | 11/2015 | Fillmore | A61K 31/7048 514/27 |

FOREIGN PATENT DOCUMENTS

WO   WO-2014092905 A1 *   6/2014   ......... A61K 31/7048

OTHER PUBLICATIONS

Kupryjanczyk et al. Pol J Pathol. 2013. 64(4):238-246. (Year: 2013).*
Lu et al. Journal of Cancer. 2019. 10(1):223-237. (Year: 2019).*
Fernando et al. Nature Communications. 2020. 11:5551. (Year: 2020).*
Emmanuel et al. Comparison of expression profiles in ovarian cancer identifies novel candidate genes involved in disease pathogenesis. PloS One, vol. 6. Issue No. 3. Article No. e17617 (internal pp. 1-18)2011.
International Search Report and Written Opinion, PCT/US2014/073077, Memorial Sloan Kettering Cancer Center, 13 pages (dated Mar. 18, 2015).
Medina et al. Frequent BRG1/SMARCA4 inactivating mutations in human lung cancer cell lines. Human Mutation. vol. 29. No. 5. pp. 617-622 (2008) See abstract: pp. 618-620; and figure 1.
Oike et al. A synthetic lethality based strategy to treat cancers harboring a genetic deficiency in the chromatin remodeling factor BRG1. Cancer Research. vol. 73. No. 17. pp. 5508-5518 Sep. 2013 See whole document.
Serber at al. The BRGI chromate in remodeler protects against ovarian cysts, uterine tumor, and mammary tumors in a lineage specific manner. PloS One. vol. 7 Issue No. 2. Article No. e31346 (internal pp. 1-10) (2012) See whole document.
Shain et al. Convergent structural alterations define Switch/Sucrose NonFermentable (SWI/SNF) chromatin remodeler as a central tumor suppressive complex in pancreatic cancer. PNAS. vol. 109. No. 5. pp. E252-E259 (2012) See abstract: pp. E254 E258 figure 4 and table 1.
Witowski et al. Germiline and somatic SMARCA4 mutations characterize small cell carcinoma of the ovary, hypercalcemic type. Nature Genetics. vol. 46. No. 5. pp. 438-443 (May 2014) See the whole document.
Wong et al. Cancer Research. 2000. 60:6171-6177.

* cited by examiner

*Primary Examiner* — Joseph G. Dauner
(74) *Attorney, Agent, or Firm* — Foley & Lardner LLP

(57) ABSTRACT

Provided are compositions and methods for the identification and treatment of ovarian cancers, such as small cell ovarian cancers, in particular small cell carcinoma of the ovary, hypercalcemic type (SCCOHT), which ovarian cancers are characterized by reduced SMARCA4 gene expression and/or protein function and, as a consequence, are sensitive to growth and/or survival inhibition by one or more compounds that restore SMARCA4 gene expression and/or protein function.

3 Claims, 18 Drawing Sheets

Specification includes a Sequence Listing.

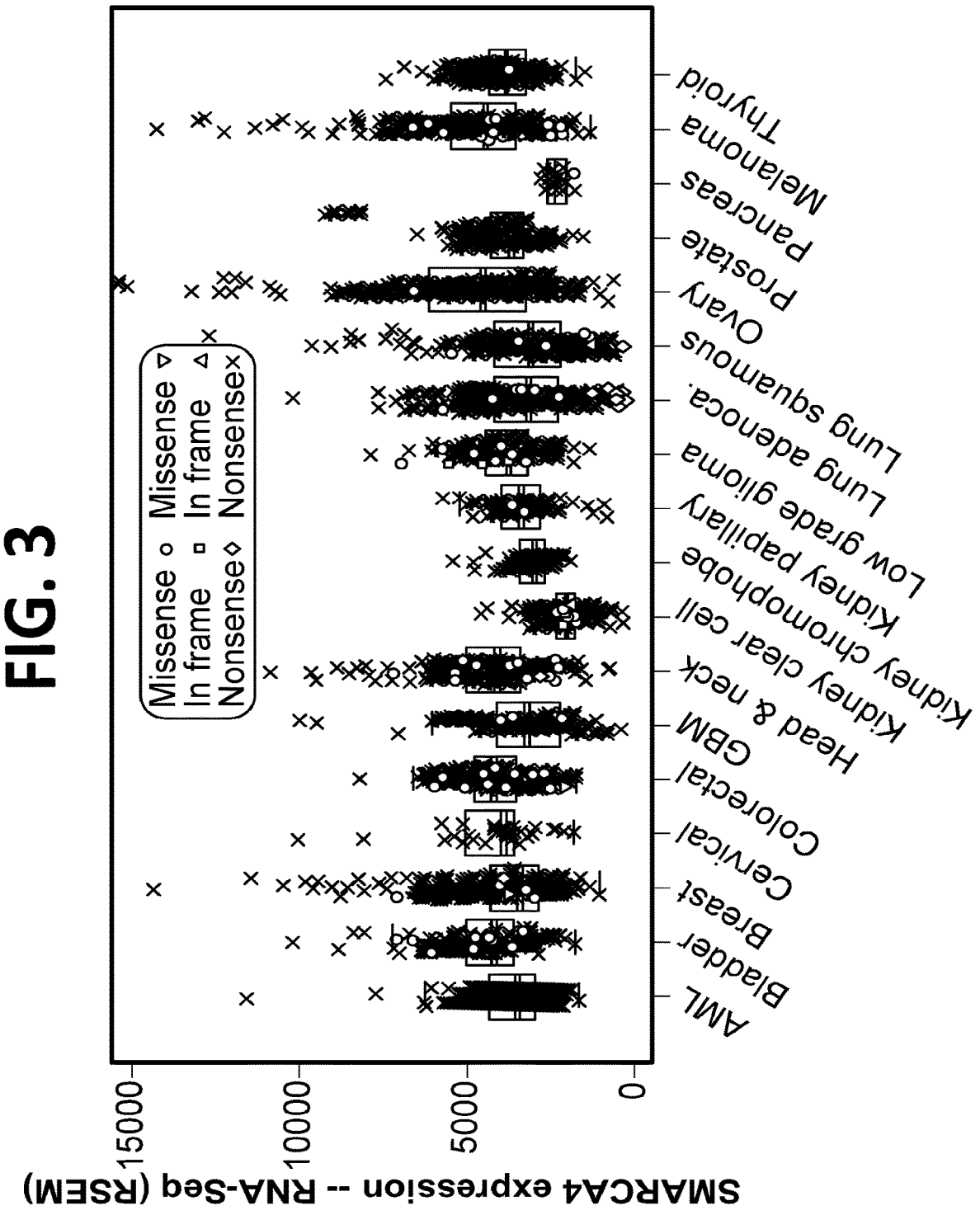

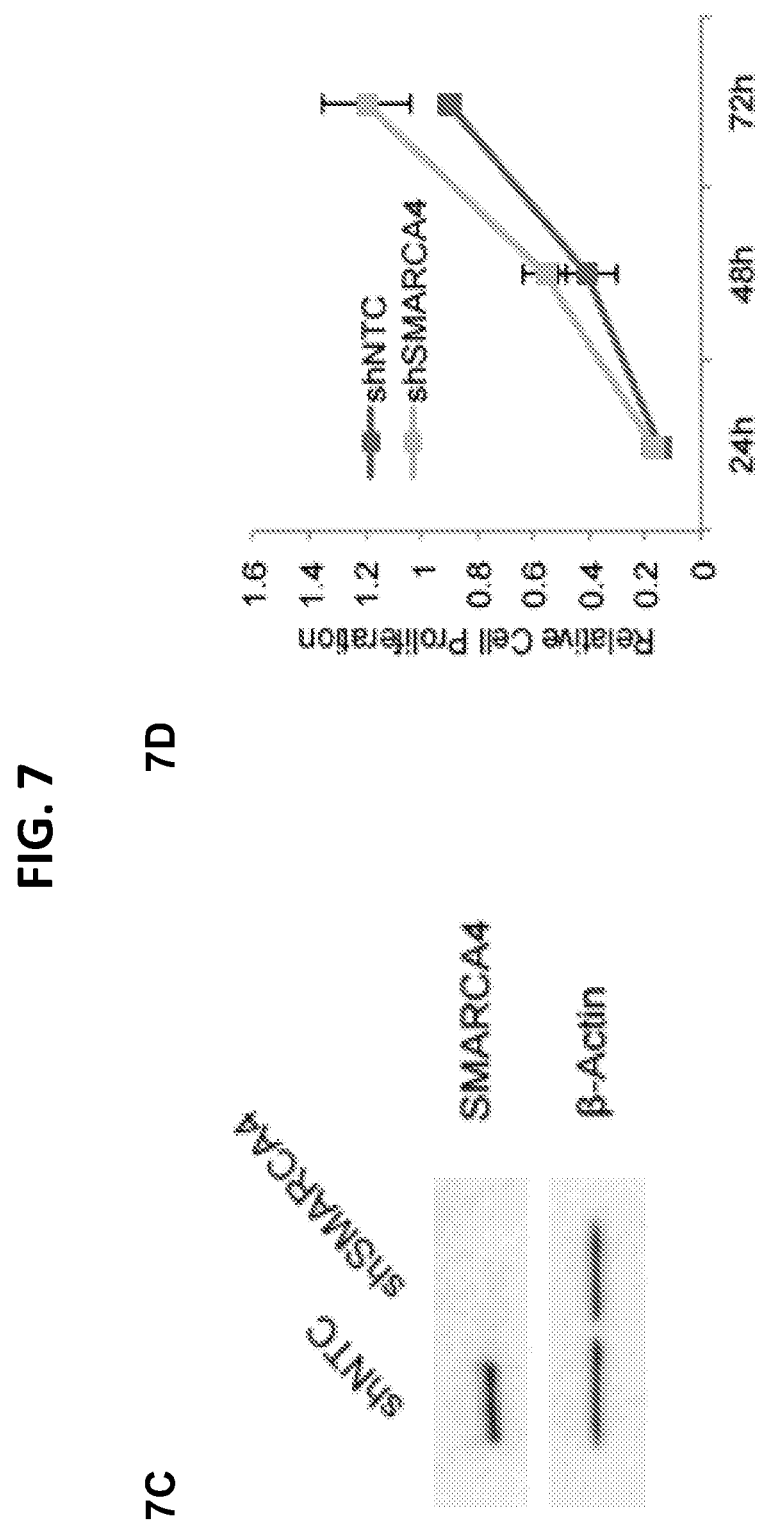

FIG. 12
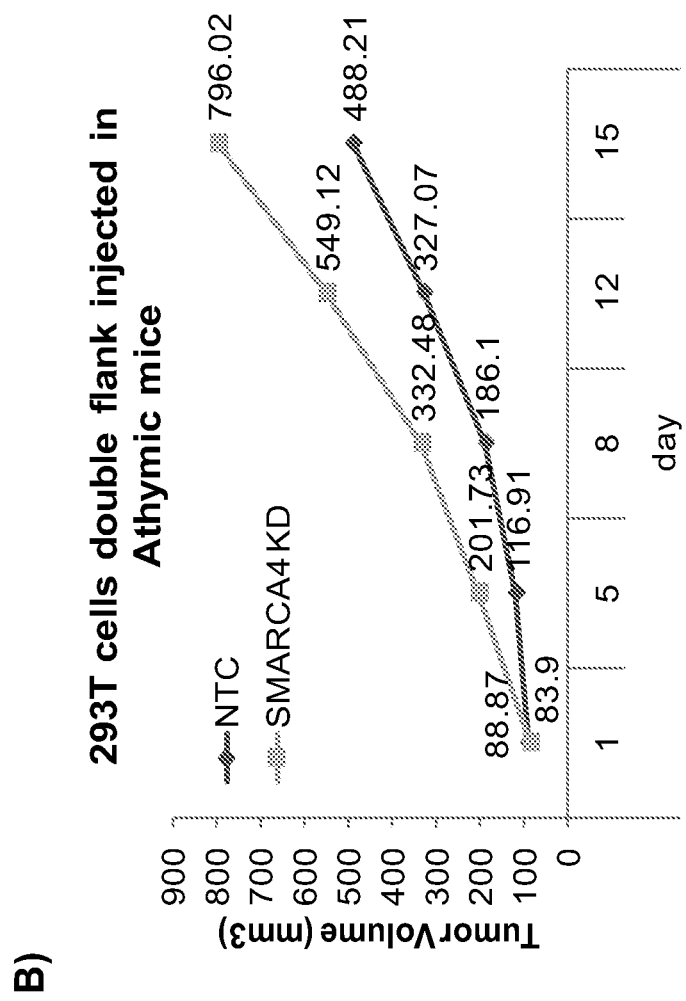
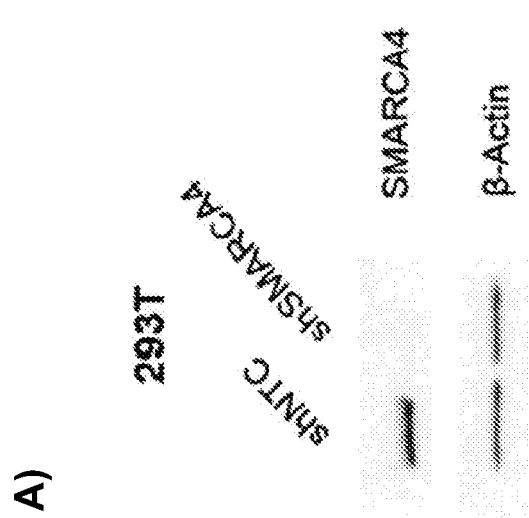

SEQUENCE LISTING

```
<160> NUMBER OF SEQ ID NOS: 17

<210> SEQ ID NO 1
<211> LENGTH: 4845
<212> TYPE: DNA
<213> ORGANISM: Homo sapiens
<220> FEATURE:
<223> OTHER INFORMATION: Homo sapiens SMARCA4 isoform 1 mRNA

<400> SEQUENCE: 1
atgtccactc cagacccacc cctgggcgga actcctcggc caggtccttc cccgggccct      60
ggcccttccc ctggagccat gctgggccct agcccgggtc cctcgccggg ctccgcccac     120
agcatgatgg ggcccagccc agggccgccc tcagcaggac accccatccc cacccagggg     180
cctggagggt acccctcagga caacatgcac cagatgcaca agcccatgga gtccatgcat     240
gagaagggca tgtcggacga cccgcgctac aaccagatga aggaatggg gatgcggtca      300 gggggccatg ctgggatggg gccccgccc agccccatgg accagcactc ccaaggttac      360
ccctcgcccc tgggtggctc tgagcatgcc tctagtccaa ttccagccag tggcccgtct      420
tcggggcccc agatgtcttc cgggccagga ggtgccccgc tggatggtgc tgaccccag      480 gccttgggc agcagaaccg ggcccaacc ccatttaacc agaaccagct gcaccagctc      540
agagctcaga tcatggccta caagatgctg gccagggggc agcccctccc cgaccacctg      600
cagatggcgg tgcagggcaa gcggccgatg cccgggatgc agcagcagat gccaacgcta      660
cctccaccct cggtgtccgc aacaggaccc ggccctggcc ctggccctgg ccccggcccg      720
ggtcccggcc cggcacctcc aaattacagc aggcctcatg gtatgggagg gcccaacatg      780 cctccccag gaccctcggg cgtgccccc gggatgccag gcagcctcc tggagggcct      840 cccaagccct ggcctgaagg accccatggcg aatgctgctg ccccacgag caccctcag      900 aagctgattc ccccgcagcc aacgggccgc ccttccccg cgccctgc cgtcccaccc      960
```

```
gccgcctcgc ccgtgatgcc accgcagacc cagtcccccg ggcagccggc ccagcccgcg      1020
cccatggtgc cactgcacca gaagcagagc cgcatcaccc ccatccagaa gccgcggggc      1080
ctcgaccctg tggagatcct gcaggagcgc gagtacaggc tgcaggctcg catcgcacac      1140
cgaattcagg aacttgaaaa ccttcccggg tccctggccg gggatttgcg aaccaaagcg      1200
accattgagc tcaaggccct caggctgctg aacttccaga ggcagctgcg ccaggaggtg      1260
gtggtgtgca tgcggaggga cacagcgctg agacagccc tcaatgctaa ggcctacaag      1320
cgcagcaagc gccagtccct gcgcgaggcc cgcatcactg agaagctgga gaagcagcag      1380
aagatcgagc aggagcgcaa gcgccggcag aagcaccagg aatacctcaa tagcattctc      1440
cagcatgcca aggatttcaa ggaatatcac agatccgtca caggcaaaat ccagaagctg      1500
accaaggcag tggccacgta ccatgccaac acggagcggg agcagaagaa agagaacgag      1560
cggatcgaga aggagcgcat gcggaggctc atggctgaag atgaggaggg gtaccgcaag      1620
ctcatcgacc agaagaagga caagcgcctg gcctacctct tgcagcagac agacgagtac      1680
gtggctaacc tcacggagct ggtgcggcag cacaaggctg cccaggtcgc caaggagaaa      1740
aagaagaaaa agaaaaagaa gaaggcagaa aatgcagaag acagacgcc tgccattggg      1800 ccggatggcg agcctctgga cgagaccagc cagatgagcg acctcccggt gaaggtgatc      1860
cacgtggaga gtgggaagat cctcacaggc acagatgccc ccaaagccgg gcagctggag      1920
gcctggctcg agatgaaccc ggggtatgaa gtagctccga ggtctgatag tgaagaaagt      1980
ggctcagaag aagaggaaga ggaggaggag gaagagcagc cgcaggcagc acagcctccc      2040
accctgcccg tggaggagaa gaagaagatt ccagatccag acagcgatga cgtctctgag      2100
gtggacgcgc ggcacatcat tgagaatgcc aagcaagatg tcgatgatga atatggcgtg      2160
tcccaggccc ttgcacgtgg cctgcagtcc tactatgccg tggcccatgc tgtcactgag      2220
agagtggaca agcagtcagc gcttatggtc aatggtgtcc tcaaacagta ccagatcaaa      2280
ggtttggagt ggctggtgtc cctgtacaac aacaacctga acggcatcct ggccgacgag      2340
atgggcctgg ggaagaccat ccagaccatc gcgctcatca cgtacctcat ggagcacaaa      2400
cgcatcaatg gcccttcct catcatcgtg cctctctcaa cgctgtccaa ctgggcgtac      2460
gagtttgaca gtgggcccc ctccgtggtg aaggtgtctt acaagggatc cccagcagca      2520
agacgggcct ttgtccccca gctccggagt gggaagttca cgtcttgct gacgacgtac      2580 gagtacatca tcaaagacaa gcacatcctc gccaagatcc gttggaagta catgattgtg      2640
gacgaaggtc accgcatgaa gaaccaccac tgcaagctga cgcaggtgct caacacgcac      2700
tatgtggcac cccgccgcct gctgctgacg ggcacaccgc tgcagaacaa gcttcccgag      2760
ctctgggcgc tgctcaactt cctgctgccc accatcttca agagctgcag caccttcgag      2820
cagtggttta acgcacccit tgccatgacc ggggaaaagg tggacctgaa tgaggaggaa      2880
accattctca tcatccggcg tctccacaaa gtgctgcggc ccttcttgct ccgacgactc      2940
aagaaggaag tcgaggccca gttgcccgaa aaggtggagt acgtcatcaa gtgcgacatg      3000
tctgcgctgc agcgagtgct ctaccgccac atgcaggcca agggcgtgct gctgactgat      3060
ggctccgaga aggacaagaa gggcaaaggc ggcaccaaga ccctgatgaa caccatcatg      3120
cagctgcgga agatctgcaa ccaccccctac atgttccagc acatcgagga gtccttttcc      3180
gagcacttgg ggttcactgg cggcattgtc caagggctgg acctgtaccg agcctcgggt      3240
aaatttgagc ttcttgatag aattcttccc aaactccgag caaccaacca caagtgctgc      3300
ctgttctgcc aaatgaccct cctcatgacc atcatggaag attactttgc gtatcgcggc      3360
```

```
tttaaatacc tcaggcttga tggaaccacg aaggcggagg accggggcat gctgctgaaa    3420
accttcaacg agcccggctc tgagtacttc atcttcctgc tcagcacccg ggctgggggg    3480
ctcggcctga acctccagtc ggcagacact gtgatcattt ttgacagcga ctggaatcct    3540
caccaggacc tgcaagcgca ggaccgagcc caccgcatcg ggcagcagaa cgaggtgcgt    3600
gtgctccgcc tctgcaccgt caacagcgtg gaggagaaga tcctagctgc agccaagtac    3660
aagctcaacg tggaccagaa ggtgatccag gccggcatgt tcgaccagaa gtcctccagc    3720
catgagcggc gcgccttcct gcaggccatc ctggagcacg aggagcagga tgaggaggaa    3780
gacgaggtgc ccgacgacga gaccgtcaac cagatgatcg cccggcacga ggaggagttt    3840
gatctgttca tgcgcatgga cctggaccgc aggcgcgagg aggcccgcaa ccccaagcgg    3900
aagccgcgcc tcatggagga ggacgagctc ccctcgtgga tcatcaagga cgacgcggag    3960
gtggagcggc tgacctgtga ggaggaggag agaagatgt tcggccgtgg ctcccgccac    4020
cgcaaggagg tggactacag cgactcactg acggagaagc agtggctcaa ggccatcgag    4080
gagggcacgc tggaggagat cgaagaggag gtccggcaga agaaatcatc acggaagcgc    4140
aagcgagaca gcgacgccgg ctcctccacc ccgaccacca gcaccgcag ccgcgacaag    4200
gacgacgaga gcaagaagca gaagaagcgc gggcggccgc tgccgagaa actctccct     4260
aacccaccca acctcaccaa gaagatgaag aagattgtgg atgccgtgat caagtacaag    4320
gacagcagca gtgacgtca gctcagcgag gtcttcatcc agctgccctc gcgaaaggag    4380
ctgcccgagt actacgagct catccgcaag cccgtggact tcaagaagat aaaggagcgc    4440
attcgcaacc acaagtaccg cagcctcaac gacctagaga aggacgtcat gctcctgtgc    4500
cagaacgcac agaccttcaa cctggagggc tccctgatct atgaagactc catcgtcttg    4560
cagtcggtct tcaccagcgt gcggcagaaa atcgagaagg aggatgacag tgaaggcgag    4620
gagagtgagg aggaggaaga gggcgaggag gaaggctccg aatccgaatc tcggtccgtc    4680
aaagtgaaga tcaagcttgg ccggaaggag aaggcacagg accggctgaa gggcggccgg    4740
cggcggccga gccagggtc ccgagccaag ccggtcgtga gtgacgatga cagtgaggag    4800
gaacaagagg aggaccgctc aggaagtggc agcgaagaag actga                   4845
```

<210> SEQ ID NO 2
<211> LENGTH: 1614
<212> TYPE: PRT
<213> ORGANISM: Homo sapiens
<220> FEATURE:
<223> OTHER INFORMATION: Homo sapiens SMARCA4 isoform 1 Protein

<400> SEQUENCE: 2

Met Ser Thr Pro Asp Pro Pro Leu Gly Gly Thr Pro Arg Pro Gly Pro
1               5                   10                  15

Ser Pro Gly Pro Gly Pro Ser Pro Gly Ala Met Leu Gly Pro Ser Pro
                20                  25                  30

Gly Pro Ser Pro Gly Ser Ala His Ser Met Met Gly Pro Ser Pro Gly
        35                  40                  45

Pro Pro Ser Ala Gly His Pro Ile Pro Thr Gln Gly Pro Gly Gly Tyr
    50                  55                  60

Pro Gln Asp Asn Met His Gln Met His Lys Pro Met Glu Ser Met His
65                  70                  75                  80

Glu Lys Gly Met Ser Asp Asp Pro Arg Tyr Asn Gln Met Lys Gly Met
                85                  90                  95

-continued

Gly Met Arg Ser Gly Gly His Ala Gly Met Gly Pro Pro Ser Pro
            100                 105                 110

Met Asp Gln His Ser Gln Gly Tyr Pro Ser Pro Leu Gly Gly Ser Glu
            115                 120                 125

His Ala Ser Ser Pro Val Pro Ala Ser Gly Pro Ser Ser Gly Pro Gln
            130                 135                 140

Met Ser Ser Gly Pro Gly Gly Ala Pro Leu Asp Gly Ala Asp Pro Gln
145                 150                 155                 160

Ala Leu Gly Gln Gln Asn Arg Gly Pro Thr Pro Phe Asn Gln Asn Gln
                165                 170                 175

Leu His Gln Leu Arg Ala Gln Ile Met Ala Tyr Lys Met Leu Ala Arg
            180                 185                 190

Gly Gln Pro Leu Pro Asp His Leu Gln Met Ala Val Gln Gly Lys Arg
            195                 200                 205

Pro Met Pro Gly Met Gln Gln Gln Met Pro Thr Leu Pro Pro Pro Ser
    210                 215                 220

Val Ser Ala Thr Gly Pro Gly Pro Gly Pro Gly Pro Gly Pro Gly Pro
225                 230                 235                 240

Gly Pro Gly Pro Ala Pro Pro Asn Tyr Ser Arg Pro His Gly Met Gly
                245                 250                 255

Gly Pro Asn Met Pro Pro Pro Gly Pro Ser Gly Val Pro Pro Gly Met
            260                 265                 270

Pro Gly Gln Pro Pro Gly Gly Pro Pro Lys Pro Trp Pro Glu Gly Pro
            275                 280                 285

Met Ala Asn Ala Ala Ala Pro Thr Ser Thr Pro Gln Lys Leu Ile Pro
    290                 295                 300

Pro Gln Pro Thr Gly Arg Pro Ser Pro Ala Pro Pro Ala Val Pro Pro
305                 310                 315                 320

Ala Ala Ser Pro Val Met Pro Pro Gln Thr Gln Ser Pro Gly Gln Pro
                325                 330                 335

Ala Gln Pro Ala Pro Met Val Pro Leu His Gln Lys Gln Ser Arg Ile
            340                 345                 350

Thr Pro Ile Gln Lys Pro Arg Gly Leu Asp Pro Val Glu Ile Leu Gln
            355                 360                 365

Glu Arg Glu Tyr Arg Leu Gln Ala Arg Ile Ala His Arg Ile Gln Glu
    370                 375                 380

Leu Glu Asn Leu Pro Gly Ser Leu Ala Gly Asp Leu Arg Thr Lys Ala
385                 390                 395                 400

Thr Ile Glu Leu Lys Ala Leu Arg Leu Leu Asn Phe Gln Arg Gln Leu
                405                 410                 415

Arg Gln Glu Val Val Val Cys Met Arg Arg Asp Thr Ala Leu Glu Thr
            420                 425                 430

Ala Leu Asn Ala Lys Ala Tyr Lys Arg Ser Lys Arg Gln Ser Leu Arg
            435                 440                 445

Glu Ala Arg Ile Thr Glu Lys Leu Glu Lys Gln Gln Lys Ile Glu Gln
    450                 455                 460

Glu Arg Lys Arg Arg Gln Lys His Gln Glu Tyr Leu Asn Ser Ile Leu
465                 470                 475                 480

Gln His Ala Lys Asp Phe Lys Glu Tyr His Arg Ser Val Thr Gly Lys
                485                 490                 495

Ile Gln Lys Leu Thr Lys Ala Val Ala Thr Tyr His Ala Asn Thr Glu
            500                 505                 510

```
Arg Glu Gln Lys Lys Glu Asn Glu Arg Ile Lys Glu Arg Met Arg
            515                 520                 525

Arg Leu Met Ala Glu Asp Glu Gly Tyr Arg Lys Leu Ile Asp Gln
    530                 535                 540

Lys Lys Asp Lys Arg Leu Ala Tyr Leu Leu Gln Gln Thr Asp Glu Tyr
545                 550                 555                 560

Val Ala Asn Leu Thr Glu Leu Val Arg Gln His Lys Ala Ala Gln Val
                565                 570                 575

Ala Lys Glu Lys Lys Lys Lys Lys Lys Lys Ala Glu Asn Ala
            580                 585                 590

Glu Gly Gln Thr Pro Ala Ile Gly Pro Asp Gly Glu Pro Leu Asp Glu
        595                 600                 605

Thr Ser Gln Met Ser Asp Leu Pro Val Lys Val Ile His Val Glu Ser
    610                 615                 620

Gly Lys Ile Leu Thr Gly Thr Asp Ala Pro Lys Ala Gly Gln Leu Glu
625                 630                 635                 640

Ala Trp Leu Glu Met Asn Pro Gly Tyr Glu Val Ala Pro Arg Ser Asp
                645                 650                 655

Ser Glu Glu Ser Gly Ser Glu Glu Glu Glu Glu Glu Glu Glu
        660                 665                 670

Gln Pro Gln Ala Ala Gln Pro Pro Thr Leu Pro Val Glu Glu Lys Lys
        675                 680                 685

Lys Ile Pro Asp Pro Asp Ser Asp Asp Val Ser Glu Val Asp Ala Arg
    690                 695                 700

His Ile Ile Glu Asn Ala Lys Gln Asp Val Asp Asp Glu Tyr Gly Val
705                 710                 715                 720

Ser Gln Ala Leu Ala Arg Gly Leu Gln Ser Tyr Tyr Ala Val Ala His
                725                 730                 735

Ala Val Thr Glu Arg Val Asp Lys Gln Ser Ala Leu Met Val Asn Gly
            740                 745                 750

Val Leu Lys Gln Tyr Gln Ile Lys Gly Leu Glu Trp Leu Val Ser Leu
        755                 760                 765

Tyr Asn Asn Asn Leu Asn Gly Ile Leu Ala Asp Glu Met Gly Leu Gly
    770                 775                 780

Lys Thr Ile Gln Thr Ile Ala Leu Ile Thr Tyr Leu Met Glu His Lys
785                 790                 795                 800

Arg Ile Asn Gly Pro Phe Leu Ile Ile Val Pro Leu Ser Thr Leu Ser
                805                 810                 815

Asn Trp Ala Tyr Glu Phe Asp Lys Trp Ala Pro Ser Val Val Lys Val
            820                 825                 830

Ser Tyr Lys Gly Ser Pro Ala Ala Arg Arg Ala Phe Val Pro Gln Leu
        835                 840                 845

Arg Ser Gly Lys Phe Asn Val Leu Leu Thr Thr Tyr Glu Tyr Ile Ile
    850                 855                 860

Lys Asp Lys His Ile Leu Ala Lys Ile Arg Trp Lys Tyr Met Ile Val
865                 870                 875                 880

Asp Glu Gly His Arg Met Lys Asn His His Cys Lys Leu Thr Gln Val
                885                 890                 895

Leu Asn Thr His Tyr Val Ala Pro Arg Arg Leu Leu Leu Thr Gly Thr
            900                 905                 910

Pro Leu Gln Asn Lys Leu Pro Glu Leu Trp Ala Leu Leu Asn Phe Leu
        915                 920                 925
```

```
Leu Pro Thr Ile Phe Lys Ser Cys Ser Thr Phe Glu Gln Trp Phe Asn
930                 935                 940

Ala Pro Phe Ala Met Thr Gly Glu Lys Val Asp Leu Asn Glu Glu
945                 950                 955                 960

Thr Ile Leu Ile Ile Arg Arg Leu His Lys Val Leu Arg Pro Phe Leu
                965                 970                 975

Leu Arg Arg Leu Lys Lys Glu Val Glu Ala Gln Leu Pro Glu Lys Val
                980                 985                 990

Glu Tyr Val Ile Lys Cys Asp Met Ser Ala Leu Gln Arg Val Leu Tyr
            995                 1000                1005

Arg His Met Gln Ala Lys Gly Val Leu Leu Thr Asp Gly Ser Glu
1010                1015                1020

Lys Asp Lys Lys Gly Lys Gly Thr Lys Thr Leu Met Asn Thr
1025                1030                1035

Ile Met Gln Leu Arg Lys Ile Cys Asn His Pro Tyr Met Phe Gln
1040                1045                1050

His Ile Glu Glu Ser Phe Ser Glu His Leu Gly Phe Thr Gly Gly
1055                1060                1065

Ile Val Gln Gly Leu Asp Leu Tyr Arg Ala Ser Gly Lys Phe Glu
1070                1075                1080

Leu Leu Asp Arg Ile Leu Pro Lys Leu Arg Ala Thr Asn His Lys
1085                1090                1095

Val Leu Leu Phe Cys Gln Met Thr Ser Leu Met Thr Ile Met Glu
1100                1105                1110

Asp Tyr Phe Ala Tyr Arg Gly Phe Lys Tyr Leu Arg Leu Asp Gly
1115                1120                1125

Thr Thr Lys Ala Glu Asp Arg Gly Met Leu Leu Lys Thr Phe Asn
1130                1135                1140

Glu Pro Gly Ser Glu Tyr Phe Ile Phe Leu Leu Ser Thr Arg Ala
1145                1150                1155

Gly Gly Leu Gly Leu Asn Leu Gln Ser Ala Asp Thr Val Ile Ile
1160                1165                1170

Phe Asp Ser Asp Trp Asn Pro His Gln Asp Leu Gln Ala Gln Asp
1175                1180                1185

Arg Ala His Arg Ile Gly Gln Gln Asn Glu Val Arg Val Leu Arg
1190                1195                1200

Leu Cys Thr Val Asn Ser Val Glu Glu Lys Ile Leu Ala Ala Ala
1205                1210                1215

Lys Tyr Lys Leu Asn Val Asp Gln Lys Val Ile Gln Ala Gly Met
1220                1225                1230

Phe Asp Gln Lys Ser Ser Ser His Glu Arg Arg Ala Phe Leu Gln
1235                1240                1245

Ala Ile Leu Glu His Glu Gln Asp Glu Glu Asp Glu Val
1250                1255                1260

Pro Asp Asp Glu Thr Val Asn Gln Met Ile Ala Arg His Glu Glu
1265                1270                1275

Glu Phe Asp Leu Phe Met Arg Met Asp Leu Asp Arg Arg Arg Glu
1280                1285                1290

Glu Ala Arg Asn Pro Lys Arg Lys Pro Arg Leu Met Glu Glu Asp
1295                1300                1305

Glu Leu Pro Ser Trp Ile Ile Lys Asp Asp Ala Glu Val Glu Arg
1310                1315                1320
```

```
Leu Thr Cys Glu Glu Glu Glu Lys Met Phe Gly Arg Gly Ser
    1325                1330                1335

Arg His Arg Lys Glu Val Asp Tyr Ser Asp Ser Leu Thr Glu Lys
    1340                1345                1350

Gln Trp Leu Lys Ala Ile Glu Glu Gly Thr Leu Glu Glu Ile Glu
    1355                1360                1365

Glu Glu Val Arg Gln Lys Lys Ser Ser Arg Lys Arg Lys Arg Asp
    1370                1375                1380

Ser Asp Ala Gly Ser Ser Thr Pro Thr Thr Ser Thr Arg Ser Arg
    1385                1390                1395

Asp Lys Asp Asp Glu Ser Lys Lys Gln Lys Lys Arg Gly Arg Pro
    1400                1405                1410

Pro Ala Glu Lys Leu Ser Pro Asn Pro Pro Asn Leu Thr Lys Lys
    1415                1420                1425

Met Lys Lys Ile Val Asp Ala Val Ile Lys Tyr Lys Asp Ser Ser
    1430                1435                1440

Ser Gly Arg Gln Leu Ser Glu Val Phe Ile Gln Leu Pro Ser Arg
    1445                1450                1455

Lys Glu Leu Pro Glu Tyr Tyr Glu Leu Ile Arg Lys Pro Val Asp
    1460                1465                1470

Phe Lys Lys Ile Lys Glu Arg Ile Arg Asn His Lys Tyr Arg Ser
    1475                1480                1485

Leu Asn Asp Leu Glu Lys Asp Val Met Leu Leu Cys Gln Asn Ala
    1490                1495                1500

Gln Thr Phe Asn Leu Glu Gly Ser Leu Ile Tyr Glu Asp Ser Ile
    1505                1510                1515

Val Leu Gln Ser Val Phe Thr Ser Val Arg Gln Lys Ile Glu Lys
    1520                1525                1530

Glu Asp Asp Ser Glu Gly Glu Glu Ser Glu Glu Glu Glu Glu Gly
    1535                1540                1545

Glu Glu Glu Gly Ser Glu Ser Glu Ser Arg Ser Val Lys Val Lys
    1550                1555                1560

Ile Lys Leu Gly Arg Lys Glu Lys Ala Gln Asp Arg Leu Lys Gly
    1565                1570                1575

Gly Arg Arg Arg Pro Ser Arg Gly Ser Arg Ala Lys Pro Val Val
    1580                1585                1590

Ser Asp Asp Asp Ser Glu Glu Glu Gln Glu Glu Asp Arg Ser Gly
    1595                1600                1605

Ser Gly Ser Glu Glu Asp
    1610

<210> SEQ ID NO 3
<211> LENGTH: 4854
<212> TYPE: DNA
<213> ORGANISM: Homo sapiens
<220> FEATURE:
<223> OTHER INFORMATION: Homo sapiens SMARCA4 isoform 2 mRNA

<400> SEQUENCE: 3
atgtccactc cagacccacc cctgggcgga actcctcggc caggtccttc cccgggccct    60
ggcccttccc ctggagccat gctgggccct agcccgggtc cctcgccggg ctccgcccac   120
agcatgatgg ggcccagccc agggccgccc tcagcaggac accccatccc cacccagggg   180
cctggagggt accctcagga caacatgcac cagatgcaca agcccatgga gtccatgcat   240
gagaagggca tgtcggacga cccgcgctac aaccagatga aggaatggg gatgcggtca   300
```

```
gggggccatg ctgggatggg gcccccgccc agccccatgg accagcactc ccaaggttac    360
ccctcgcccc tgggtggctc tgagcatgcc tctagtccag ttccagccag tggcccgtct    420
tcggggcccc agatgtcttc cgggccagga ggtgccccgc tggatggtgc tgaccccccag    480 gccttggggc agcagaaccg ggcccaacc ccatttaacc agaaccagct gcaccagctc    540
agagctcaga tcatggccta caagatgctg gccagggggc agcccctccc cgaccacctg    600
cagatggcgg tgcagggcaa gcggccgatg cccgggatgc agcagcagat gccaacgcta    660
cctccaccct cggtgtccgc aacaggaccc ggccctggcc ctggccctgg ccccggcccg    720
ggtcccggcc cggcacctcc aaattacagc aggcctcatg gtatgggagg cccaacatg    780 cctcccccag gaccctcggg cgtgcccccc gggatgccag gccagcctcc tggagggcct    840
cccaagccct ggcctgaagg acccatggcg aatgctgctg cccccacgag cacccctcag    900
aagctgattc ccccgcagcc aacgggccgc ccttcccccg cgcccctgc cgtcccaccc    960 gccgcctcgc ccgtgatgcc accgcagacc cagtccccccg ggcagccggc ccagcccgcg   1020
cccatggtgc cactgcacca gaagcagagc cgcatcaccc ccatccagaa gccgcggggc   1080
ctcgaccctg tggagatcct gcaggagcgc gagtacaggc tgcaggctcg catcgcacac   1140
cgaattcagg aacttgaaaa ccttcccggg tccctggccg gggatttgcg aaccaaagcg   1200
accattgagc tcaaggccct caggctgctg aacttccaga ggcagctgcg ccaggaggtg   1260
gtggtgtgca tgcggaggga cacagcgctg gagacagccc tcaatgctaa ggcctacaag   1320
cgcagcaagc gccagtccct gcgcgaggcc cgcatcactg agaagctgga gaagcagcag   1380
aagatcgagc aggagcgcaa gcgccggcag aagcaccagg aatacctcaa tagcattctc   1440
cagcatgcca aggatttcaa ggaatatcac agatccgtca caggcaaaat ccagaagctg   1500
accaaggcag tggccacgta ccatgccaac acggagcggg agcagaagaa agagaacgag   1560
cggatcgaga aggagcgcat gcggaggctc atggctgaag atgaggaggg gtaccgcaag   1620
ctcatcgacc agaagaagga caagcgcctg gcctacctct gcagcagac agacgagtac   1680 gtggctaacc tcacggagct ggtgcggcag cacaaggctg cccaggtcgc caaggagaaa   1740
aagaagaaaa agaaaaagaa gaaggcagaa aatgcagaag acagacgcc tgccattggg   1800 ccggatggcg agcctctgga cgagaccagc cagatgagcg acctcccggt gaaggtgatc   1860
cacgtggaga gtgggaagat cctcacaggc acagatgccc ccaaagccgg gcagctggag   1920
gcctggctcg agatgaaccc ggggtatgaa gtagctccga ggtctgatag tgaagaaagt   1980
ggctcagaag aagaggaaga ggaggaggag gaagagcagc cgcaggcagc acagcctccc   2040
accctgcccg tggaggagaa gaagaagatt ccagatccag acagcgatga cgtctctgag   2100
gtggacgcgc ggcacatcat tgagaatgcc aagcaagatg tcgatgatga atatggcgtg   2160
tcccaggccc ttgcacgtgg cctgcagtcc tactatgccg tggcccatgc tgtcactgag   2220
agagtggaca agcagtcagc gcttatggtc aatggtgtcc tcaaacagta ccagatcaaa   2280
ggtttggagt ggctggtgtc cctgtacaac aacaacctga cggcatcct ggccgacgag   2340 atgggcctgg ggaagaccat ccagaccatc gcgctcatca cgtacctcat ggagcacaaa   2400
cgcatcaatg gcccttcct catcatcgtg cctctctcaa cgctgtccaa ctgggcgtac   2460
gagtttgaca agtgggcccc ctccgtggtg aaggtgtctt acaagggatc cccagcagca   2520
agacgggcct ttgtccccca gctccggagt gggaagttca acgtcttgct gacgacgtac   2580
gagtacatca tcaaagacaa gcacatcctc gccaagatcc gttggaagta catgattgtg   2640
gacgaaggtc accgcatgaa gaaccaccac tgcaagctga cgcaggtgct caacacgcac   2700
```

```
tatgtggcac ccgccgcct gctgctgacg ggcacaccgc tgcagaacaa gcttcccgag   2760
ctctgggcgc tgctcaactt cctgctgccc accatcttca agagctgcag caccttcgag   2820
cagtggttta acgcacccct tgccatgacc ggggaaaagg tggacctgaa tgaggaggaa   2880
accattctca tcatccggcg tctccacaaa gtgctgcggc ccttcttgct ccgacgactc   2940
aagaaggaag tcgaggccca gttgcccgaa aaggtggagt acgtcatcaa gtgcgacatg   3000
tctgcgctgc agcgagtgct ctaccgccac atgcaggcca agggcgtgct gctgactgat   3060
ggctccgaga aggacaagaa gggcaaaggc ggcaccaaga ccctgatgaa caccatcatg   3120
cagctgcgga agatctgcaa ccaccccctac atgttccagc acatcgagga gtccttttcc   3180
gagcacttgg ggttcactgg cggcattgtc caagggctgg acctgtaccg agcctcgggt   3240
aaatttgagc ttcttgatag aattcttccc aaactccgag caaccaacca caaagtgctg   3300
ctgttctgcc aaatgacctc cctcatgacc atcatggaag attactttgc gtatcgcggc   3360
tttaaatacc tcaggcttga tggaaccacg aaggcggagg accggggcat gctgctgaaa   3420
accttcaacg agcccggctc tgagtacttc atcttcctgc tcagcacccg ggctgggggg   3480
ctcggcctga acctccagtc ggcagacact gtgatcattt ttgacagcga ctggaatcct   3540
caccaggacc tgcaagcgca ggaccgagcc caccgcatcg gcagcagaa cgaggtgcgt   3600
gtgctccgcc tctgcaccgt caacagcgtg gaggagaaga tcctagctgc agccaagtac   3660
aagctcaacg tggaccagaa ggtgatccag gccggcatgt tcgaccagaa gtcctccagc   3720
catgagcggc gcgccttcct gcaggccatc ctggagcacg aggagcagga tgaggaggaa   3780
gacgaggtgc ccgacgacga gaccgtcaac cagatgatcg cccggcacga ggaggagttt   3840
gatctgttca tgcgcatgga cctggaccgc aggcgcgagg aggcccgcaa ccccaagcgg   3900
aagccgcgcc tcatggagga ggacgagctc ccctcgtgga tcatcaagga cgacgcggag   3960
gtggagcggc tgacctgtga ggaggaggag gagaagatgt tcggccgtgg ctcccgccac   4020
cgcaaggagg tggactacag cgactcactg acggagaagc agtggctcaa gaccctgaag   4080
gccatcgagg agggcacgct ggaggagatc gaagaggagg tccggcagaa gaaatcatca   4140
cggaagcgca agcgagacag cgacgccggc tcctccaccc cgaccaccag cacccgcagc   4200
cgcgacaagg acgacgagag caagaagcag aagaagcgcg gcggccgcc tgccgagaaa   4260
ctctccccta acccacccaa cctcaccaag aagatgaaga agattgtgga tgccgtgatc   4320
aagtacaagg acagcagcag tggacgtcag ctcagcgagg tcttcatcca gctgcctcg   4380
cgaaaggagc tgcccgagta ctacgagctc atccgcaagc cgtggacttc aagaagata   4440
aaggagcgca ttcgcaacca caagtaccgc agcctcaacg acctagagaa ggacgtcatg   4500
ctcctgtgcc agaacgcaca gaccttcaac ctggagggct cctgatcta tgaagactcc   4560
atcgtcttgc agtcggtctt caccagcgtg cggcagaaaa tcgagaagga ggatgacagt   4620
gaaggcgagg agagtgagga ggaggaagag ggcgaggagg aaggctccga atccgaatct   4680
cggtccgtca aagtgaagat caagcttggc cggaaggaga aggcacagga ccggctgaag   4740
ggcggccggc ggcggccgag ccgagggtcc cgagccaagc cggtcgtgag tgacgatgac   4800
agtgaggagg aacaagagga ggaccgctca ggaagtggca gcgaagaaga ctga         4854
```

<210> SEQ ID NO 4
<211> LENGTH: 1617
<212> TYPE: PRT
<213> ORGANISM: Homo sapiens
<220> FEATURE:
<223> OTHER INFORMATION: Homo sapiens SMARCA4 isoform 2 Protein

```
<400> SEQUENCE: 4

Met Ser Thr Pro Asp Pro Pro Leu Gly Gly Thr Pro Arg Pro Gly Pro
1               5                   10                  15

Ser Pro Gly Pro Gly Pro Ser Pro Gly Ala Met Leu Gly Pro Ser Pro
            20                  25                  30

Gly Pro Ser Pro Gly Ser Ala His Ser Met Met Gly Pro Ser Pro Gly
        35                  40                  45

Pro Pro Ser Ala Gly His Pro Ile Pro Thr Gln Gly Pro Gly Gly Tyr
    50                  55                  60

Pro Gln Asp Asn Met His Gln Met His Lys Pro Met Glu Ser Met His
65                  70                  75                  80

Glu Lys Gly Met Ser Asp Asp Pro Arg Tyr Asn Gln Met Lys Gly Met
                85                  90                  95

Gly Met Arg Ser Gly Gly His Ala Gly Met Gly Pro Pro Ser Pro
            100                 105                 110

Met Asp Gln His Ser Gln Gly Tyr Pro Ser Pro Leu Gly Gly Ser Glu
            115                 120                 125

His Ala Ser Ser Pro Val Pro Ala Ser Gly Pro Ser Ser Gly Pro Gln
            130                 135                 140

Met Ser Ser Gly Pro Gly Gly Ala Pro Leu Asp Gly Ala Asp Pro Gln
145                 150                 155                 160

Ala Leu Gly Gln Gln Asn Arg Gly Pro Thr Pro Phe Asn Gln Asn Gln
                165                 170                 175

Leu His Gln Leu Arg Ala Gln Ile Met Ala Tyr Lys Met Leu Ala Arg
            180                 185                 190

Gly Gln Pro Leu Pro Asp His Leu Gln Met Ala Val Gln Gly Lys Arg
            195                 200                 205

Pro Met Pro Gly Met Gln Gln Gln Met Pro Thr Leu Pro Pro Pro Ser
210                 215                 220

Val Ser Ala Thr Gly Pro Gly Pro Gly Pro Gly Pro Gly Pro Gly Pro
225                 230                 235                 240

Gly Pro Gly Pro Ala Pro Pro Asn Tyr Ser Arg Pro His Gly Met Gly
            245                 250                 255

Gly Pro Asn Met Pro Pro Pro Gly Pro Ser Gly Val Pro Pro Gly Met
            260                 265                 270

Pro Gly Gln Pro Pro Gly Gly Pro Pro Lys Pro Trp Pro Glu Gly Pro
            275                 280                 285

Met Ala Asn Ala Ala Ala Pro Thr Ser Thr Pro Gln Lys Leu Ile Pro
290                 295                 300

Pro Gln Pro Thr Gly Arg Pro Ser Pro Ala Pro Pro Ala Val Pro Pro
305                 310                 315                 320

Ala Ala Ser Pro Val Met Pro Pro Gln Thr Gln Ser Pro Gly Gln Pro
                325                 330                 335

Ala Gln Pro Ala Pro Met Val Pro Leu His Gln Lys Gln Ser Arg Ile
            340                 345                 350

Thr Pro Ile Gln Lys Pro Arg Gly Leu Asp Pro Val Glu Ile Leu Gln
            355                 360                 365

Glu Arg Glu Tyr Arg Leu Gln Ala Arg Ile Ala His Arg Ile Gln Glu
            370                 375                 380

Leu Glu Asn Leu Pro Gly Ser Leu Ala Gly Asp Leu Arg Thr Lys Ala
385                 390                 395                 400

Thr Ile Glu Leu Lys Ala Leu Arg Leu Leu Asn Phe Gln Arg Gln Leu
                405                 410                 415
```

```
Arg Gln Glu Val Val Cys Met Arg Arg Asp Thr Ala Leu Glu Thr
            420                 425                 430
Ala Leu Asn Ala Lys Ala Tyr Lys Arg Ser Lys Arg Gln Ser Leu Arg
            435                 440                 445
Glu Ala Arg Ile Thr Glu Lys Leu Glu Lys Gln Gln Lys Ile Glu Gln
        450                 455                 460
Glu Arg Lys Arg Arg Gln Lys His Gln Glu Tyr Leu Asn Ser Ile Leu
465                 470                 475                 480
Gln His Ala Lys Asp Phe Lys Glu Tyr His Arg Ser Val Thr Gly Lys
                485                 490                 495
Ile Gln Lys Leu Thr Lys Ala Val Ala Thr Tyr His Ala Asn Thr Glu
            500                 505                 510
Arg Glu Gln Lys Lys Glu Asn Glu Arg Ile Glu Lys Glu Arg Met Arg
        515                 520                 525
Arg Leu Met Ala Glu Asp Glu Gly Tyr Arg Lys Leu Ile Asp Gln
        530                 535                 540
Lys Lys Asp Lys Arg Leu Ala Tyr Leu Leu Gln Gln Thr Asp Glu Tyr
545                 550                 555                 560
Val Ala Asn Leu Thr Glu Leu Val Arg Gln His Lys Ala Ala Gln Val
                565                 570                 575
Ala Lys Glu Lys Lys Lys Lys Lys Lys Lys Ala Glu Asn Ala
            580                 585                 590
Glu Gly Gln Thr Pro Ala Ile Gly Pro Asp Gly Glu Pro Leu Asp Glu
        595                 600                 605
Thr Ser Gln Met Ser Asp Leu Pro Val Lys Val Ile His Val Glu Ser
        610                 615                 620
Gly Lys Ile Leu Thr Gly Thr Asp Ala Pro Lys Ala Gly Gln Leu Glu
625                 630                 635                 640
Ala Trp Leu Glu Met Asn Pro Gly Tyr Glu Val Ala Pro Arg Ser Asp
                645                 650                 655
Ser Glu Glu Ser Gly Ser Glu Glu Glu Glu Glu Glu Glu Glu
            660                 665                 670
Gln Pro Gln Ala Ala Gln Pro Pro Thr Leu Pro Val Glu Glu Lys Lys
        675                 680                 685
Lys Ile Pro Asp Pro Asp Ser Asp Asp Val Ser Glu Val Asp Ala Arg
        690                 695                 700
His Ile Ile Glu Asn Ala Lys Gln Asp Val Asp Asp Glu Tyr Gly Val
705                 710                 715                 720
Ser Gln Ala Leu Ala Arg Gly Leu Gln Ser Tyr Tyr Ala Val Ala His
                725                 730                 735
Ala Val Thr Glu Arg Val Asp Lys Gln Ser Ala Leu Met Val Asn Gly
            740                 745                 750
Val Leu Lys Gln Tyr Gln Ile Lys Gly Leu Glu Trp Leu Val Ser Leu
        755                 760                 765
Tyr Asn Asn Asn Leu Asn Gly Ile Leu Ala Asp Glu Met Gly Leu Gly
        770                 775                 780
Lys Thr Ile Gln Thr Ile Ala Leu Ile Thr Tyr Leu Met Glu His Lys
785                 790                 795                 800
Arg Ile Asn Gly Pro Phe Leu Ile Ile Val Pro Leu Ser Thr Leu Ser
                805                 810                 815
Asn Trp Ala Tyr Glu Phe Asp Lys Trp Ala Pro Ser Val Val Lys Val
            820                 825                 830
```

-continued

Ser Tyr Lys Gly Ser Pro Ala Ala Arg Arg Ala Phe Val Pro Gln Leu
            835                 840                 845

Arg Ser Gly Lys Phe Asn Val Leu Leu Thr Thr Tyr Glu Tyr Ile Ile
850                 855                 860

Lys Asp Lys His Ile Leu Ala Lys Ile Arg Trp Lys Tyr Met Ile Val
865                 870                 875                 880

Asp Glu Gly His Arg Met Lys Asn His His Cys Lys Leu Thr Gln Val
            885                 890                 895

Leu Asn Thr His Tyr Val Ala Pro Arg Arg Leu Leu Leu Thr Gly Thr
            900                 905                 910

Pro Leu Gln Asn Lys Leu Pro Glu Leu Trp Ala Leu Leu Asn Phe Leu
            915                 920                 925

Leu Pro Thr Ile Phe Lys Ser Cys Ser Thr Phe Glu Gln Trp Phe Asn
930                 935                 940

Ala Pro Phe Ala Met Thr Gly Glu Lys Val Asp Leu Asn Glu Glu Glu
945                 950                 955                 960

Thr Ile Leu Ile Ile Arg Arg Leu His Lys Val Leu Arg Pro Phe Leu
            965                 970                 975

Leu Arg Arg Leu Lys Lys Glu Val Glu Ala Gln Leu Pro Glu Lys Val
            980                 985                 990

Glu Tyr Val Ile Lys Cys Asp Met Ser Ala Leu Gln Arg Val Leu Tyr
            995                 1000                1005

Arg His Met Gln Ala Lys Gly Val Leu Leu Thr Asp Gly Ser Glu
            1010                1015                1020

Lys Asp Lys Lys Gly Lys Gly Gly Thr Lys Thr Leu Met Asn Thr
            1025                1030                1035

Ile Met Gln Leu Arg Lys Ile Cys Asn His Pro Tyr Met Phe Gln
            1040                1045                1050

His Ile Glu Glu Ser Phe Ser Glu His Leu Gly Phe Thr Gly Gly
            1055                1060                1065

Ile Val Gln Gly Leu Asp Leu Tyr Arg Ala Ser Gly Lys Phe Glu
            1070                1075                1080

Leu Leu Asp Arg Ile Leu Pro Lys Leu Arg Ala Thr Asn His Lys
            1085                1090                1095

Val Leu Leu Phe Cys Gln Met Thr Ser Leu Met Thr Ile Met Glu
            1100                1105                1110

Asp Tyr Phe Ala Tyr Arg Gly Phe Lys Tyr Leu Arg Leu Asp Gly
            1115                1120                1125

Thr Thr Lys Ala Glu Asp Arg Gly Met Leu Leu Lys Thr Phe Asn
            1130                1135                1140

Glu Pro Gly Ser Glu Tyr Phe Ile Phe Leu Leu Ser Thr Arg Ala
            1145                1150                1155

Gly Gly Leu Gly Leu Asn Leu Gln Ser Ala Asp Thr Val Ile Ile
            1160                1165                1170

Phe Asp Ser Asp Trp Asn Pro His Gln Asp Leu Gln Ala Gln Asp
            1175                1180                1185

Arg Ala His Arg Ile Gly Gln Gln Asn Glu Val Arg Val Leu Arg
            1190                1195                1200

Leu Cys Thr Val Asn Ser Val Glu Glu Lys Ile Leu Ala Ala Ala
            1205                1210                1215

Lys Tyr Lys Leu Asn Val Asp Gln Lys Val Ile Gln Ala Gly Met
            1220                1225                1230

```
Phe Asp Gln Lys Ser Ser Ser His Glu Arg Arg Ala Phe Leu Gln
1235                1240                1245

Ala Ile Leu Glu His Glu Glu Gln Asp Glu Glu Glu Asp Glu Val
1250                1255                1260

Pro Asp Asp Glu Thr Val Asn Gln Met Ile Ala Arg His Glu Glu
1265                1270                1275

Glu Phe Asp Leu Phe Met Arg Met Asp Leu Asp Arg Arg Arg Glu
1280                1285                1290

Glu Ala Arg Asn Pro Lys Arg Lys Pro Arg Leu Met Glu Glu Asp
1295                1300                1305

Glu Leu Pro Ser Trp Ile Ile Lys Asp Asp Ala Glu Val Glu Arg
1310                1315                1320

Leu Thr Cys Glu Glu Glu Glu Lys Met Phe Gly Arg Gly Ser
1325                1330                1335

Arg His Arg Lys Glu Val Asp Tyr Ser Asp Ser Leu Thr Glu Lys
1340                1345                1350

Gln Trp Leu Lys Thr Leu Lys Ala Ile Glu Glu Gly Thr Leu Glu
1355                1360                1365

Glu Ile Glu Glu Glu Val Arg Gln Lys Lys Ser Arg Lys Arg
1370                1375                1380

Lys Arg Asp Ser Asp Ala Gly Ser Ser Thr Pro Thr Thr Ser Thr
1385                1390                1395

Arg Ser Arg Asp Lys Asp Glu Ser Lys Lys Gln Lys Lys Arg
1400                1405                1410

Gly Arg Pro Pro Ala Glu Lys Leu Ser Pro Asn Pro Pro Asn Leu
1415                1420                1425

Thr Lys Lys Met Lys Lys Ile Val Asp Ala Val Ile Lys Tyr Lys
1430                1435                1440

Asp Ser Ser Ser Gly Arg Gln Leu Ser Glu Val Phe Ile Gln Leu
1445                1450                1455

Pro Ser Arg Lys Glu Leu Pro Glu Tyr Tyr Glu Leu Ile Arg Lys
1460                1465                1470

Pro Val Asp Phe Lys Lys Ile Lys Glu Arg Ile Arg Asn His Lys
1475                1480                1485

Tyr Arg Ser Leu Asn Asp Leu Glu Lys Asp Val Met Leu Leu Cys
1490                1495                1500

Gln Asn Ala Gln Thr Phe Asn Leu Glu Gly Ser Leu Ile Tyr Glu
1505                1510                1515

Asp Ser Ile Val Leu Gln Ser Val Phe Thr Ser Val Arg Gln Lys
1520                1525                1530

Ile Glu Lys Glu Asp Asp Ser Glu Gly Glu Glu Ser Glu Glu Glu
1535                1540                1545

Glu Glu Gly Glu Glu Glu Gly Ser Glu Ser Glu Ser Arg Ser Val
1550                1555                1560

Lys Val Lys Ile Lys Leu Gly Arg Lys Glu Lys Ala Gln Asp Arg
1565                1570                1575

Leu Lys Gly Gly Arg Arg Pro Ser Arg Gly Ser Arg Ala Lys
1580                1585                1590

Pro Val Val Ser Asp Asp Asp Ser Glu Glu Gln Glu Glu Asp
1595                1600                1605

Arg Ser Gly Ser Gly Ser Glu Asp
1610                1615
```

<210> SEQ ID NO 5
<211> LENGTH: 4842
<212> TYPE: DNA
<213> ORGANISM: Homo sapiens
<220> FEATURE:
<223> OTHER INFORMATION: Homo sapiens SMARCA4 isoform 3 mRNA

<400> SEQUENCE: 5

| | | | | | |
|---|---|---|---|---|---|
| atgtccactc | cagacccacc | cctgggcgga | actcctcggc | caggtccttc | cccgggccct | 60 |
| ggcccttccc | ctggagccat | gctgggccct | agcccgggtc | cctcgccggg | ctccgcccac | 120 |
| agcatgatgg | ggcccagccc | agggccgccc | tcagcaggac | accccatccc | cacccagggg | 180 |
| cctggagggt | accctcagga | caacatgcac | cagatgcaca | agcccatgga | gtccatgcat | 240 |
| gagaagggca | tgtcggacga | cccgcgctac | aaccagatga | aggaatggga | gatgcggtca | 300 |
| gggggccatg | ctgggatggg | gccccgcccc | agcccatggg | accagcactc | ccaaggttac | 360 |
| ccctcgcccc | tgggtggctc | tgagcatgcc | tctagtccag | ttccagccag | tggcccgtct | 420 |
| tcggggcccc | agatgtcttc | cgggccagga | ggtgccccgc | tggatggtgc | tgaccccag | 480 |
| gccttgggc | agcagaaccg | ggcccaacc | ccatttaacc | agaaccagct | gcaccagctc | 540 |
| agagctcaga | tcatggccta | caagatgctg | gccaggggc | agcccctccc | cgaccacctg | 600 |
| cagatggcgg | tgcagggcaa | gcggccgatg | cccgggatgc | agcagcagat | gccaacgcta | 660 |
| cctccaccct | cggtgtccgc | aacaggaccc | ggcctggcc | ctggccctgg | ccccggcccg | 720 |
| ggtcccggcc | cggcacctcc | aaattacagc | aggcctcatg | gtatgggagg | gcccaacatg | 780 |
| cctcccccag | accctcggg | cgtgcccccc | gggatgccag | gccagcctcc | tggagggcct | 840 |
| cccaagccct | ggcctgaagg | acccatggcg | aatgctgctg | ccccacgag | caccctcag | 900 |
| aagctgattc | cccgcagcc | aacgggccgc | ccttccccg | cgcccctgc | cgtcccaccc | 960 |
| gccgcctcgc | ccgtgatgcc | accgcagacc | cagtcccccg | ggcagccggc | ccagcccgcg | 1020 |
| cccatggtgc | cactgcacca | gaagcagagc | cgcatcaccc | ccatccagaa | gccgcggggc | 1080 |
| ctcgaccctg | tggagatcct | gcaggagcgc | gagtacaggc | tgcaggctcg | catcgcacac | 1140 |
| cgaattcagg | aacttgaaaa | ccttcccggg | tccctggccg | gggatttgcg | aaccaaagcg | 1200 |
| accattgagc | tcaaggccct | caggctgctg | aacttccaga | ggcagctgcg | ccaggaggtg | 1260 |
| gtggtgtgca | tgcggaggga | cacagcgctg | gagacagccc | tcaatgctaa | ggcctacaag | 1320 |
| cgcagcaagc | gccagtccct | gcgcgaggcc | cgcatcactg | agaagctgga | gaagcagcag | 1380 |
| aagatcgagc | aggagcgcaa | gcgccggcag | aagcaccagg | aatacctcaa | tagcattctc | 1440 |
| cagcatgcca | aggatttcaa | ggaatatcac | agatccgtca | caggcaaaat | ccagaagctg | 1500 |
| accaaggcag | tggccacgta | ccatgccaac | acggagcggg | agcagaagaa | agaaaacgag | 1560 |
| cggatcgaga | aggagcgcat | gcggaggctc | atggctgaag | atgaggaggg | gtaccgcaag | 1620 |
| ctcatcgacc | agaagaagga | caagcgcctg | gcctacctct | tgcagcagac | agacgagtac | 1680 |
| gtggctaacc | tcacggagct | ggtgcggcag | cacaaggctg | cccaggtcgc | caaggagaaa | 1740 |
| aagaagaaaa | agaaaaagaa | gaaggcagaa | aatgcagaag | gacagacgcc | tgccattggg | 1800 |
| ccggatggcg | agcctctgga | cgagaccagc | cagatgagcg | acctcccggt | gaaggtgatc | 1860 |
| cacgtggaga | gtgggaagat | cctcacaggc | acagatgccc | ccaaagccgg | gcagctggag | 1920 |
| gcctggctcg | agatgaaccc | ggggtatgaa | gtagctccga | ggtctgatag | tgaagaaagt | 1980 |
| ggctcagaag | aagaggaaga | ggaggaggag | gaagagcagc | cgcaggcagc | acagcctccc | 2040 |
| accctgcccg | tggaggagaa | gaagaagatt | ccagatccag | acagcgatga | cgtctctgag | 2100 |

-continued

```
gtggacgcgc ggcacatcat tgagaatgcc aagcaagatg tcgatgatga atatggcgtg    2160
tcccaggccc ttgcacgtgg cctgcagtcc tactatgccg tggcccatgc tgtcactgag    2220
agagtggaca agcagtcagc gcttatggtc aatggtgtcc tcaaacagta ccagatcaaa    2280
ggtttggagt ggctggtgtc cctgtacaac aacaacctga acggcatcct ggccgacgag    2340
atgggcctgg ggaagaccat ccagaccatc gcgctcatca cgtacctcat ggagcacaaa    2400
cgcatcaatg ggcccttcct catcatcgtg cctctctcaa cgctgtccaa ctgggcgtac    2460
gagtttgaca gtgggcccc ctccgtggtg aaggtgtctt acaagggatc cccagcagca    2520
agacgggcct ttgtccccca gctccggagt gggaagttca acgtcttgct gacgacgtac    2580
gagtacatca tcaaagacaa gcacatcctc gccaagatcc gttggaagta catgattgtg    2640
gacgaaggtc accgcatgaa gaaccaccac tgcaagctga cgcaggtgct caacacgcac    2700
tatgtggcac cccgccgcct gctgctgacg ggcacaccgc tgcagaacaa gcttcccgag    2760
ctctgggcgc tgctcaactt cctgctgccc accatcttca agagctgcag caccttcgag    2820
cagtggttta acgcaccctt tgccatgacc ggggaaaagg tggacctgaa tgaggaggaa    2880
accattctca tcatccggcg tctccacaaa gtgctgcggc ccttcttgct ccgacgactc    2940
aagaaggaag tcgaggccca gttgcccgaa aaggtggagt acgtcatcaa gtgcgacatg    3000
tctgcgctgc agcgagtgct ctaccgccac atgcaggcca agggcgtgct gctgactgat    3060
ggctccgaga aggacaagaa gggcaaaggc ggcaccaaga ccctgatgaa caccatcatg    3120
cagctgcgga agatctgcaa ccaccccctac atgttccagc acatcgagga gtccttttcc    3180
gagcacttgg ggttcactgg cggcattgtc caagggctgg acctgtaccg agcctcgggt    3240
aaatttgagc ttcttgatag aattcttccc aaactccgag caaccaacca caaagtgctg    3300
ctgttctgcc aaatgacctc cctcatgacc atcatggaag attactttgc gtatcgcggc    3360
tttaaatacc tcaggcttga tggaaccacg aaggcggagg accggggcat gctgctgaaa    3420
accttcaacg agcccggctc tgagtacttc atcttcctgc tcagcacccg ggctgggggg    3480
ctcggcctga acctccagtc ggcagacact gtgatcattt ttgacagcga ctggaatcct    3540
caccaggacc tgcaagcgca ggaccgagcc caccgcatcg ggcagcagaa cgaggtgcgt    3600
gtgctccgcc tctgcaccgt caacagcgtg gaggagaaga tcctagctgc agccaagtac    3660
aagctcaacg tggaccagaa ggtgatccag gccggcatgt tcgaccagaa gtcctccagc    3720
catgagcggc gcgccttcct gcaggccatc ctggagcacg aggagcagga tgaggaggaa    3780
gacgaggtgc ccgacgacga gaccgtcaac cagatgatcg cccggcacga ggaggagttt    3840
gatctgttca tgcgcatgga cctggaccgc aggcgcgagg aggcccgcaa ccccaagcgg    3900
aagccgcgcc tcatggagga ggacgagctc cctcgtggga tcatcaagga cgacgcggag    3960
gtggagcggc tgacctgtga ggaggaggag agaagatgt tcggccgtgg ctcccgccac    4020
cgcaaggagg tggactacag cgactcactg acgagaagc agtggctcaa ggccatcgag    4080
gagggcacgc tggaggagat cgaagaggag gtccggcaga agaaatcatc acggaagcgc    4140
aagcgagaca gcgacgccgg ctcctccacc ccgaccacca gcacccgcag ccgcgacaag    4200
gacgacgaga gcaagaagca gaagaagcgc gggcggccgc ctgccgagaa actctcccct    4260
aacccaccca acctcaccaa gaagatgaag aagattgtgg atgccgtgat caagtacaag    4320
gacagcagtg gacgtcagct cagcgaggtc ttcatccagc tgcccctcgcg aaaggagctg    4380 cccgagtact acgagctcat ccgcaagccc gtggacttca gaagataaa ggagcgcatt    4440 cgcaaccaca agtaccgcag cctcaacgac ctagagaagg acgtcatgct cctgtgccag    4500
```

```
aacgcacaga ccttcaacct ggagggctcc ctgatctatg aagactccat cgtcttgcag   4560
tcggtcttca ccagcgtgcg gcagaaaatc gagaaggagg atgacagtga aggcgaggag   4620
agtgaggagg aggaagaggg cgaggaggaa ggctccgaat ccgaatctcg gtccgtcaaa   4680
gtgaagatca agcttggccg gaaggagaag gcacaggacc ggctgaaggg cggccggcgg   4740
cggccgagcc gagggtcccg agccaagccg gtcgtgagtg acgatgacag tgaggaggaa   4800
caagaggagg accgctcagg aagtggcagc gaagaagact ga                     4842
```

<210> SEQ ID NO 6
<211> LENGTH: 1613
<212> TYPE: PRT
<213> ORGANISM: Homo sapiens
<220> FEATURE:
<223> OTHER INFORMATION: Homo sapiens SMARCA4 isoform 3 Protein

<400> SEQUENCE: 6

```
Met Ser Thr Pro Asp Pro Pro Leu Gly Gly Thr Pro Arg Pro Gly Pro
1               5                   10                  15

Ser Pro Gly Pro Gly Pro Ser Pro Gly Ala Met Leu Gly Pro Ser Pro
            20                  25                  30

Gly Pro Ser Pro Gly Ser Ala His Ser Met Met Gly Pro Ser Pro Gly
        35                  40                  45

Pro Pro Ser Ala Gly His Pro Ile Pro Thr Gln Gly Pro Gly Gly Tyr
    50                  55                  60

Pro Gln Asp Asn Met His Gln Met His Lys Pro Met Glu Ser Met His
65                  70                  75                  80

Glu Lys Gly Met Ser Asp Asp Pro Arg Tyr Asn Gln Met Lys Gly Met
                85                  90                  95

Gly Met Arg Ser Gly Gly His Ala Gly Met Gly Pro Pro Pro Ser Pro
            100                 105                 110

Met Asp Gln His Ser Gln Gly Tyr Pro Ser Pro Leu Gly Gly Ser Glu
        115                 120                 125

His Ala Ser Ser Pro Val Pro Ala Ser Gly Pro Ser Ser Gly Pro Gln
    130                 135                 140

Met Ser Ser Gly Pro Gly Gly Ala Pro Leu Asp Gly Ala Asp Pro Gln
145                 150                 155                 160

Ala Leu Gly Gln Gln Asn Arg Gly Pro Thr Pro Phe Asn Gln Asn Gln
                165                 170                 175

Leu His Gln Leu Arg Ala Gln Ile Met Ala Tyr Lys Met Leu Ala Arg
            180                 185                 190

Gly Gln Pro Leu Pro Asp His Leu Gln Met Ala Val Gln Gly Lys Arg
        195                 200                 205

Pro Met Pro Gly Met Gln Gln Gln Met Pro Thr Leu Pro Pro Pro Ser
    210                 215                 220

Val Ser Ala Thr Gly Pro Gly Pro Gly Pro Gly Pro Gly Pro Gly Pro
225                 230                 235                 240

Gly Pro Gly Pro Ala Pro Pro Asn Tyr Ser Arg Pro His Gly Met Gly
                245                 250                 255

Gly Pro Asn Met Pro Pro Gly Pro Ser Gly Val Pro Pro Gly Met Pro
            260                 265                 270

Gly Gln Pro Pro Gly Gly Pro Pro Lys Pro Trp Pro Glu Gly Pro
        275                 280                 285

Met Ala Asn Ala Ala Ala Pro Thr Ser Thr Pro Gln Lys Leu Ile Pro
    290                 295                 300
```

```
Pro Gln Pro Thr Gly Arg Pro Ser Pro Ala Pro Ala Val Pro Pro
305                 310                 315                 320

Ala Ala Ser Pro Val Met Pro Pro Gln Thr Gln Ser Pro Gly Gln Pro
            325                 330                 335

Ala Gln Pro Ala Pro Met Val Pro Leu His Gln Lys Gln Ser Arg Ile
        340                 345                 350

Thr Pro Ile Gln Lys Pro Arg Gly Leu Asp Pro Val Glu Ile Leu Gln
    355                 360                 365

Glu Arg Glu Tyr Arg Leu Gln Ala Arg Ile Ala His Arg Ile Gln Glu
    370                 375                 380

Leu Glu Asn Leu Pro Gly Ser Leu Ala Gly Asp Leu Arg Thr Lys Ala
385                 390                 395                 400

Thr Ile Glu Leu Lys Ala Leu Arg Leu Leu Asn Phe Gln Arg Gln Leu
            405                 410                 415

Arg Gln Glu Val Val Cys Met Arg Arg Asp Thr Ala Leu Glu Thr
        420                 425                 430

Ala Leu Asn Ala Lys Ala Tyr Lys Arg Ser Lys Arg Gln Ser Leu Arg
            435                 440                 445

Glu Ala Arg Ile Thr Glu Lys Leu Glu Lys Gln Gln Lys Ile Glu Gln
450                 455                 460

Glu Arg Lys Arg Arg Gln Lys His Gln Glu Tyr Leu Asn Ser Ile Leu
465                 470                 475                 480

Gln His Ala Lys Asp Phe Lys Glu Tyr His Arg Ser Val Thr Gly Lys
            485                 490                 495

Ile Gln Lys Leu Thr Lys Ala Val Ala Thr Tyr His Ala Asn Thr Glu
            500                 505                 510

Arg Glu Gln Lys Lys Glu Asn Glu Arg Ile Glu Lys Glu Arg Met Arg
        515                 520                 525

Arg Leu Met Ala Glu Asp Glu Glu Gly Tyr Arg Lys Leu Ile Asp Gln
530                 535                 540

Lys Lys Asp Lys Arg Leu Ala Tyr Leu Leu Gln Gln Thr Asp Glu Tyr
545                 550                 555                 560

Val Ala Asn Leu Thr Glu Leu Val Arg Gln His Lys Ala Ala Gln Val
            565                 570                 575

Ala Lys Glu Lys Lys Lys Lys Lys Lys Lys Lys Ala Glu Asn Ala
        580                 585                 590

Glu Gly Gln Thr Pro Ala Ile Gly Pro Asp Gly Glu Pro Leu Asp Glu
            595                 600                 605

Thr Ser Gln Met Ser Asp Leu Pro Val Lys Val Ile His Val Glu Ser
610                 615                 620

Gly Lys Ile Leu Thr Gly Thr Asp Ala Pro Lys Ala Gly Gln Leu Glu
625                 630                 635                 640

Ala Trp Leu Glu Met Asn Pro Gly Tyr Glu Val Ala Pro Arg Ser Asp
            645                 650                 655

Ser Glu Glu Ser Gly Ser Glu Glu Glu Glu Glu Glu Glu Glu Glu
            660                 665                 670

Gln Pro Gln Ala Ala Gln Pro Pro Thr Leu Pro Val Glu Glu Lys Lys
        675                 680                 685

Lys Ile Pro Asp Pro Asp Ser Asp Asp Val Ser Glu Val Asp Ala Arg
    690                 695                 700

His Ile Ile Glu Asn Ala Lys Gln Asp Val Asp Asp Glu Tyr Gly Val
705                 710                 715                 720
```

```
Ser Gln Ala Leu Ala Arg Gly Leu Gln Ser Tyr Tyr Ala Val Ala His
            725                 730                 735
Ala Val Thr Glu Arg Val Asp Lys Gln Ser Ala Leu Met Val Asn Gly
            740                 745                 750
Val Leu Lys Gln Tyr Gln Ile Lys Gly Leu Glu Trp Leu Val Ser Leu
            755                 760                 765
Tyr Asn Asn Asn Leu Asn Gly Ile Leu Ala Asp Glu Met Gly Leu Gly
            770                 775             780
Lys Thr Ile Gln Thr Ile Ala Leu Ile Thr Tyr Leu Met Glu His Lys
785                 790                 795                 800
Arg Ile Asn Gly Pro Phe Leu Ile Ile Val Pro Leu Ser Thr Leu Ser
            805                 810                 815
Asn Trp Ala Tyr Glu Phe Asp Lys Trp Ala Pro Ser Val Val Lys Val
            820                 825                 830
Ser Tyr Lys Gly Ser Pro Ala Ala Arg Arg Ala Phe Val Pro Gln Leu
            835                 840                 845
Arg Ser Gly Lys Phe Asn Val Leu Leu Thr Thr Tyr Glu Tyr Ile Ile
            850                 855                 860
Lys Asp Lys His Ile Leu Ala Lys Ile Arg Trp Lys Tyr Met Ile Val
865                 870                 875                 880
Asp Glu Gly His Arg Met Lys Asn His His Cys Lys Leu Thr Gln Val
            885                 890                 895
Leu Asn Thr His Tyr Val Ala Pro Arg Arg Leu Leu Leu Thr Gly Thr
            900                 905                 910
Pro Leu Gln Asn Lys Leu Pro Glu Leu Trp Ala Leu Leu Asn Phe Leu
            915                 920                 925
Leu Pro Thr Ile Phe Lys Ser Cys Ser Thr Phe Glu Gln Trp Phe Asn
            930                 935                 940
Ala Pro Phe Ala Met Thr Gly Glu Lys Val Asp Leu Asn Glu Glu Glu
945                 950                 955                 960
Thr Ile Leu Ile Ile Arg Arg Leu His Lys Val Leu Arg Pro Phe Leu
            965                 970                 975
Leu Arg Arg Leu Lys Lys Glu Val Glu Ala Gln Leu Pro Glu Lys Val
            980                 985                 990
Glu Tyr Val Ile Lys Cys Asp Met  Ser Ala Leu Gln Arg  Val Leu Tyr
            995                 1000                1005
Arg His  Met Gln Ala Lys Gly  Val Leu Leu Thr Asp  Gly Ser Glu
            1010                1015                1020
Lys Asp  Lys Lys Gly Lys Gly  Gly Thr Lys Thr Leu  Met Asn Thr
            1025                1030                1035
Ile Met  Gln Leu Arg Lys Ile  Cys Asn His Pro Tyr  Met Phe Gln
            1040                1045                1050
His Ile  Glu Glu Ser Phe Ser  Glu His Leu Gly Phe  Thr Gly Gly
            1055                1060                1065
Ile Val  Gln Gly Leu Asp Leu  Tyr Arg Ala Ser Gly  Lys Phe Glu
            1070                1075                1080
Leu Leu  Asp Arg Ile Leu Pro  Lys Leu Arg Ala Thr  Asn His Lys
            1085                1090                1095
Val Leu  Leu Phe Cys Gln Met  Thr Ser Leu Met Thr  Ile Met Glu
            1100                1105                1110
Asp Tyr  Phe Ala Tyr Arg Gly  Phe Lys Tyr Leu Arg  Leu Asp Gly
            1115                1120                1125
```

```
Thr Thr Lys Ala Glu Asp Arg Gly Met Leu Leu Lys Thr Phe Asn
1130                1135                1140

Glu Pro Gly Ser Glu Tyr Phe Ile Phe Leu Leu Ser Thr Arg Ala
1145                1150                1155

Gly Gly Leu Gly Leu Asn Leu Gln Ser Ala Asp Thr Val Ile Ile
1160                1165                1170

Phe Asp Ser Asp Trp Asn Pro His Gln Asp Leu Gln Ala Gln Asp
1175                1180                1185

Arg Ala His Arg Ile Gly Gln Asn Glu Val Arg Val Leu Arg
1190                1195                1200

Leu Cys Thr Val Asn Ser Val Glu Glu Lys Ile Leu Ala Ala Ala
1205                1210                1215

Lys Tyr Lys Leu Asn Val Asp Gln Lys Val Ile Gln Ala Gly Met
1220                1225                1230

Phe Asp Gln Lys Ser Ser Ser His Glu Arg Arg Ala Phe Leu Gln
1235                1240                1245

Ala Ile Leu Glu His Glu Glu Gln Asp Glu Glu Glu Asp Glu Val
1250                1255                1260

Pro Asp Asp Glu Thr Val Asn Gln Met Ile Ala Arg His Glu Glu
1265                1270                1275

Glu Phe Asp Leu Phe Met Arg Met Asp Leu Asp Arg Arg Arg Glu
1280                1285                1290

Glu Ala Arg Asn Pro Lys Arg Lys Pro Arg Leu Met Glu Glu Asp
1295                1300                1305

Glu Leu Pro Ser Trp Ile Ile Lys Asp Asp Ala Glu Val Glu Arg
1310                1315                1320

Leu Thr Cys Glu Glu Glu Glu Lys Met Phe Gly Arg Gly Ser
1325                1330                1335

Arg His Arg Lys Glu Val Asp Tyr Ser Asp Ser Leu Thr Glu Lys
1340                1345                1350

Gln Trp Leu Lys Ala Ile Glu Glu Gly Thr Leu Glu Glu Ile Glu
1355                1360                1365

Glu Glu Val Arg Gln Lys Lys Ser Ser Arg Lys Arg Lys Arg Asp
1370                1375                1380

Ser Asp Ala Gly Ser Ser Thr Pro Thr Thr Ser Thr Arg Ser Arg
1385                1390                1395

Asp Lys Asp Asp Glu Ser Lys Lys Gln Lys Lys Arg Gly Arg Pro
1400                1405                1410

Pro Ala Glu Lys Leu Ser Pro Asn Pro Pro Asn Leu Thr Lys Lys
1415                1420                1425

Met Lys Lys Ile Val Asp Ala Val Ile Lys Tyr Lys Asp Ser Ser
1430                1435                1440

Gly Arg Gln Leu Ser Glu Val Phe Ile Gln Leu Pro Ser Arg Lys
1445                1450                1455

Glu Leu Pro Glu Tyr Tyr Glu Leu Ile Arg Lys Pro Val Asp Phe
1460                1465                1470

Lys Lys Ile Lys Glu Arg Ile Arg Asn His Lys Tyr Arg Ser Leu
1475                1480                1485

Asn Asp Leu Glu Lys Asp Val Met Leu Leu Cys Gln Asn Ala Gln
1490                1495                1500

Thr Phe Asn Leu Glu Gly Ser Leu Ile Tyr Glu Asp Ser Ile Val
1505                1510                1515
```

| | | | | | | | | | | | |
|---|---|---|---|---|---|---|---|---|---|---|---|
| Leu | Gln | Ser | Val | Phe | Thr | Ser | Val | Arg | Gln | Lys | Ile | Glu | Lys | Glu |
| | 1520 | | | | 1525 | | | | 1530 | | |

Asp Asp Ser Glu Gly Glu Glu Ser Glu Glu Glu Glu Gly Glu
    1535                            1540                              1545

Glu Glu Gly Ser Glu Ser Glu Ser Arg Ser Val Lys Val Lys Ile
    1550                            1555                        1560

Lys Leu Gly Arg Lys Glu Lys Ala Gln Asp Arg Leu Lys Gly Gly
    1565                            1570                        1575

Arg Arg Arg Pro Ser Arg Gly Ser Arg Ala Lys Pro Val Val Ser
    1580                            1585                        1590

Asp Asp Asp Ser Glu Glu Glu Gln Glu Glu Asp Arg Ser Gly Ser
    1595                            1600                        1605

Gly Ser Glu Glu Asp
    1610

<210> SEQ ID NO 7
<211> LENGTH: 4851
<212> TYPE: DNA
<213> ORGANISM: Homo sapiens
<220> FEATURE:
<223> OTHER INFORMATION: Homo sapiens SMARCA4 isoform 4 mRNA

<400> SEQUENCE: 7

| | |
|---|---|
| atgtccactc cagacccacc cctgggcgga actcctcggc caggtccttc cccgggccct | 60 |
| ggcccttccc ctggagccat gctgggccct agcccgggtc cctcgccggg ctccgcccac | 120 |
| agcatgatgg ggcccagccc agggccgccc tcagcaggac accccatccc acccagggg | 180 |
| cctggagggt accctcagga caacatgcac cagatgcaca gcccatgga gtccatgcat | 240 |
| gagaagggca tgtcggacga cccgcgctac aaccagatga aggaatggg gatgcggtca | 300 |
| ggggccatg ctgggatggg gccccgccc agcccatgg accagcactc ccaaggttac | 360 |
| ccctcgcccc tgggtggctc tgagcatgcc tctagtccag ttccagccag tggcccgtct | 420 |
| tcggggcccc agatgtcttc cgggccagga ggtgccccgc tggatggtgc tgacccccag | 480 |
| gccttgggc agcagaaccg ggcccaacc ccatttaacc agaaccagct gcaccagctc | 540 |
| agagctcaga tcatggccta caagatgctg gccaggggc agcccctccc cgaccacctg | 600 |
| cagatggcgg tgcagggcaa gcggccgatg cccgggatgc agcagcagat gccaacgcta | 660 |
| cctccaccct cggtgtccgc aacaggaccc ggccctggcc ctggccctgg ccccggcccg | 720 |
| ggtcccggcc cggcacctcc aaattacagc aggcctcatg gtatgggagg gcccaacatg | 780 |
| cctccccag accctcggg cgtgcccccc gggatgccag gccagcctcc tggagggcct | 840 |
| cccaagccct ggcctgaagg acccatggcg aatgctgctg cccccacgag cacccctcag | 900 |
| aagctgattc cccgcagcc aacgggccgc ccttccccg cgcccctgc cgtcccaccc | 960 |
| gccgcctcgc ccgtgatgcc accgcagacc cagtccccg gcagccggc ccagcccgcg | 1020 |
| cccatggtgc cactgcacca gaagcagagc cgcatcaccc ccatccagaa gccgcgggc | 1080 |
| ctcgaccctg tggagatcct gcaggagcgc gagtacaggc tgcaggctcg catcgcacac | 1140 |
| cgaattcagg aacttgaaaa ccttccgggg tccctggccg gggatttgcg aaccaaagcg | 1200 |
| accattgagc tcaaggccct caggctgctg aacttccaga ggcagctgcg ccaggaggtg | 1260 |
| gtggtgtgca tgcggaggga cacagcgctg gagacagccc tcaatgctaa ggcctacaag | 1320 |
| cgcagcaagc gccagtccct gcgcgaggcc cgcatcactg agaagctgga gaagcagcag | 1380 |
| aagatcgagc aggagcgcaa gcgccggcag aagcaccagg aatacctcaa tagcattctc | 1440 |

-continued

```
cagcatgcca aggatttcaa ggaatatcac agatccgtca caggcaaaat ccagaagctg   1500
accaaggcag tggccacgta ccatgccaac acggagcggg agcagaagaa agagaacgag   1560
cggatcgaga aggagcgcat gcggaggctc atggctgaag atgaggaggg gtaccgcaag   1620
ctcatcgacc agaagaagga caagcgcctg gcctacctct gcagcagac agacgagtac    1680 gtggctaacc tcacggagct ggtgcggcag cacaaggctg cccaggtcgc caaggagaaa   1740
aagaagaaaa agaaaaagaa gaaggcagaa aatgcagaag acagacgcc tgccattggg    1800 ccggatggcg agcctctgga cgagaccagc cagatgagcg acctcccggt gaaggtgatc   1860
cacgtggaga gtgggaagat cctcacaggc acagatgccc ccaaagccgg gcagctggag   1920
gcctggctcg agatgaaccc ggggtatgaa gtagctccga ggtctgatag tgaagaaagt   1980
ggctcagaag aagaggaaga ggaggaggag gaagagcagc cgcaggcagc acagcctccc   2040
accctgcccg tggaggagaa gaagaagatt ccagatccag acagcgatga cgtctctgag   2100
gtggacgcgc ggcacatcat tgagaatgcc aagcaagatg tcgatgatga atatggcgtg   2160
tcccaggccc ttgcacgtgg cctgcagtcc tactatccg tggcccatgc tgtcactgag    2220
agagtggaca gcagtcagc gcttatggtc aatggtgtcc tcaaacagta ccagatcaaa   2280
ggtttggagt ggctggtgtc cctgtacaac aacaacctga acggcatcct ggccgacgag   2340
atgggcctgg ggaagaccat ccagaccatc gcgctcatca cgtacctcat ggagcacaaa   2400
cgcatcaatg gcccttcct catcatcgtg cctctctcaa cgctgtccaa ctgggcgtac    2460
gagtttgaca gtgggcccc ctccgtggtg aaggtgtctt acaagggatc cccagcagca    2520
agacgggcct ttgtccccca gctccggagt gggaagttca acgtcttgct gacgacgtac   2580
gagtacatca tcaaagacaa gcacatcctc gccaagatcc gttggaagta catgattgtg   2640
gacgaaggtc accgcatgaa gaaccaccac tgcaagctga cgcaggtgct caacacgcac   2700
tatgtggcac ccgccgcct gctgctgacg gcacaccgc tgcagaacaa gcttcccgag    2760
ctctgggcgc tgctcaactt cctgctgccc accatcttca agagctgcag caccttcgag   2820
cagtggttta acgcaccctt tgccatgacc ggggaaaagg tggacctgaa tgaggaggaa   2880
accattctca tcatccggcg tctccacaaa gtgctgcggc ccttcttgct ccgacgactc   2940
aagaaggaag tcgaggccca gttgcccgaa aaggtggagt acgtcatcaa gtgcgacatg   3000
tctgcgctgc agcgagtgct ctaccgccac atgcaggcca agggcgtgct gctgactgat   3060
ggctccgaga aggacaagaa gggcaaaggc ggcaccaaga ccctgatgaa caccatcatg   3120
cagctgcgga agatctgcaa ccacccctac atgttccagc acatcgagga gtccttttcc   3180
gagcacttgg ggttcactgg cggcattgtc caagggctgg acctgtaccg agcctcgggt   3240
aaatttgagc ttcttgatag aattcttccc aaactccgag caaccaacca caaagtgctg   3300
ctgttctgcc aaatgaccct cctcatgacc atcatggaag attactttgc gtatcgcggc   3360
tttaaatacc tcaggcttga tggaaccacg aaggcggagg accgggcat gctgctgaaa    3420 accttcaacg agcccggctc tgagtacttc atcttcctgc tcagcacccg ggctgggggg   3480
ctcggcctga acctccagtc ggcagacact gtgatcattt ttgacagcga ctggaatcct   3540
caccaggacc tgcaagcgca ggaccgagcc accgcatcg gcagcagaa cgaggtgcgt   3600 gtgctccgcc tctgcaccgt caacagcgtg gaggagaaga tcctagctgc agccaagtac   3660
aagctcaacg tggaccagaa ggtgatccag gccggcatgt tcgaccagaa gtcctccagc   3720
catgagcggc gcgccttcct gcaggccatc ctggagcacg aggagcagga tgaggaggaa   3780
gacgaggtgc ccgacgacga gaccgtcaac cagatgatcg cccggcacga ggaggagttt   3840
```

-continued

```
gatctgttca tgcgcatgga cctggaccgc aggcgcgagg aggcccgcaa ccccaagcgg   3900
aagccgcgcc tcatggagga ggacgagctc ccctcgtgga tcatcaagga cgacgcggag   3960
gtggagcggc tgacctgtga ggaggaggag gagaagatgt tcggccgtgg ctcccgccac   4020
cgcaaggagg tggactacag cgactcactg acggagaagc agtggctcaa gaccctgaag   4080
gccatcgagg agggcacgct ggaggagatc gaagaggagg tccggcagaa gaaatcatca   4140
cggaagcgca gcgagacag cgacgccggc tcctccaccc cgaccaccag cacccgcagc   4200
cgcgacaagg acgacgagag caagaagcag aagaagcgcg gcggccgcc tgccgagaaa   4260 ctctccccta accccaccaa cctcaccaag aagatgaaga agattgtgga tgccgtgatc   4320
aagtacaagg acagcagtgg acgtcagctc agcgaggtct tcatccagct gcctcgcga   4380 aaggagctgc ccgagtacta cgagctcatc cgcaagcccg tggacttcaa gaagataaag   4440
gagcgcattc gcaaccacaa gtaccgcagc ctcaacgacc tagagaagga cgtcatgctc   4500
ctgtgccaga acgcacagac cttcaacctg gagggctccc tgatctatga agactccatc   4560
gtcttgcagt cggtcttcac cagcgtgcgg cagaaaatcg agaaggagga tgacagtgaa   4620
ggcgaggaga gtgaggagga ggaagagggc gaggaggaag ctccgaatc cgaatctcgg   4680 tccgtcaaag tgaagatcaa gcttggccgg aaggagaagg cacaggaccg gctgaagggc   4740
ggccggcggc ggcccgagcc agggtcccga gccaagccgg tcgtgagtga cgatgacagt   4800
gaggaggaac aagaggagga ccgctcagga agtggcagcg aagaagactg a           4851
```

<210> SEQ ID NO 8
<211> LENGTH: 1616
<212> TYPE: PRT
<213> ORGANISM: Homo sapiens
<220> FEATURE:
<223> OTHER INFORMATION: Homo sapiens SMARCA4 isoform 4 Protein

<400> SEQUENCE: 8

```
Met Ser Thr Pro Asp Pro Pro Leu Gly Gly Thr Pro Arg Pro Gly Pro
 1               5                  10                  15

Ser Pro Gly Pro Gly Pro Ser Pro Gly Ala Met Leu Gly Pro Ser Pro
            20                  25                  30

Gly Pro Ser Pro Gly Ser Ala His Ser Met Met Gly Pro Ser Pro Gly
        35                  40                  45

Pro Pro Ser Ala Gly His Pro Ile Pro Thr Gln Gly Pro Gly Gly Tyr
    50                  55                  60

Pro Gln Asp Asn Met His Gln Met His Lys Pro Met Glu Ser Met His
65                  70                  75                  80

Glu Lys Gly Met Ser Asp Asp Pro Arg Tyr Asn Gln Met Lys Gly Met
                85                  90                  95

Gly Met Arg Ser Gly Gly His Ala Gly Met Gly Pro Pro Pro Ser Pro
            100                 105                 110

Met Asp Gln His Ser Gln Gly Tyr Pro Ser Pro Leu Gly Gly Ser Glu
        115                 120                 125

His Ala Ser Ser Pro Val Pro Ala Ser Gly Pro Ser Ser Gly Pro Gln
    130                 135                 140

Met Ser Ser Gly Pro Gly Gly Ala Pro Leu Asp Gly Ala Asp Pro Gln
145                 150                 155                 160

Ala Leu Gly Gln Gln Asn Arg Gly Pro Thr Pro Phe Asn Gln Asn Gln
                165                 170                 175

Leu His Gln Leu Arg Ala Gln Ile Met Ala Tyr Lys Met Leu Ala Arg
            180                 185                 190
```

```
Gly Gln Pro Leu Pro Asp His Leu Gln Met Ala Val Gln Gly Lys Arg
            195                 200                 205
Pro Met Pro Gly Met Gln Gln Met Pro Thr Leu Pro Pro Pro Ser
210             215                 220
Val Ser Ala Thr Gly Pro Gly Pro Gly Pro Gly Pro Gly Pro Gly Pro
225             230                 235                 240
Gly Pro Gly Pro Ala Pro Pro Asn Tyr Ser Arg Pro His Gly Met Gly
                245                 250                 255
Gly Pro Asn Met Pro Pro Pro Gly Pro Ser Gly Val Pro Pro Gly Met
            260                 265                 270
Pro Gly Gln Pro Pro Gly Gly Pro Pro Lys Pro Trp Pro Glu Gly Pro
            275                 280                 285
Met Ala Asn Ala Ala Ala Pro Thr Ser Thr Pro Gln Lys Leu Ile Pro
290                 295                 300
Pro Gln Pro Thr Gly Arg Pro Ser Pro Ala Pro Pro Ala Val Pro Pro
305                 310                 315                 320
Ala Ala Ser Pro Val Met Pro Pro Gln Thr Gln Ser Pro Gly Gln Pro
                325                 330                 335
Ala Gln Pro Ala Pro Met Val Pro Leu His Gln Lys Gln Ser Arg Ile
            340                 345                 350
Thr Pro Ile Gln Lys Pro Arg Gly Leu Asp Pro Val Glu Ile Leu Gln
            355                 360                 365
Glu Arg Glu Tyr Arg Leu Gln Ala Arg Ile Ala His Arg Ile Gln Glu
            370                 375                 380
Leu Glu Asn Leu Pro Gly Ser Leu Ala Gly Asp Leu Arg Thr Lys Ala
385                 390                 395                 400
Thr Ile Glu Leu Lys Ala Leu Arg Leu Leu Asn Phe Gln Arg Gln Leu
                405                 410                 415
Arg Gln Glu Val Val Val Cys Met Arg Arg Asp Thr Ala Leu Glu Thr
            420                 425                 430
Ala Leu Asn Ala Lys Ala Tyr Lys Arg Ser Lys Arg Gln Ser Leu Arg
            435                 440                 445
Glu Ala Arg Ile Thr Glu Lys Leu Glu Lys Gln Gln Lys Ile Glu Gln
            450                 455                 460
Glu Arg Lys Arg Arg Gln Lys His Gln Glu Tyr Leu Asn Ser Ile Leu
465                 470                 475                 480
Gln His Ala Lys Asp Phe Lys Glu Tyr His Arg Ser Val Thr Gly Lys
                485                 490                 495
Ile Gln Lys Leu Thr Lys Ala Val Ala Thr Tyr His Ala Asn Thr Glu
            500                 505                 510
Arg Glu Gln Lys Lys Glu Asn Glu Arg Ile Glu Lys Glu Arg Met Arg
            515                 520                 525
Arg Leu Met Ala Glu Asp Glu Glu Gly Tyr Arg Lys Leu Ile Asp Gln
            530                 535                 540
Lys Lys Asp Lys Arg Leu Ala Tyr Leu Leu Gln Gln Thr Asp Glu Tyr
545                 550                 555                 560
Val Ala Asn Leu Thr Glu Leu Val Arg Gln His Lys Ala Ala Gln Val
                565                 570                 575
Ala Lys Glu Lys Lys Lys Lys Lys Lys Lys Lys Ala Glu Asn Ala
            580                 585                 590
Glu Gly Gln Thr Pro Ala Ile Gly Pro Asp Gly Glu Pro Leu Asp Glu
            595                 600                 605
```

-continued

```
Thr Ser Gln Met Ser Asp Leu Pro Val Lys Val Ile His Val Glu Ser
    610                 615                 620
Gly Lys Ile Leu Thr Gly Thr Asp Ala Pro Lys Ala Gly Gln Leu Glu
625                 630                 635                 640
Ala Trp Leu Glu Met Asn Pro Gly Tyr Glu Val Ala Pro Arg Ser Asp
                645                 650                 655
Ser Glu Glu Ser Gly Ser Glu Glu Glu Glu Glu Glu Glu Glu Glu Glu
                660                 665                 670
Gln Pro Gln Ala Ala Gln Pro Pro Thr Leu Pro Val Glu Glu Lys Lys
                675                 680                 685
Lys Ile Pro Asp Pro Asp Ser Asp Asp Val Ser Glu Val Asp Ala Arg
690                 695                 700
His Ile Ile Glu Asn Ala Lys Gln Asp Val Asp Asp Glu Tyr Gly Val
705                 710                 715                 720
Ser Gln Ala Leu Ala Arg Gly Leu Gln Ser Tyr Tyr Ala Val Ala His
                725                 730                 735
Ala Val Thr Glu Arg Val Asp Lys Gln Ser Ala Leu Met Val Asn Gly
                740                 745                 750
Val Leu Lys Gln Tyr Gln Ile Lys Gly Leu Glu Trp Leu Val Ser Leu
                755                 760                 765
Tyr Asn Asn Asn Leu Asn Gly Ile Leu Ala Asp Glu Met Gly Leu Gly
                770                 775                 780
Lys Thr Ile Gln Thr Ile Ala Leu Ile Thr Tyr Leu Met Glu His Lys
785                 790                 795                 800
Arg Ile Asn Gly Pro Phe Leu Ile Ile Val Pro Leu Ser Thr Leu Ser
                805                 810                 815
Asn Trp Ala Tyr Glu Phe Asp Lys Trp Ala Pro Ser Val Val Lys Val
                820                 825                 830
Ser Tyr Lys Gly Ser Pro Ala Ala Arg Arg Ala Phe Val Pro Gln Leu
                835                 840                 845
Arg Ser Gly Lys Phe Asn Val Leu Leu Thr Thr Tyr Glu Tyr Ile Ile
850                 855                 860
Lys Asp Lys His Ile Leu Ala Lys Ile Arg Trp Lys Tyr Met Ile Val
865                 870                 875                 880
Asp Glu Gly His Arg Met Lys Asn His His Cys Lys Leu Thr Gln Val
                885                 890                 895
Leu Asn Thr His Tyr Val Ala Pro Arg Arg Leu Leu Leu Thr Gly Thr
                900                 905                 910
Pro Leu Gln Asn Lys Leu Pro Glu Leu Trp Ala Leu Leu Asn Phe Leu
                915                 920                 925
Leu Pro Thr Ile Phe Lys Ser Cys Ser Thr Phe Glu Gln Trp Phe Asn
                930                 935                 940
Ala Pro Phe Ala Met Thr Gly Glu Lys Val Asp Leu Asn Glu Glu
945                 950                 955                 960
Thr Ile Leu Ile Ile Arg Arg Leu His Lys Val Leu Arg Pro Phe Leu
                965                 970                 975
Leu Arg Arg Leu Lys Lys Glu Val Glu Ala Gln Leu Pro Glu Lys Val
                980                 985                 990
Glu Tyr Val Ile Lys Cys Asp Met Ser Ala Leu Gln Arg Val Leu Tyr
                995                1000                1005
Arg His Met Gln Ala Lys Gly Val Leu Leu Thr Asp Gly Ser Glu
            1010                1015                1020
```

```
Lys Asp Lys Lys Gly Lys Gly Gly Thr Lys Thr Leu Met Asn Thr
1025                1030                1035

Ile Met Gln Leu Arg Lys Ile Cys Asn His Pro Tyr Met Phe Gln
1040                1045                1050

His Ile Glu Glu Ser Phe Ser Glu His Leu Gly Phe Thr Gly Gly
1055                1060                1065

Ile Val Gln Gly Leu Asp Leu Tyr Arg Ala Ser Gly Lys Phe Glu
1070                1075                1080

Leu Leu Asp Arg Ile Leu Pro Lys Leu Arg Ala Thr Asn His Lys
1085                1090                1095

Val Leu Leu Phe Cys Gln Met Thr Ser Leu Met Thr Ile Met Glu
1100                1105                1110

Asp Tyr Phe Ala Tyr Arg Gly Phe Lys Tyr Leu Arg Leu Asp Gly
1115                1120                1125

Thr Thr Lys Ala Glu Asp Arg Gly Met Leu Leu Lys Thr Phe Asn
1130                1135                1140

Glu Pro Gly Ser Glu Tyr Phe Ile Phe Leu Leu Ser Thr Arg Ala
1145                1150                1155

Gly Gly Leu Gly Leu Asn Leu Gln Ser Ala Asp Thr Val Ile Ile
1160                1165                1170

Phe Asp Ser Asp Trp Asn Pro His Gln Asp Leu Gln Ala Gln Asp
1175                1180                1185

Arg Ala His Arg Ile Gly Gln Gln Asn Glu Val Arg Val Leu Arg
1190                1195                1200

Leu Cys Thr Val Asn Ser Val Glu Glu Lys Ile Leu Ala Ala Ala
1205                1210                1215

Lys Tyr Lys Leu Asn Val Asp Gln Lys Val Ile Gln Ala Gly Met
1220                1225                1230

Phe Asp Gln Lys Ser Ser Ser His Glu Arg Arg Ala Phe Leu Gln
1235                1240                1245

Ala Ile Leu Glu His Glu Glu Gln Asp Glu Glu Glu Asp Glu Val
1250                1255                1260

Pro Asp Asp Glu Thr Val Asn Gln Met Ile Ala Arg His Glu Glu
1265                1270                1275

Glu Phe Asp Leu Phe Met Arg Met Asp Leu Asp Arg Arg Arg Glu
1280                1285                1290

Glu Ala Arg Asn Pro Lys Arg Lys Pro Arg Leu Met Glu Glu Asp
1295                1300                1305

Glu Leu Pro Ser Trp Ile Ile Lys Asp Asp Ala Glu Val Glu Arg
1310                1315                1320

Leu Thr Cys Glu Glu Glu Glu Lys Met Phe Gly Arg Gly Ser
1325                1330                1335

Arg His Arg Lys Glu Val Asp Tyr Ser Asp Ser Leu Thr Glu Lys
1340                1345                1350

Gln Trp Leu Lys Thr Leu Lys Ala Ile Glu Glu Gly Thr Leu Glu
1355                1360                1365

Glu Ile Glu Glu Glu Val Arg Gln Lys Lys Ser Ser Arg Lys Arg
1370                1375                1380

Lys Arg Asp Ser Asp Ala Gly Ser Ser Thr Pro Thr Thr Ser Thr
1385                1390                1395

Arg Ser Arg Asp Lys Asp Asp Glu Ser Lys Lys Gln Lys Lys Arg
1400                1405                1410
```

Gly Arg Pro Pro Ala Glu Lys Leu Ser Pro Asn Pro Pro Asn Leu
1415                1420                1425

Thr Lys Lys Met Lys Lys Ile Val Asp Ala Val Ile Lys Tyr Lys
1430                1435                1440

Asp Ser Ser Gly Arg Gln Leu Ser Glu Val Phe Ile Gln Leu Pro
1445                1450                1455

Ser Arg Lys Glu Leu Pro Glu Tyr Tyr Glu Leu Ile Arg Lys Pro
1460                1465                1470

Val Asp Phe Lys Lys Ile Lys Glu Arg Ile Arg Asn His Lys Tyr
1475                1480                1485

Arg Ser Leu Asn Asp Leu Glu Lys Asp Val Met Leu Leu Cys Gln
1490                1495                1500

Asn Ala Gln Thr Phe Asn Leu Glu Gly Ser Leu Ile Tyr Glu Asp
1505                1510                1515

Ser Ile Val Leu Gln Ser Val Phe Thr Ser Val Arg Gln Lys Ile
1520                1525                1530

Glu Lys Glu Asp Asp Ser Glu Gly Glu Glu Ser Glu Glu Glu Glu
1535                1540                1545

Glu Gly Glu Glu Gly Ser Glu Ser Glu Ser Arg Ser Val Lys
1550                1555                1560

Val Lys Ile Lys Leu Gly Arg Lys Glu Lys Ala Gln Asp Arg Leu
1565                1570                1575

Lys Gly Gly Arg Arg Pro Ser Arg Gly Ser Arg Ala Lys Pro
1580                1585                1590

Val Val Ser Asp Asp Asp Ser Glu Glu Glu Gln Glu Glu Asp Arg
1595                1600                1605

Ser Gly Ser Gly Ser Glu Glu Asp
1610                1615

<210> SEQ ID NO 9
<211> LENGTH: 13
<212> TYPE: DNA
<213> ORGANISM: Homo sapiens

<400> SEQUENCE: 9
gacgagaccg tca                                                          13

<210> SEQ ID NO 10
<211> LENGTH: 4
<212> TYPE: PRT
<213> ORGANISM: Homo sapiens

<400> SEQUENCE: 10

Glu Thr Val Asn
1

<210> SEQ ID NO 11
<211> LENGTH: 21
<212> TYPE: DNA
<213> ORGANISM: Homo sapiens

<400> SEQUENCE: 11
agtggctcaa ggtacatgct g                                                 21

<210> SEQ ID NO 12
<211> LENGTH: 21
<212> TYPE: DNA
<213> ORGANISM: Homo sapiens

```
<400> SEQUENCE: 12
cagtggctca agatacatgc t                                             21

<210> SEQ ID NO 13
<211> LENGTH: 100
<212> TYPE: DNA
<213> ORGANISM: Homo sapiens

<400> SEQUENCE: 13
gcacaaggct gcccaggtcg ccaaggagaa aaagaagaaa aagaaaaaga aggtgtgctg   60
ggcctggcat ggtgcccgcc gcgggtggga tgggagcagc                        100

<210> SEQ ID NO 14
<211> LENGTH: 31
<212> TYPE: DNA
<213> ORGANISM: Homo sapiens

<400> SEQUENCE: 14
gcacaaggct gcccaggtcg ccaggagcag c                                  31

<210> SEQ ID NO 15
<211> LENGTH: 38
<212> TYPE: DNA
<213> ORGANISM: Homo sapiens

<400> SEQUENCE: 15
aggctgccca ggtcgccagg agcagccgtc ttcacgtc                           38

<210> SEQ ID NO 16
<211> LENGTH: 4
<212> TYPE: PRT
<213> ORGANISM: Homo sapiens

<400> SEQUENCE: 16

Asp Glu Ala Asp
1

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Tyr Ser Phe Thr Thr Thr Ala Glu Arg
1               5                   10
```

COMPOSITIONS AND METHODS FOR THE DIAGNOSIS AND TREATMENT OF OVARIAN CANCERS THAT ARE ASSOCIATED WITH REDUCED SMARCA4 GENE EXPRESSION OR PROTEIN FUNCTION

CROSS REFERENCE TO RELATED APPLICATIONS

This application claims priority to U.S. Provisional Patent Applications No. 61/922,710 filed Dec. 31, 2013 and No. 61/973,759 filed Apr. 1, 2014 the contents of each of which are incorporated by reference herein.

GOVERNMENT SPONSORED RESEARCH OR DEVELOPMENT

This application is a continuation of U.S. patent application Ser. No. 15/109,403, filed Jun. 30, 2016, which is a National Stage Application of PCT/US2014/073077, filed Dec. 31, 2014, which claims the benefit of and priority to U.S. Provisional Patent Application No. 61/922,710, filed Dec. 31, 2013, and U.S. Provisional Patent Application No. 61/973,759, filed Apr. 1, 2014, the entire contents of each of which are incorporated by reference herein.

SEQUENCE LISTING

The present application includes a Sequence Listing in electronic form as a txt file in ASCII format titled 115872-0411 SL.txt created on Apr. 30, 2018, and having a size of 84,100 bytes. The contents of this txt file are incorporated by reference herein.

BACKGROUND OF THE DISCLOSURE

Technical Field

The present disclosure relates, generally, to the diagnosis and treatment of ovarian cancers, such as small cell ovarian cancers, in particular small cell carcinoma of the ovary, hypercalcemic type (SCCOHT), which ovarian cancers are characterized by reduced SMARCA4 gene expression and/or protein function and, as a consequence, are sensitive to growth and/or survival inhibition by one or more compounds that restore SMARCA4 gene expression and/or protein function (such as drugs that target DNA repair pathways) and/or inhibit growth dysregulating and survival promoting consequences of such aberrant SMARCA4 gene expression such as EZH2 hyperactivity.

Description of the Related Art

Small cell carcinoma of the ovary, hypercalcemic type (SCCOHT), is a rare, aggressive form of ovarian cancer diagnosed in young women. SCCOHT is generally fatal when spread beyond the ovary. SCCOHT represents less than 1% of all ovarian cancer diagnoses, with less than 300 cases reported in the literature to date. Estel et al., *Arch Gynecol Obstet* 284:1277-82 (2011) and Young et al., *Am J Surg Pathol* 18:1102-16 (1994). The mean age at diagnosis is 23 years and, unlike patients with the more common types of ovarian cancer, the majority of these women present with early-stage disease. Harrison et al., *Gynecol Oncol* 100: 233-8 (2006). Nonetheless, most patients relapse and die within 2 years of diagnosis, regardless of stage, with a long-term survival rate of only 33%, even when disease is confined to the ovary at diagnosis. Seidman, *Gynecol Oncol* 59:283-7 (1995). There are no reliable adjuvant treatments that improve outcome, but multi-compound chemotherapy is thought to extend survival. Estel et al., *Arch Gynecol Obstet* 284:1277-82 (2011) and Pautier et al., *Ann Oncol* 18:1985-9 (2007).

The tissue of origin remains speculative, and SCCOHT is still categorized as a miscellaneous tumor by the World Health Organization. Most tumors are unilateral, and size greater than 10 cm may be prognostically favorable due to earlier onset of symptoms resulting in stage migration. Estel et al., *Arch Gynecol Obstet* 284:1277-82 (2011). Histologic classification can be challenging, but commonly expressed immunohistochemical markers such as CD10, WT1, and calretinin can be useful in conjunction with loss of detectable inhibin, S100, and chromogranin expression to exclude histological mimics. McCluggage, *Adv Anat Pathol* 11:288-96 (2004).

SUMMARY OF THE DISCLOSURE

The present disclosure is based upon the discovery that mutations in the SMARCA4 gene and/or associated regulatory sequences, including certain germline or somatic mutations, in particular mutations in both alleles of the SMARCA4 gene and/or associated regulatory sequences (i.e., bi-allelic mutations), which reduce or eliminate SMARCA4 gene expression and/or that reduce or eliminate SMARCA4 protein levels and/or protein function, are causally linked to certain cancers, including ovarian cancers, such as small cell carcinomas of the ovary (SCCO), in particular SCCO hypercalcemic type (SCCOHT), which is a rare, highly aggressive form of ovarian cancer.

It was further discovered that restoring SMARCA4 gene expression and/or SMARCA4 protein levels or functionality in SMARCA4-negative cells, in particular in SCCOHT cells, suppresses cell growth while reducing SMARCA4 gene expression and/or SMARCA4 protein levels of functionality in SMARCA4-positive cells promotes cell growth.

Based upon these and other discoveries, which are described in detail herein, in certain embodiments, the present disclosure provides methods for the diagnosis of cancers, including ovarian cancers, such as small cell carcinomas of the ovary (SCCO), in particular SCCO hypercalcemic type (SCCOHT), which cancers are associated with reduced or undetectable SMARCA4 gene expression and/or with reduced or undetectable SMARCA4 protein levels and/or protein function, which methods include the detection of one or more mutations, including one or more germline or somatic mutations, in the SMARCA4 gene and/or associated regulatory sequences in particular mutations in both alleles of the SMARCA4 gene and/or associated regulatory sequences (i.e., bi-allelic mutations), which are known, predicted, or demonstrated to reduce or eliminate SMARCA4 gene expression and/or known, predicted, or demonstrated to reduce or eliminate SMARCA4 protein levels and/or protein function.

In other embodiments, the present disclosure provides methods for inhibiting the growth of cancer cells and for the treatment of cancers, including ovarian cancers, such as small cell carcinomas of the ovary (SCCO), in particular SCCO hypercalcemic type (SCCOHT), which cancers are associated with a cancer cell exhibiting reduced or undetectable SMARCA4 gene expression and/or with reduced or undetectable SMARCA4 protein levels and/or protein function, which methods include contacting a cancer cell with, or administering to a cancer patient, one or more compounds, including one or more polynucleotides, polypeptides, and/or small molecules that can restore SMARCA4 gene expression and/or SMARCA4 protein levels and/or protein function and, thereby, slow or stop the growth of the cancer cell. Alternatively, drugs that target DNA repair pathways and/or inhibit growth dysregulating and survival promoting consequences of such aberrant SMARCA4 gene expression such as EZH2 hyperactivity can be used for treating tumors characterized by reduced or eliminated SMARCA4 expression and/or protein levels or function.

In still further embodiments, the present disclosure provides compounds and compositions, including pharmaceutical compositions, containing those compounds, which compounds and compositions may be advantageously employed in the presently-disclosed methods for inhibiting the growth of cancer cells and for the treatment of cancers, including ovarian cancers, such as small cell carcinomas of the ovary (SCCO), in particular SCCO hypercalcemic type (SCCOHT), which cancers are associated with a cancer cell exhibiting reduced or undetectable SMARCA4 gene expression and/or with reduced or undetectable SMARCA4 protein levels and/or protein function. Exemplified herein are compounds, including polynucleotides, polypeptides, and small molecules that can be used to restore SMARCA4 gene expression and/or function and/or restore SMARCA4 protein level and/or function and, thereby, slow or stop the growth of a cancer cell. Alternatively, drugs that target DNA repair pathways and/or inhibit growth dysregulating and survival promoting consequences of such aberrant SMARCA4 gene expression such as EZH2 hyperactivity can be used for treating tumors characterized by reduced or eliminated SMARCA4 expression and/or protein levels or function. These therapeutic approaches may be combined with chemotherapeutic drugs and more specifically drugs that damage genomic DNA in rapidly dividing cells.

In yet other embodiments, the present disclosure provides diagnostic kits for identifying a cancer cell or for detecting in a patient a cancer cell that exhibits reduced or eliminated SMARCA4 gene expression and/or function and/or reduced or absent SMARCA4 protein level and/or functionality, which diagnostic kits contain one or more reagents that can be used alone or in combination to: (a) detect a mutation in a SMARCA4 gene and/or mRNA, such as an insertion mutation, a deletion mutation, a frame shift mutation, a splice site mutation, and a point mutation, in particular a nonsense mutation and/or a missense mutation in a SMARCA4 gene and/or mRNA; (b) detect a reduction in SMARCA4 mRNA level; (c) detect a reduction in SMARCA4 protein level; and/or (d) detect a reduction in SMARCA4 protein functionality.

Within related aspects, the present disclosure also provides diagnostic kits that can be advantageously employed in the methods of the present disclosure for identifying a cancer cell or a detecting in a patient a cancer cell that exhibits reduced or eliminated SMARCA4 gene expression and/or function and/or reduced or absent SMARCA4 protein level and/or functionality, which diagnostic kits contain one or more agents that can be used alone or in combination to: (a) detect a mutation in a SMARCA4 gene and/or mRNA, such as an insertion mutation, a deletion mutation, a frame shift mutation, a splice site mutation, and a point mutation, in particular nonsense mutation and/or a missense mutation in a SMARCA4 gene and/or mRNA; (b) detect a reduction in SMARCA4 mRNA level; (c) detect a reduction in SMARCA4 protein level; and/or (d) detect a reduction in SMARCA4 protein functionality. Such reagents may include for example amplification primers for all or for one or more portions of the genomic sequence of SMARCA4 and detectable labels as well as positive and negative controls wherein said controls are not substances found in nature.

These and other aspects of the present disclosure will be best understood in conjunction with the following drawings, which exemplify certain aspects of the various embodiments.

BRIEF DESCRIPTION OF THE DRAWINGS

FIG. 3 is a scatterplot with grouped data showing SMARCA4 gene expression across TCGA tumors for cases with available mutation and RNA sequence data (RSEM). A correlation is seen between inactivating SMARCA4 mutations and decreased gene expression across various solid tumors. A two-sample Student's t-test comparing samples with non-missense mutations and other samples without mutations or with only missense mutations. For all TCGA samples, the mean RSEM (2050, std: 1760) was less in samples with non-missense mutations than other samples without mutations or with only missense mutations (3724, std: 1692; $P=8.7 \times 10^{-4}$). For TCGA lung adenocarcinoma samples, the mean RSEM (601, std: 370) was less in samples with non-missense mutations than other samples without mutations or with only missense mutations (3330, std: 1524; $P=2 \times 10^{-8}$).

FIG. 12A is a digital photograph of a western blot confirming SMARCA4 knock-down in SMARCA3 depleted 293T cells. β-Actin was used as a loading control.

FIG. 12B is a plot of tumor volume versus time from xenograft injection and thus depicting tumor growth in mice xenografted with SMARCA4 knock-down in 293T cells (squares) compared to nontargeted control (NTC, diamonds).

DETAILED DESCRIPTION

Figure 1A:
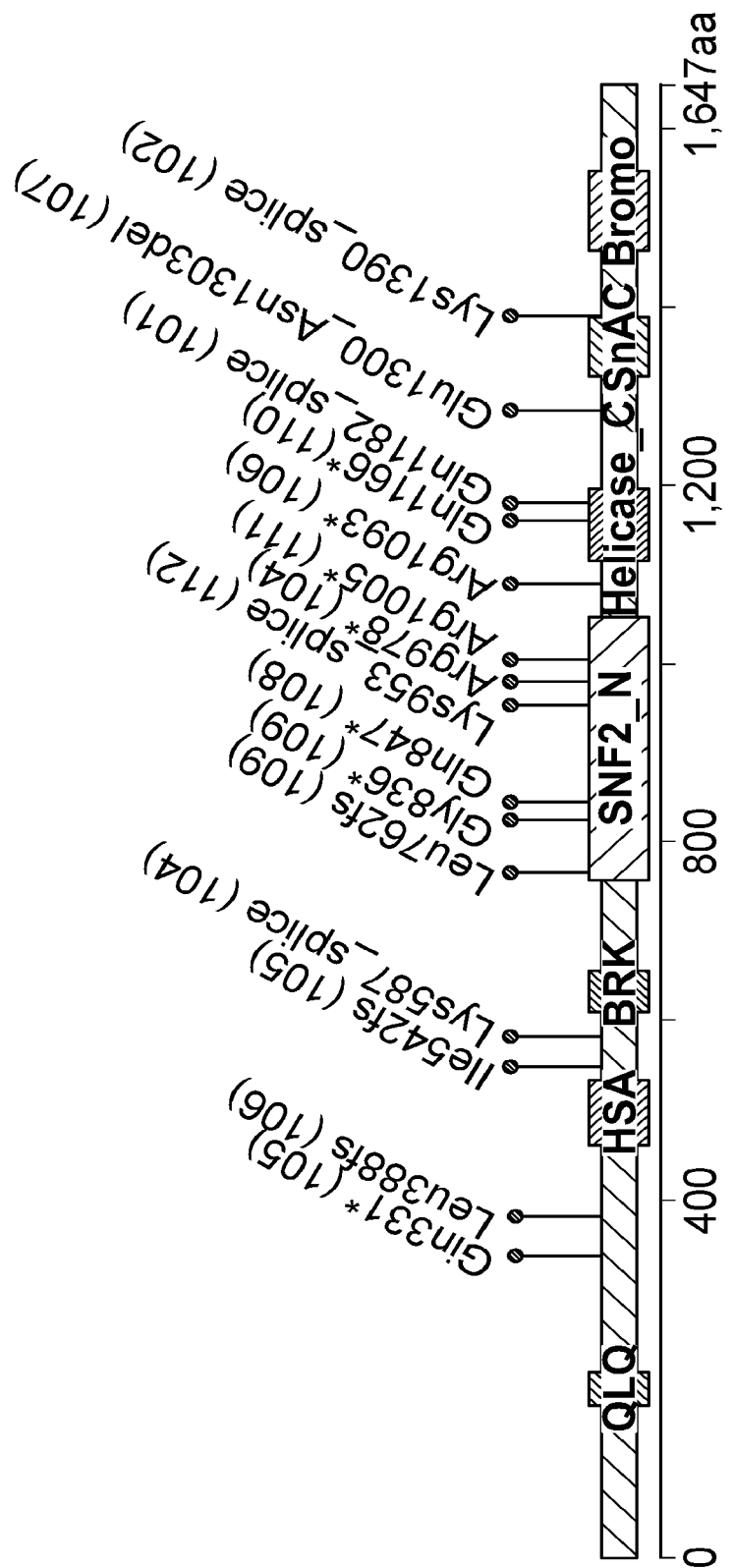
FIG. 1A is a diagram showing the position of 11 of 12 SMARCA4 mutations identified in SCCOHT and TCGA (The Cancer Genome Atlas) tissue samples relative to the domain structure of SMARCA4 protein (Uniprot ID: SMCA4_HUMAN). (Case number 103, which exhibited an exon deletion, is not shown).

The present disclosure is based upon the discovery that mutations in the SMARCA4 gene and/or associated regulatory sequences, including bi-allelic mutations, that reduce SMARCA4 gene expression and/or that reduce SMARCA4 protein levels and/or function, are very common in certain cancers including small cell carcinoma of the ovary (SCCO), in particular SCCO hypercalcemic type (SCCOHT), which is a rare, highly aggressive form of ovarian cancer.

Moreover, as disclosed herein, it was found that restoration of SMARCA4 function in SMARCA4-deficient cells suppresses cell growth while loss of SMARCA4 function in normal cells promotes cell proliferation. Thus, mutations in the SMARCA4 gene, including bi-allelic mutations that reduce SMARCA4 gene expression and/or that reduce SMARCA4 protein levels and/or function, are diagnostic of SCCOHT disease phenotype in patient and are predictive of the therapeutic efficacy of a treatment regimen for SCCOHT that achieve at least a partial restoration of SMARCA4 gene expression and/or of SMARCA4 protein levels and/or function. Moreover, at least partial restoration of SMARCA4 expression and in any event function presents itself as a therapeutic goal.

In studies leading to the presently-disclosed discoveries the genetic basis for SCCOHT was determined by sequencing the protein-coding exons in 279 cancer-related genes in 12 paired SCCOHT tumor and non-tumor samples. Among those 279 genes, SMARCA4 was the only gene that exhibited mutations in every tumor sample tested (FIG. 1B) while only four other non-recurrent somatic mutations were identified in the 278 other cancer-related genes from those 12 SCCOHT samples that were sequenced. In contrast, analysis of 4,784 non-hypermutated tumors across The Cancer Genome Atlas (TCGA) revealed somatic mutations in an average of 4.3 of those 279 genes (STD 4.4) per tumor. TCGA samples with inactivating SMARCA4 mutations had more mutations in the other 278 genes sequenced (mean=14) in contrast to the SCCOHT cases.

As discussed herein, the probability of identifying SMARCA4 mutations in all 12 SCCOHT samples is less than $2.22 \times 10^{-16}$. Based, in part, upon this tight association between certain bi-allelic, SMARCA4 gene mutations and patient samples exhibiting the SCCOHT phenotype, the present disclosure provides methods for the diagnosis of SCCOHT, which methods include, for example, the detection of reduced SMARCA4 gene expression and/or of reduced SMARCA4 protein levels and/or functionality, as well as methods for the treatment of SCCOHT. The latter methods include at least the partial restoration of wild-type SMARCA4 gene expression and/or function; at least the partial restoration of wild-type SMARCA4 protein levels and/or functionality; and/or inhibition of an activity that is elevated with reduced SMARCA4 activity or stimulation of an activity that is reduced with reduced SMARCA4 activity.

The SMARCA4 mutations that were identified in the 12 SCCOHT tumor samples are presented herein in Table 1. Based upon the predicted changes in protein structure and/or observed reduction in protein levels resulting from those SMARCA4 gene mutations; the high frequency occurrence of bi-allelic SMARCA4 mutations; and the tight association between those SMARCA4 mutations and the SCCOHT phenotype, it was discovered that such mutations, which can include insertion mutations, deletion mutations, frame shift mutations, splice site mutations, and point mutations, in particular nonsense mutations and/or missense mutations, in the SMARCA4 gene and/or in one or more sequences that control the expression and/or functionality of the SMARCA4 gene, which mutations reduce or eliminate SMARCA4 gene expression and/or function and/or result in reduced or undetectable SMARCA4 protein levels and/or functionality, are causative of the SCCOHT phenotype.

latory sequences in particular (but not limited to) mutations in both alleles of the SMARCA4 gene and/or associated regulatory sequences (i.e., bi-allelic mutations), which are known, predicted, or demonstrated to reduce or eliminate SMARCA4 gene expression and/or known, predicted, or demonstrated to reduce or eliminate SMARCA4 protein levels and/or protein function;

2. Methods for inhibiting the growth of cancer cells and for the treatment of cancers, including ovarian cancers, such as small cell carcinomas of the ovary (SCCO), in particular SCCO hypercalcemic type (SCCOHT), which cancers are associated with a cancer cell exhibiting reduced or undetectable SMARCA4 gene expression and/or with reduced or undetectable SMARCA4 protein levels and/or protein function, which methods include contacting a cancer cell or administering to a cancer patient one or more compounds, including one or more polynucleotides, polypeptides, and/or small molecules that can restore SMARCA4 gene expression and/or SMARCA4 protein levels and/or protein function and, thereby, slow or stop the growth of the cancer cell;

3. Compounds and compositions, including pharmaceutical compositions, containing those compounds, which compounds and compositions may be advantageously employed in the presently-disclosed methods for inhibiting the growth of cancer cells and for the treatment of cancers, including ovarian cancers, such as small cell carcinomas of the ovary (SCCO), in particular SCCO hypercalcemic type (SCCOHT), which cancers are associated with a cancer cell exhibiting reduced or undetectable SMARCA4 gene expression and/or with reduced or undetectable SMARCA4 protein

TABLE 1

Summary of Patient Characteristics and SMARCA4 Mutations

| Case No. | Age at diagnosis (years) | Year of diagnosis | Coding sequence change | Predicted protein change | Variant class | Tumor sequence reads | Tumor allele frequency | Affected exon | Functional domain# | IHC result |
|---|---|---|---|---|---|---|---|---|---|---|
| 101 | 40 | 2003 | G > A | p.Q1182_splice | Splice site | 1438 | 0.83 | 24 | Helicase | Loss |
| 102 | 22 | 2009 | G > A | p.K1390_splice | Splice site | 786 | 0.77 | 27 | | Loss |
| 103 | 19 | 2010 | | deletion | Exon deletion | NA | NA | 25-26 | Helicase | Retained |
| 104 | 21 | 1998 | G > A | p.K587_splice | Splice site | 198 | 0.31 | 9 | | N/A |
| | | | C > T | p.R978* | Nonsense | 322 | 0.34 | 19 | SNF2 | |
| 105 | 25 | 2009 | C > T | p.Q331* | Nonsense | 175 | 0.5 | 5 | | N/A |
| | | | TC > T | p.I542fs | Frameshift deletion | 496 | 0.48 | 9 | | |
| 106 | 40 | 2012 | C > T | p.R1093* | Nonsense | 608 | 0.47 | 6 | | Loss |
| | | | TC > T | p.L388fs | Frameshift deletion | 520 | 0.47 | 23 | Helicase | |
| 107 | 18 | 2010 | GACGAGACCGTCA > G | p.ETVN1300del | In frame deletion | 393 | 0.83 | 27 | | N/A |
| 108 | 22 | 2011 | C > T | p.Q847* | Nonsense | 126 | 0.94 | 17 | SNF2 | Loss |
| 109 | 32 | 2010 | T > TG | p.L762fs | Frameshift insertion | 299 | 0.12 | 15 | SNF2 | Loss |
| | | | G > T | p.G836* | Nonsense | 413 | 0.49 | 17 | SNF2 | |
| 110 | 42 | 2011 | C > T | p.Q1166* | Nonsense | 518 | 0.8 | 24 | Helicase | Loss |
| 111 | 35 | 2012 | C > T | p.R1005* | Nonsense germline^ | 609 | 0.93 | 20 | SNF2 | Loss |
| 112 | 28 | 2011 | G > A | p.K953_splice | Splice site | 288 | 0.75 | 18 | SNF2 | Equivocal |

Based upon these and other discoveries, which are described in detail herein, the present disclosure provides:

1. Methods for the diagnosis of cancers, including ovarian cancers, such as small cell carcinomas of the ovary (SCCO), in particular SCCO hypercalcemic type (SCCOHT), which cancers are associated with reduced or undetectable SMARCA4 gene expression and/or with reduced or undetectable SMARCA4 protein levels and/or protein function, which methods include the detection of one or more mutations, including one or more nonsilent germline or somatic mutations, in the SMARCA4 gene and/or associated regulevels and/or protein function. Exemplified herein are compounds, including polynucleotides, polypeptides, and small molecules that can be used to restore SMARCA4 gene expression and/or function and/or restore SMARCA4 protein level and/or function and, thereby, slow or stop the growth of a cancer cell; and 4. Diagnostic kits for identifying a cancer cell or a detecting in a patient a cancer cell that exhibits reduced or eliminated SMARCA4 gene expression and/or function and/or reduced or absent SMARCA4 protein level and/or functionality, which diagnostic kits contain one or more agents that can be used alone or in combination to: (a) detect a mutation in a SMARCA4 gene and/or mRNA, such as an insertion mutation, a deletion mutation, a frame shift mutation, a splice site mutation, and a point mutation, in particular nonsense mutation and/or a missense mutation in a SMARCA4 gene and/or mRNA; (b) detect a reduction in SMARCA4 mRNA level; (c) detect a reduction in SMARCA4 protein level; and/or (d) detect a reduction in SMARCA4 protein functionality.

These and other aspects of the present disclosure can be better understood by reference to the following non-limiting definitions.

Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, reaction conditions, and so forth used in the specification and claims are to be understood as being modified in all instances by the term "about" meaning approximately. Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term "gene" is used broadly to refer to any segment of DNA associated with a biological function. Thus, genes include, but are not limited to, coding sequences and/or the regulatory sequences required for their expression. Genes can also include non-expressed DNA segments that, for example, form introns or recognition sequences for a polypeptide. Genes can be obtained from a variety of sources, including cloning from a source of interest or synthesizing from known or predicted sequence information, and can include sequences designed to have desired parameters.

As used herein, the terms "peptide," "protein" and "polypeptide" refer to any polymer comprising any of the 20 protein amino acids, regardless of its size. Although "protein" is often used in reference to relatively large polypeptides, and "peptide" is often used in reference to small polypeptides, usage of these terms in the art overlaps and varies. The term "protein" as used herein refers to peptides, polypeptides and proteins, unless otherwise noted. As used herein, the terms "protein", "polypeptide" and "peptide" are used interchangeably herein when referring to a gene expression product.

As used herein, the term "polynucleotide" refers to a nucleic acid molecule, such as mRNA, RNA, cRNA, cDNA or DNA. The term typically refers to oligonucleotides greater than 30 nucleotide residues in length. Smaller nucleic acid molecules, generally between 5 and 30 nucleotides long, are referred to as oligonucleotides. ***

As used herein, the term "SWI/SNF related, matrix associated, actin dependent regulator of chromatin, subfamily a, member 4" or "SMARCA4" refers to a protein that in humans is encoded by the SMARCA4 gene, which is located on the short (p) arm of chromosome 19 at position 13.2. SMARCA4 is also known as, ATP-dependent helicase SMARCA4, BAF190, BAF190A, brahma protein-like 1, BRG1, BRG1-associated factor 190A, BRM/SWI2-related gene 1, FLJ39786, hSNF2b, MRD16, nuclear protein GRB1, protein brahma homolog 1, protein BRG-1, RTPS2, SMCA4_HUMAN, SNF2, SNF2-beta, SNF2L4, SNF2LB, SNF2-like 4, sucrose nonfermenting-like 4, SWI2, or transcription activator BRG1. The SMARCA4 protein forms a subunit of several different SWI/SNF protein complexes. SWI/SNF complexes regulate gene expression by a process known as chromatin remodeling. Chromatin is the network of DNA and protein that packages DNA into chromosomes. The structure of chromatin can be changed (remodeled) to alter how tightly DNA is packaged. Chromatin remodeling is one way gene expression is regulated during development; when DNA is tightly packed, gene expression is lower than when DNA is loosely packed. Exemplary sequences of SMARCA4 mRNA, genomic DNA and protein are provided in SEQ ID NOs. 1, 2, 3, 4, 5, 6, 7 and 8.

As used herein, the term "SWI/SNF complex" refers to a protein complex that includes SMARCA4 and isoforms of ARID1, SMARCC, SMARCD, ACTL6 proteins. In eukaryotes, the SWI/SNF complex plays an important role in nucleosome remodeling. SWI/SNF complex (in yeast) is capable of altering the position of nucleosomes along DNA. Whitehouse et al., *Nature* 400(6746): 784-7 (1999). Through their ability to regulate gene activity, SWI/SNF complexes are involved in many processes, including repairing damaged DNA; copying (replicating) DNA; and controlling the growth, division, and maturation (differentiation) of cells. The BRG1 protein and other SWI/SNF subunits are thought to act as tumor suppressors, which keep cells from growing and dividing too rapidly or in an uncontrolled way. It was first identified in 1998 as a tumor suppressor in rhabdoid tumors, a rare pediatric malignancy. Versteege et al., *Nature* 394(6689): 203-6 (1998). As DNA sequencing costs diminished, many tumors were sequenced for the first time around 2010. Several of these studies revealed SWI/SNF to be a tumor suppressor in a number of diverse malignancies. Wiegand et al., *N. Engl. J. Med.* 363(16): 1532-43 (2010).

As used herein, the term "mutation" refers to any modification in the nucleotide sequence of a nucleic acid relative to a wild-type nucleic acid sequence. Mutations include, without limitation, insertion mutations, deletion mutations, frame shift mutations, splice site mutations, and point mutations, in particular nonsense mutations and/or missense mutations. Silent mutations, and more generally mutations having no deleterious effect on the sequence of an expression product or on its regulation are not contemplated for the products and methods of the present disclosure. Of particular interest herein are mutations that result in reduced or eliminated expression of SMARCA4 or in reduced or eliminated resulting SMARCA4 protein function (as defined below).

As used herein, the term "polymorphism" refers to the occurrence of two or more genetically determined alternative variant sequences (i.e., alleles) occurring in a population. A polymorphic marker is the locus at which divergence occurs. Preferred markers have at least two alleles, each occurring at a frequency of greater than 1%. A polymorphic locus may be as small as one base pair (e.g., a single nucleotide polymorphism (SNP)). Exemplary SNPs are disclosed herein and can be referenced by accession number (e.g., "rs number"). The rs numbers (searchable through NCBI's Entrez SNP website) comprise the SNP as well as proximate contiguous nucleotides provided to place the SNP in context within the gene. Thus, rs numbers referenced herein are intended to indicate the presence of the SNP and not to require the presence of all or part of the contiguous nucleotide sequence disclosed therein. Further, reference to a particular polymorphism is intended to also encompass the complementary nucleotide(s) on the complementary nucleotide strand (e.g., coding and non-coding polynucleotides).

As used herein, the term "reference genotype" as used herein refers to a previously determined pattern of genetic variation associated with a particular phenotype, such as for example male infertility due to low sperm motility and/or impaired mitochondrial function. The reference genotype can be as minimal as the determination of a single base pair, as in determining one or more polymorphisms in the subject. Further, the reference genotype can comprise one or more haplotypes. Still further, the reference genotype can comprise one or more polymorphisms exhibiting high linkage disequilibrium to at least one polymorphism or haplotype. In some particular embodiments, the reference genotype comprises one or more polymorphisms (e.g., SNPs) and/or haplotypes of SMARCA4, SMARCA2, or combinations thereof determined to be associated with male infertility due to low sperm motility and/or impaired mitochondrial function. In some embodiments, the haplotypes represent a particular collection of specific single nucleotide polymorphisms.

As used herein, the terms "plasmid" and "vector" refer to any of a wide variety of nucleic acids into which a desired sequence may be inserted by restriction and ligation for transport between different genetic environments or for expression in a host cell. Vectors are typically composed of DNA, although RNA vectors are also available. Vectors include, but are not limited to, plasmids and phagemids. Expression vectors and cloning vectors are examples of vectors that are able to replicate in a host cell, and that typically include a region, often defined by a multiple cloning site, into which a nucleic acid may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. Expression vectors further include one or more transcriptional promoters that facilitate the binding of a polymerase, which permits the expression of the exogenous gene or cDNA.

As used herein, the term "RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences. The choice of promoter and other regulatory elements generally varies according to the intended host cell.

As used herein, the term "expression" generally refers to the cellular processes by which an RNA is produced by RNA polymerase (RNA expression) or a polypeptide is produced from RNA (protein expression). Thus the term "expression" describes levels of either RNA or protein in a cell that can be quantified by methods described in the disclosure.

As used herein, the terms "loss-of-function" or "dysfunctional" or "loss of expression" variously refer to a reduced level of expression of a gene (either in RNA or in protein) or reduced or absent protein production or to a decreased ability of a gene to perform its biological function, e.g. to bind to another protein such as a receptor, to bind to DNA in one cell when compared to the level in another cell, or in one condition when compared to another condition. As used herein, "loss-of-function," "dysfunctional," or "loss of expression" refers to a reduction in gene expression, protein production, or protein activity that is from about 0% to about 50%, or from about 0% to about 40%, or from about 0% to about 30%, or from about 0% to about 20%, or from 0% to about 10%, or less than about 5% of that observed in a cell exhibiting normal or wild-type gene expression, protein production, or protein activity with respect to SMARCA4. SMARCA4 functions include both direct and downstream functions as described below.

As used herein, the term "gain-of-function" refers to an increase in the level of expression of a gene (either in RNA or in protein) or to an enhanced ability to perform its direct or indirect biological function, e.g. to bind to another protein such as a receptor, to bind to DNA in one cell when compared to the level in another cell, or in one condition when compared to another condition. As used herein, "gain-of-function" refers to an increase in gene expression, protein production, or protein activity in a cell that is from about 2-fold to about 1000-fold, or from about 5-fold to about 500-fold, or from about 10-fold to about 200-fold, or from about 20-fold to about 100-fold, or from about 30-fold to about 70-fold higher in a cell exhibiting normal or wild-type gene expression, protein production, or protein activity than in a cell exhibiting "a loss of function," a "dysfunction," or a loss of expression of said gene or its ability to perform its biological function.

As used herein, the term "restoration" refers to an increase in expression of a previously deficient gene (either in RNA or in protein) or to an enhanced ability of such a gene to perform its biological function, e.g. to bind to another protein such as a receptor, to bind to DNA, in a cancer cell or in a cell that is otherwise exhibiting dysfunction or deficiency of this gene, to a level comparable to, equal to or higher than the expression or ability of the same gene in a non-cancer normal cell.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed as a "p-value". Those p-values that fall below a user-defined cutoff point are regarded as significant. A p-value in some embodiments less than or equal to 0.05, in some embodiments less than 0.01, in some embodiments less than 0.005, and in some embodiments less than 0.001, are regarded as significant.

As used herein, the term "biological sample" refers to a tissue or fluid sample obtained from a patient, typically such a biological sample is a tumor sample, including an ovarian tumor sample, in particular an SCCOHT sample such as a tissue or biopsy sample (e.g., tumor biopsy). Biological samples may also include sections of tissues such as frozen sections taken for histological purposes.

As used herein, the term "diagnosed" refers to a determination that has been made that the cancer is, for example, a SCCOHT, an ovarian cancer, a lung cancer, or other cancer that exhibits dysfunctional and/or deficient SMARCA4. A diagnosis may be made prior to (on a different sample) performing the present methods for inhibiting the growth and/or survival of a SCCOHT, an ovarian cancer, a lung cancer, or other cancer that exhibits dysfunctional and/or deficient SMARCA4 or a diagnosis may be made in conjunction (i.e., either concurrently or sequentially) with the present methods for inhibiting the growth and/or survival of a SCCOHT, an ovarian cancer, a lung cancer, or other cancer that exhibits dysfunctional and/or deficient SMARCA4.

The term "reduced SMARCA4 protein function" is meant to include reduction in a direct or indirect (downstream) biological functions. As used herein, the term "SMARCA4 protein function" refers to any of the direct or indirect (downstream) activities of SMARCA4. An example of a direct activity is its participation in the SWI/SNF complex. An example of a downstream activity includes any of the activities described above for the SWI/SNF complex, such as the tumor suppressing activity of SMARCA4 as well as any pathways by which such downstream activities are mediated, for example inhibition of EZH2 hyperactivity as describer further herein. Reductions in function can be brought about for example by an altered SMARCA4 protein structural configuration or conformation, an altered SMARCA4 protein post-translational modification, an altered level of protein-protein complex formation between a SMARCA4 protein and another protein, such as altered SWI/SNF or BAF complex formation and/or an altered level of one or more SMARCA4 downstream target genes, or corresponding mRNA, such as one or more of the CDH1, CDH3, EHF, RRAD, and/or ML-IAP genes or mRNA. As used herein, reduced SMARCA4 protein function includes a reduction in SMARCA4 protein function that is from about 0% to about 50%, or from about 0% to about 40%, or from about 0% to about 30%, or from about 0% to about 20%, or from 0% to about 10%, or less than about 5% of the protein functionality in a cell exhibiting normal or wild-type SMARCA4 protein function As used herein, the term "identifying" refers to an initial determination, such as a determination that a cancer cell exhibits dysfunctional and/or deficient SMARCA4 and/or that a cancer cell exhibits enhanced susceptibility to a therapeutic compound that enhances SMARCA4 functionality and/or promote SMARCA4 expression. "Identifying" does not determine the selection of a final medical treatment regimen, but may be used by a skilled clinician in designing and/or selecting such a treatment regimen.

As used herein, the terms "treatment" and "treating" refer to therapeutic regimen that inhibits (reduces or arrests or causes apoptosis) the growth of a cancer cell in patient by administering to the patient an compound that increases and/or restores SMARCA4 gene expression and/or protein functionality and/or by administering to the patient a wild-type SMARCA4 gene or a wild-type SMARCA4 protein. Suitable treatments include the administration to the patient of a SMARCA4 gene or polynucleotide sequence that increases SMARCA4 gene expression that is a component of (a) a viral vector, such as a retroviral vector, an adenoviral vector, or a vaccinia-viral vector, (b) a liposome, or (c) a nano-particle. Suitable treatments also include the administration to the patient of a SMARCA4 protein that is a component of a liposome or a nanoparticle. Alternative suitable treatments include the administration to the patient of an antibody, shRNA, siRNA, or antisense-oligonucleotide that reduces SMARCA2 gene expression.

As used herein, the terms "small cell carcinoma of the ovary, hypercalcemic type" and "SCCOHT" refer to a rare and aggressive form of ovarian cancer. SCCOHT is still categorized as a miscellaneous tumor by the World Health Organization. Most tumors are unilateral, and size greater than 10 cm may be prognostically favorable due to earlier onset of symptoms resulting in stage migration. Estel et al., *Arch Gynecol Obstet* 284:1277-82 (2011). Histologic classification can be challenging, but commonly expressed immunohistochemical markers such as CD10, WT1, and calretinin can be useful in the setting of absent inhibin, S100, and chromogranin expression to exclude histological mimics. McCluggage, *Adv Anat Pathol* 11:288-96 (2004).

An "allele" refers to any of two or more alternative forms of a gene that occupy the same locus on a chromosome. If two copies of same allele are present in an individual, the individual is homozygous for that allelic form of the gene. If different alleles are present in an individual, the individual is heterozygous for that gene.

The term "primer" refers to a nucleic acid capable of acting as a point of initiation of synthesis along a complementary strand when conditions are suitable for synthesis of a primer extension product. The synthesizing conditions include the presence of four different bases and at least one polymerization-inducing agent such as reverse transcriptase or DNA polymerase. These are present in a suitable buffer, which may include constituents which are co-factors or which affect conditions such as pH and the like at various suitable temperatures. A primer is preferably a single strand sequence, such that amplification efficiency is optimized, but double stranded sequences can be utilized.

The term "probe" refers to a nucleic acid that hybridizes to a target sequence. In some embodiments, a probe includes about eight nucleotides, about 10 nucleotides, about 15 nucleotides, about 20 nucleotides, about 25 nucleotides, about 30 nucleotides, about 40 nucleotides, about 50 nucleotides, about 60 nucleotides, about 70 nucleotides, about 75 nucleotides, about 80 nucleotides, about 90 nucleotides, about 100 nucleotides, about 110 nucleotides, about 115 nucleotides, about 120 nucleotides, about 130 nucleotides, about 140 nucleotides, about 150 nucleotides, about 175 nucleotides, about 187 nucleotides, about 200 nucleotides, about 225 nucleotides, and about 250 nucleotides. A probe can further include a detectable label. A detectable label can be covalently attached directly to a probe oligonucleotide, e.g., located at the probe's 5' end or at the probe's 3' end.

The terms "hybridize" or "hybridization," as is known to those of ordinary skill in the art, refer to the binding or duplexing of a nucleic acid molecule to a particular nucleotide sequence under suitable conditions, e.g., under stringent conditions.

As used herein, the term "genotype" means a sequence of nucleotide pair(s) found at one or more sites in a locus on a pair of homologous chromosomes in an individual. Genotype may refer to the specific sequence of the gene.

Methods for the Detection of Small Cell Carcinoma of the Ovary

The present disclosure provides methods for the diagnosis of ovarian cancers, such as small cell carcinomas of the ovary (SCCO), in particular SCCO hypercalcemic type (SCCOHT), which cancers are associated with reduced or undetectable SMARCA4 gene expression and/or with reduced or undetectable SMARCA4 protein levels and/or protein function, which methods include the detection of one or more mutations, including one or more germline or somatic mutations, in the SMARCA4 gene and/or associated regulatory sequences in particular mutations in both alleles of the SMARCA4 gene and/or associated regulatory sequences (i.e., bi-allelic mutations), which are known, predicted, or demonstrated to reduce or eliminate SMARCA4 gene expression and/or known, predicted, or demonstrated to reduce or eliminate SMARCA4 protein levels and/or protein function.

As disclosed herein, it was discovered that mutations in the SMARCA4 gene are highly distinctive markers for SCCOHT cancer cells and patients afflicted with SCCOHT or in any event having SCCOHT cancer cells. Among all 12 SCCOHT patient samples characterized, sequencing of all protein-coding exons in 279 cancer-related genes for 12 paired tumor and normal SCCOHT samples identified SMARCA4 gene mutations, typically bi-allelic SMARCA4 gene mutation (FIG. 1B), that resulted in reduced SMARCA4 gene expression and/or functionality. Moreover, it was determined that the probability of identifying SMARCA4 mutations in all 12 samples was less than $2.22 \times 10^{-16}$.

Mutations, including loss-of-function/loss-of-expression mutations, within the SMARCA4 gene were identified in each of the 12 SCCOHT patients studied (see, Table 1), which cause the SMARCA4 gene to either encode reduced or undetectable levels of SMARCA4 mRNA, to encode SMARCA4 mRNA that cannot be transcribed into SMARCA4 protein, and/or to encode mRNA that does not encode functional SMARCA4 protein. Examples of such mutations include insertion mutations, deletion mutations, frame shift mutations, splice site mutations, nonsense mutations, and missense mutations, which result in reduced or undetectable levels of SMARCA4 protein or SMARCA4 protein having reduced or undetectable functionality.

In the 12 SCCOHT patients studied, several of SMARCA4 gene mutations were non-sense or frameshift mutations that occurred within or upstream of the region of the SMARCA4 gene encoding the SMARCA4 helicase and SNF2 functional domains. Because the helicase and SNF2 functional domains are essential for SMARCA4 functionality, those mutations inactivated the SMARCA4 protein, which was frequently undetectable by immunohistochemistry analysis (IHC).

Thus, as disclosed herein, the detection of mutations within the SMARCA4 gene or mRNA transcript that are predicted to result in reduced or undetectable intracellular levels of SMARCA4 protein or that are predicted to result in SMARCA4 protein having reduced or undetectable functional activity can be exploited diagnostically to determine if a cancer cell exhibits the SCCOHT phenotype, or conversely, to exclude SCCOHT.

As further disclosed herein, the determination that a SMARCA4 protein exhibits reduced or undetectable functionality or the detection of truncated, or otherwise structurally altered SMARCA4 protein, are all similarly predictive of SCCOHT and, therefore can also be exploited diagnostically to determine if a cancer cell exhibits the SCCOHT phenotype or to exclude same.

Methods and Kits

The present disclosure provides reagents, methods, and kits for determining the presence and/or amount of: a) at least one loss of function mutation in a SMARCA4 gene; b) mutant mRNA encoding SMARCA4 protein; and/or c) mutant SMARCA4 protein in or isolated from a biological sample.

Methods include a method of detecting the presence of a loss of function mutation in a SMARCA4 nucleic acid sequence, comprising: isolating a nucleic acid that comprises a nucleic acid that encodes a portion of a SMARCA4 protein or that comprises a portion of the SMARCA4 gene, wherein the nucleic acid comprises a nucleotide position that can be mutated as compared to a reference sequence, wherein when the nucleotide position is mutated a function of SMARCA4 protein is decreased or eliminated, and sequencing the isolated nucleic acid to determine whether the nucleotide in the nucleotide position is mutated as compared to the reference sequence. Another method provides a method of detecting the presence of a loss of function mutation in a SMARCA4 nucleic acid sequence, comprising: contacting the nucleic acid that comprises a nucleic acid that encodes a portion of a SMARCA4 protein or that comprises a portion of the SMARCA4 gene with a primer or probe under conditions suitable for hybridization and/or amplification, wherein the nucleic acid comprises a nucleotide position that can be mutated as compared to a reference sequence, wherein when the nucleotide position is mutated a function of SMARCA4 protein is eliminated or decreased, and determining whether the nucleic acids hybridize to one another and/or determining the size and/or sequence of the amplified region.

In other embodiments, a method for determining whether the nucleic acids hybridize to one another comprises determining whether a mismatch is present by contacting the hybridized sample with an agent that cleaves at the site of a mismatch, and identifying the size of any of the products of the cleavage reaction, wherein if a mismatch is present a cleavage product is detected.

In some embodiments, the method involves detecting a germline mutation using an array or probe designed to distinguish mutations in a SMARCA4 gene. Mutations include insertions, deletions, and substitutions. In some embodiments, substitutions result in the formation of stop codons. In other embodiments, insertions or deletions result in frameshift or missense mutations. Probes or cDNA oligonucleotides that detect mutations in a nucleic acid sequence can be designed using methods known to those of skill in the art.

In some embodiments, mutations are identified as those that lead to a decrease in expression of SMARCA4 or in expression of a SMARCA4 protein with decreased or eliminated function. In some embodiments, the mutation is a missense, frameshift, or stop codon mutation. In an embodiment, the mutation results in a carboxy-terminal truncation of the SMARCA4 protein. In some embodiments, the mutations are one or more or all the mutations shown in Table 1.

In some embodiments, the methods and kits may provide restriction enzymes and/or probes that can detect changes to the restriction fragments as a result of the presence of at least one mutation in the gene sequence encoding SMARCA4 protein. The publicly available human genome sequence can be used for example to generate a RFLP map.

In some embodiments, the methods and kits provide for primers and probes that can detect the presence of at least one mutation in the mRNA and/or detect an alteration in size or sequence of mRNA. In some embodiments, primers are designed to hybridize within a certain temperature range and may also include other sequences such as universal sequencing sequences. In some embodiments, the target sequence of the primer/probe sets includes those that are complementary to mature coding sequence. Those primer/probes can act as a positive control to detect full length transcripts that encode active SMARCA4 protein. In some embodiments, the primers and probes complementary to the 3' untranslated region are excluded as positive controls in order to avoid spurious detection of degraded mRNA and to enhance the correlation between the mRNA that is measured by this assay and the protein that is actually expressed.

In some embodiments, the kit can include one or more probes and/or primer attached to a solid substrate. In some embodiments, an array can comprise one or more of SMARCA4 gene-specific sequences. In some embodiments, the array or kit excludes detection of a gene selected from the group consisting of actin, gapdh, aldolase, hexokinase, cyclophilin and combinations thereof.

In some embodiments, the methods and kits provide reagents for detection of the presence or absence of the SMARCA4 protein. In some embodiments, the reagents include an antibody that can detect full length SMARCA4 protein in cells. In other embodiments, an antibody can detect polypeptides that have an alteration in one or more domains of the SMARCA4 polypeptide. The antibodies can be detectably labeled. Detectable labels include for example fluorescent labels, radioactive isotope labels, and polypeptide labels including enzymes or molecules like biotin. The methods of detection involve for example immunohistochemical or radiological detection of SMARCA4 protein or altered SMARCA4 protein in tumor tissue.

The kit can establish patterns of SMARCA4 expression that may be associated with certain cancers, including ovarian cancers, in particular SCCOHT. The presence of a SMARCA4 mutation can be used to prognosticate risk of malignancy, diagnose or confirm or exclude diagnosis of SCCOHT in a patient, and help identify appropriate treatment.

The disclosure provides a method of determining the diagnosis or prognosis of ovarian cancer comprising: determining whether the gene or nucleic acid that comprises a nucleic acid that encodes a portion of a SMARCA4 protein or that comprises a portion of the SMARCA4 gene has the reference sequence or the mutated sequence. In some embodiments, the expression or decrease in expression in a cell or tissue sample can be determined for example by PCR analysis, hybridization analysis, in situ analysis using hybridization, or antibody detection methods.

In some embodiments, the cancer is selected from the group consisting of ovarian cancer, lung cancer, or other cancer that exhibits dysfunctional and/or deficient SMARCA4 as described herein.

In some embodiments, once a cancer is diagnosed in a patient other family members may also be examined for the presence or absence of a loss of function mutation in SMARCA4.

In some embodiments, after detection of one or more mutations in SMARCA4 is detected, a treatment is selected and administered to the patient. A method of treating a cancer, comprising administering to a cancer patient, one or more compounds, including one or more polynucleotides, polypeptides, and/or small molecules that can restore SMARCA4 gene expression and/or SMARCA4 protein levels and/or protein function and, thereby, slow or stop the growth of the cancer cell.

Each of these aspects of the present disclosure is described in further detail in the following sections.

1. Methodology for Detecting Mutations in a SCCOHT Nucleotide Sequence

In one aspect, the present disclosure provides methods for identifying a cancer cell or a patient with a cancer cell that exhibits reduced or undetectable SMARCA4 protein functionality or reduced or undetectable SMARCA4 protein levels, wherein the methods include detecting a mutation in a SMARCA4 gene or a SMARCA4 mRNA, such as a nonsense mutation, a missense mutation, a deletion mutation, an insertion mutation, a frameshift mutation, and/or a splice site mutation in a SMARCA4 gene or a SMARCA4 mRNA, which mutation is predictive of reduced SMARCA4 protein levels and/or functionality.

The detection of mutations in a SMARCA4 gene or a SMARCA4 mRNA, including the detection of nonsense mutations, missense mutations, deletion mutations, insertion mutations, frameshift mutations, and/or splice site mutations in a SMARCA4 gene or a SMARCA4 mRNA can be achieved by routine modification of methodologies that are ready available to and known by those of skill in the art in conjunction with the reported nucleotide sequences for the SMARCA4 gene and/or a SMARCA4 mRNA, which are presented herein as SEQ ID NOs 1, 3, 5, and 7. Exemplary methodologies for detecting mutations in a nucleotide sequence (e.g., genomic DNA, mRNA, cDNA) include amplification, sequencing, and hybridization methodologies, some of which are presented herein to exemplify rather than limit the presently-disclosed methods for detection of SCCOHT, which can be applied by routine modification to other cancers associated with mutations in the SMARCA4 gene.

(a) SMARCA4 Functional Domains and Activities

The following summarizes representative activities of SMARCA4, including the role of those activities in the formation of protein-protein complexes as well as the structural basis for those activities (Reisman et al., *Oncogene* 28:1653-68 (2009) and Wilson and Roberts, *Nat Rev Cancer* 11:481-92 (2011)). Based upon this description of those activities, one skilled in the art will readily recognize the nature of mutations, insertions, and/or substitutions within the gene encoding SMARCA4 protein that will reduce and/or eliminate one or more of those activities and, therefore, the functionality of the SMARCA4 protein.

The SMARCA4 protein contains the following conserved domains: (1) a proline rich region, containing more than 25% of proline residues in the amino acid sequence; (2) HSA and BRK domains, containing motifs that may predict binding to DNA; (3) an ATPase/helicase domain, contains motifs present in the DEAD helicases superfamily ("DEAD" disclosed as SEQ ID NO: 16); and (4) a bromodomain, found in many chromatin-associated proteins. Singh et al., Biol Chem 387(10-11):1469-78 (2006). SMARCA4 is the catalytic subunit of the chromatin-remodeling complex SWI-SNF and influences transcriptional regulation by disrupting ne-DNA contacts in an ATP-dependent manner.

SMARCA4 is a key component of the SWI/SNF complex, which functions as a master regulator of gene expression through chromatin remodeling to alter nucleosome conformation, making it more accessible to transcriptional activation. Reisman et al., *Oncogene* 28:1653-68 (2009) and Wilson and Roberts, *Nat Rev Cancer* 11:481-92 (2011). SMARCA4's importance has also been demonstrated in its function to regulate the expression of genes known to be involved in tumor suppression, apoptosis and epigenetics such as cadherin 1 (CDH1), cadherin 3 (CDH3), ETS homologous factor (EHF), Ras-related associated with diabetes (RRAD) and melanoma inhibitor of apoptosis (ML-IAP). Song et al., *Mol Cancer Res* 0427 (2013), Published Online Jan. 20, 2014; Saladi et al., *Pigment Cell Melanoma Res.* 26(3): 377-91 (2013).

(b) Amplification

Detection of SMARCA4 mutation may be performed by nucleic acid amplification. As used herein, the term "amplification" refers to the production of multiple copies of a target nucleic acid that contains at least a portion of the intended specific target nucleic acid sequence. The multiple copies are referred to, interchangeably, as amplicons or amplification products. In certain aspects of the present disclosure, the amplified target contains less than the complete target mRNA sequence (i.e., spliced transcript of exons and flanking untranslated sequences) and/or target genomic sequence (including introns and/or exons). For example, specific amplicons may be produced by amplifying a portion of the target polynucleotide by using amplification primers that hybridize to, and initiate polymerization from, internal positions of the target polynucleotide. The amplified portion contains a detectable target sequence that may be detected using any of a variety of well-known methods.

The polymerase chain reaction (PCR; described for example in U.S. Pat. Nos. 4,683,195; 4,683,202; 4,800,159; 4,965,188) uses multiple cycles of denaturation, annealing of primer pairs to opposite strands, and primer extension to exponentially increase copy numbers of the target sequence. In a variation called RT-PCR, reverse transcriptase (RT) is used to make a complementary DNA (cDNA) from mRNA, and the cDNA is then amplified by PCR to produce multiple copies of DNA.

Total RNA may be extracted from cancer tissue samples or cells and non-cancer control tissue samples or cells using Trizol recompound. First strand synthesis may be carried out using 1-2 μg of total RNA with SuperScript II reverse transcriptase (Life Technologies, Carlsbad, Calif.) at 42° C. for one hour. cDNA may then be amplified by PCR with SMARCA4 gene-specific primers that are designed based upon SMARCA4 nucleotide sequences presented in SEQ ID NO: 1, SEQ ID NO: 3, SEQ ID NO: 5, and SEQ ID NO: 7, or that are otherwise known and readily available to those skilled in the art. Specific examples of useful DNA polymerase include LA Taq DNA polymerase (Takara), Ex Taq polymerase (Takara), Gold Taq polymerase (Perkin Elmer), AmpliTaq (Perkin Elmer), Pfu DNA polymerase (Stratagene) and the like.

Subsequently, the amplified product can be subjected to agarose gel electrophoresis, followed by staining with ethidium bromide, SYBR Green solution or the like to thereby detect the amplified product as a band or two to three bands (DNA fragments). Thus, a part of a gene encoding SMARCA4, containing a genetic polymorphism can be detected as a DNA fragment. Instead of agarose gel electrophoresis, polyacrylamide gel electrophoresis or capillary electrophoresis may be performed. It is also possible to perform PCR using primers labeled in advance with a substance such as fluorescent dye and to detect the amplified product. A detection method which does not require electrophoresis may also be employed; in such a method, the amplified product is bound to a solid support such as a microplate, and a DNA fragment of interest is detected by means of fluorescence, enzyme reaction, or the like.

For example, TaqMan PCR can be used to detect SMARCA4 gene deletions or insertions. TaqMan PCR is a method using PCR reaction with fluorescently labeled allele-specific oligos and Taq DNA polymerase. The allele-specific oligo used in TaqMan PCR (called "TaqMan probe") may be designed based on the SNP information and need not amplify the whole gene or even a whole exon or intron. The 5' end of TaqMan probe is labeled with fluorescence reporter dye R (e.g. FAM or VIC), and at the same time, the 3' end thereof is labeled with quencher Q (quenching substance). Thus, under these conditions, fluorescence is not detectable since the quencher absorbs fluorescence energy. Since the 3' end of TaqMan probe is phosphorylated, no extension reaction occurs from TaqMan probe during PCR reaction. However, when PCR reaction is performed using this TaqMan probe together with Taq DNA polymerase and primers designed so that an SNP-containing region is amplified, the reaction described below occurs.

First, a TaqMan probe hybridizes to a specific sequence in the template DNA, and at the same time, an extension reaction occurs from a PCR primer. At this time, Taq DNA polymerase having 5' nuclease activity cleaves the hybridized TaqMan probe as the extension reaction of PCR primer proceeds. When the TaqMan probe has been cleaved, the fluorescent dye becomes free from the influence of the quencher. Then, fluorescence can be detected.

For example, two alleles are supposed: one allele has A at the SNP site (allele 1) and the other allele has G at the SNP site (allele T). A TaqMan probe specific to allele 1 is labeled with FAM and another TaqMan probe specific to allele 2 is labeled with VIC. These two allele specific oligos are added to PCR recompounds, and then TaqMan PCR is performed with a template DNA whose SNP is to be detected.

Subsequently, fluorescence intensities of FAM and VIC are determined with a fluorescence detector. When the SNP site of the allele is complementary to the site within TaqMan probe corresponding to the SNP, the probe hybridizes to the allele; and Taq polymerase cleaves the fluorescent dye of the probe, which becomes free form the influence of the quencher. As a result, fluorescence intensity is detected.

Other PCR amplification methods can also be used. Any suitable PCR method for detecting SNPs in target DNA are contemplated by the present invention, including new methods, such as the invader PCR method (e.g., Allawi et al, *J Clin Microbio* 44: 3443-47 (2006), incorporated herein by reference) or the SniPer PCR method (Huentelman et al., *BMC Genomics* 6:149 (2005), incorporated herein by reference), both of which can be used to detect SNPs.

In addition to detect point mutations, PCR amplification methods can also be used together with other common methods to detect deletions, insertions of the SMARCA4 genes. For example, amplified SMARCA4 or portions thereof can be applied to an agarose gel and the length of the SMARCA4 PCR products can be deduced by comparing to the known length of wide-type SMARCA4 genomic sequence or cDNA, or corresponding portions thereof. Primers can be selected to amplify targeted portions of the SMARCA gene and can be labelled for detection. Primers can be included for co-amplification of positive and negative controls.

(c) Sequencing

Mutations of SMARCA4 gene can be determined by the direct sequencing of genomic DNA, cDNA or mRNA in a cancer patient tissue sample or cell and/or a non-cancer donor control tissue sample or cell. Alternatively, mutation of SMARCA4 gene can be determined following conversion of mRNA into cDNA by reverse transcription. Multiple methods can be used to sequence SMARCA4 nucleotide sequence. After SMARCA4 is sequenced, loss-of-function mutations can be detected by examining the locations of the mutations, the effects of the mutations on critical functional domains of SMARCA4, and other bioinformatics analysis methods.

Nucleotide sequencing can be achieved through chain termination methods, which were first developed by Frederick Sanger, and can be referred to as Sanger sequencing methods. In chain termination methods, four PCR reactions are performed wherein each reaction is spiked with a single dideoxynucleotide (ddNTP), which is a nucleotide lacking a 3' hydroxyl group (e.g., ddATP, ddTTP, ddCTP, ddGTP). When a ddNTP is incorporated into a nascent chain of DNA, synthesis of the nascent chain is halted; this generates a mixture of variable length oligonucleotides that can be resolved by size using, for example, DNA electrophoresis in a slab gel or capillary. Any number of detection methods can be used to read the DNA sequence as determined by the relative lengths of oligonucleotides in each of the four reactions, for example, autoradiography, UV light detection, or fluorescent dye detection. Dye termination methods are a variation of chain termination methods whereby each type of ddNTP (e.g., ddATP, ddTTP, ddCTP, ddGTP) is labeled with a different color fluorescent dye. This enables DNA to be sequenced in a single PCR reaction.

Direct RNA sequencing technology (Helicos BioSciences Corporation, Cambridge, Mass.) and transcriptome profiling using single-molecule direct RNA sequencing are described in Ozsolak et al., *Nature* 461(7265):814-818 (2009) and Ozsolak and Milos, *Methods Mol Biol* 7:51-61 (2011). True Single Molecule and Direct RNA Sequencing technologies are further described in U.S. Patent Publication Nos. 2008/0081330, 2009/0163366, 2008/0213770, 2010/0184045, 2010/0173363, 2010/0227321, 2008/0213770, and 2008/0103058 as well as U.S. Pat. Nos. 7,666,593; 7,767,400; 7,501,245; and 7,593,109, each of which is hereby incorporated by reference in its entirety.

mRNAs encoded by SMARCA4 gene can be directly sequenced by True Single Molecule and Direct RNA Sequencing technologies by utilizing specific sequencing primers that are designed based upon the SMARCA4 nucleotide sequences (e.g., as presented in SEQ ID NO's. 1, 3, 5, and 7, or which are otherwise known and readily available to those skilled in the art).

(d) Hybridization

Hybridization is another method for detecting mutations. This method involving a gene-chip or microarray customized for the SMARCA4 gene. This is particularly useful for detecting reported SMARCA4 mutations. Preferably where a chip or array comprises probes for detection of a genetic variation in SMARCA4, the chip or array comprises one or more of the probes as suitable for detection of that genetic variation.

In general the chip or array comprises a support or surface with an ordered array of binding (e.g. hybridization) sites or probes. Chip or array is in general prepared by selecting probes which comprise a given polynucleotide sequence, and then immobilizing such probes to a solid support or surface. Probes may be designed, tested and selected as described herein. In general the probes may comprise DNA sequences. In some embodiments the probes may comprise RNA sequences, or copolymer sequences of DNA and RNA. The polynucleotide sequences of the probes may also comprise DNA and/or RNA analogues, or combinations thereof. For example, the polynucleotide sequences of the probes may be full or partial fragments of genomic DNA. The polynucleotide sequences of the probes may also be synthesized nucleotide sequences, such as synthetic oligonucleotide sequences. The probe sequences can be synthesized either enzymatically in vivo, enzymatically in vitro (e.g., by PCR), or non-enzymatically in vitro.

A nucleic acid sample, e.g. amplification or fragmentation products, comprising the genetic variation(s) to be detected (target DNA) is contacted with a probe array as described herein, under conditions which allow hybridization to occur between target DNA and the corresponding probes. Specific hybridization complexes are thus formed between target nucleic acid and corresponding probes.

The hybridization of e.g. fragmentation products, with probes capable of detecting corresponding genetic variations deposited on a support may be carried out using conventional methods and devices. In one instance, hybridization is carried out using an automated hybridization station. For hybridization to occur, the e.g. fragmentation products, are placed in contact with the probes under conditions which allow hybridization to take place. Using stable hybridization conditions allows the length and sequence of the probes to be optimized in order to maximize the discrimination between genetic variations A and B, e.g. between wild type and mutant sequences, as described herein.

In some embodiments, the method relies on differential hybridization, in particular an increase in hybridization signal. The method involves formation of specific hybridization complexes between target DNA and corresponding probes. Thus target DNA bearing the wild type sequence will hybridize to the probes designed to detect the wild type sequence, whereas target DNA bearing a mutant sequence will hybridize to the probes designed to detect that mutant sequence. The hybridization complexes are detectably labelled by means described herein (e.g. the target DNA is directly labelled, or both target and probe are labelled in such a way that the label is only detectable on hybridization). By detecting the intensity of detectable label (if any) at the predetermined probe positions it is possible to determine the nature of the target DNA in the sample. In this instance the probes (also referred to as allele specific oligonucleotides, ASOs) preferably have the variable nucleotide(s) at the central position, as described herein.

To distinguish between two known alleles that differ by a single base, three oligonucleotides are necessary: Two are allele-specific oligonucleotides (ASOs) that differ from each other only in the single 3' terminal base; the first is complementary to one allele and the second is complementary to the second allele. The third oligonucleotide is complementary to the invariable sequence adjacent to the variant base. Once hybridization (and optionally post-hybridization amplification) has taken place, the intensity of detectable label at each probe position (including control probes) can be determined. The intensity of the signal (the raw intensity value) is a measure of hybridization at each probe. The intensity of detectable label at each probe position (each probe replica) may be determined using any suitable means. The means chosen will depend upon the nature of the label. In general an appropriate device, for example, a scanner, collects the image of the hybridized and developed DNA-chip. An image is captured and quantified.

Once the target DNA has been hybridized to the chip and the intensity of detectable label has been determined at the probe replica positions on the chip (the raw intensity values), it is necessary to provide a method (model) which can relate the intensity data from the chip to the genotype of the individual (otherwise known and readily available to those skilled in the art).

2. Methodology for Detecting Mutations in SMARCA4 Protein

In addition to nucleotide-based detection methods, mutations can also be identified through changes in the sequence, 3D structure and immunoreactivity of the SMARCA4 protein. Mutations such as nonsense mutation, frame shift mutation, addition or deletions often result in the loss or change of protein immunoreactivity to antibodies. Common methods for detecting these changes include western blot, immunoprecipitation, immunohistochemical analysis (IHC), immunofluorescent analysis and proteomics such as LC-MS/MS, and can be performed by those skilled in the art.

(a) Methodologies for Detecting Structural Alterations

(i) Anti-SMARCA4 Antibodies

Antibodies for detecting SMARCA4 proteins that can be used in the methods of the present disclosure are widely available commercially from, for example, LifeSpan BioSciences, Inc. (Seattle, Wash.), Antibodies Online.com (Atlanta, Ga.), PTG Labs (Chicago, Ill.), Abcam® (Cambridge, Mass.), and Santa Cruz Biotechnology (Dallas, Tex.).

Suitable antibodies can also be prepared by using standard techniques that are well known and readily available in the art. To prepare polyclonal antibodies or "antisera," an animal is inoculated with an antigen, i.e., a purified immunogenic SMARCA4 protein, or a peptide thereof. Immunoglobulins are recovered from a fluid, such as blood serum, that contains the immunoglobulins, after the animal has had an immune response. For inoculation, the antigen is preferably bound to a carrier peptide and emulsified using a biologically suitable emulsifying compound, such as Freund's incomplete adjuvant. A variety of mammalian or avian host organisms may be used to prepare polyclonal antibodies against SMARCA4 protein, or a peptide thereof.

Following immunization, immunoglobulin (Ig) can be purified from the immunized bird or mammal, e.g., goat, rabbit, mouse, rat, or donkey and the like. For certain applications, particularly certain pharmaceutical applications, it is preferable to obtain a composition in which the antibodies are essentially free of antibodies that do not react with the immunogen. This composition is composed virtually entirely of the high titer, monospecific, purified polyclonal antibodies to the immunogen.

Antibodies can be purified by affinity chromatography, using purified SMARCA4, or a peptide thereof. Purification of antibodies by affinity chromatography is generally known to those skilled in the art (see, for example, U.S. Pat. No. 4,533,630). Briefly, the purified antibody is contacted with the purified immunogen bound to a solid support for a sufficient time and under appropriate conditions for the antibody to bind to the immunogen. Such time and conditions are readily determinable by those skilled in the art. The unbound, unreacted antibody is then removed, such as by washing. The bound antibody is then recovered from the column by eluting the antibodies, so as to yield purified, monospecific polyclonal antibodies.

Monoclonal antibodies can be also prepared, using known hybridoma cell culture techniques. In general, this method involves preparing an antibody-producing fused cell line, e.g., of primary spleen cells fused with a compatible continuous line of myeloma cells, and growing the fused cells either in mass culture or in an animal species, such as a murine species, from which the myeloma cell line used was derived or is compatible. Such antibodies offer many advantages in comparison to those produced by inoculation of animals, as they are highly specific and sensitive and relatively "pure" immunochemically. Immunologically active fragments of the present antibodies are also within the scope of the present disclosure, e.g., the F(ab) fragment and scFv antibodies, as are partially humanized monoclonal antibodies.

Thus, it will be understood by those skilled in the art that the hybridomas herein referred to may be subject to genetic mutation or other changes while still retaining the ability to produce monoclonal antibody of the same desired specificity. The present disclosure encompasses mutants, other derivatives and descendants of the hybridomas.

It will be further understood by those skilled in the art that a monoclonal antibody may be subjected to the techniques of recombinant DNA technology to produce other derivative antibodies, humanized or chimeric molecules, fully human recombinant antibodies or antibody fragments which retain the specificity of the original monoclonal antibody. Such techniques may involve combining DNA encoding the immunoglobulin variable region, or the complementarity determining regions (CDRs), of the monoclonal antibody with DNA coding the constant regions, or constant regions plus framework regions, of a different immunoglobulin, for example, to convert a mouse-derived monoclonal antibody into one having largely human immunoglobulin characteristics (see EP 184187A, 2188638A, herein incorporated by reference).

A biological sample, e.g., a physiological sample that comprises cancer cells from a patient may be lysed to yield an extract which comprises cellular proteins. Alternatively, intact cells, e.g., a tissue sample such as paraffin embedded and/or frozen sections of biopsies, are permeabilized in a manner that permits macromolecules, e.g., antibodies, to enter the cell. The antibodies are then incubated with cells, including permeabilized cells, e.g., prior to flow cytometry, nuclei or the protein extract, e.g., in a western blot, so as to form a complex. The presence, amount and location of the complex is then determined or detected.

(ii) Western Blot

The western blot (a/k/a protein immunoblot) is a widely accepted analytical technique used to detect specific proteins in the given sample of tissue homogenate or extract. It uses gel electrophoresis to separate native proteins by 3-D structure or denatured proteins by the length of the polypeptide. The proteins are then transferred to a membrane (typically nitrocellulose or PVDF), where they are stained with antibodies specific to the target protein. There are now many recompound companies that specialize in providing snyinofird (both monoclonal and polyclonal antibodies) against tens of thousands of different proteins. WO 2014085698.

Western blot can also be used to detect SMARCA4 mutations because often loss-of-function mutations in SMARCA4 are associated with the loss of amino acids, with the gain of amino acids, and with the change of amino acids of SMARCA4 that result in the change of SMARCA4's immunoreactivity to certain antibodies.

Samples can be taken from whole tissue or from cell culture. Solid tissues are first broken down mechanically using a bender larger sample volumes), using a homogenizer (smaller volumes), or by sonication. Cells may also be broken open by one of the above mechanical methods. However, virus or environmental samples can be the source of protein and thus western blotting is not restricted to cellular studies only.

Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing and degradation.

A combination of biochemical and mechanical techniques—comprising various types of filtration and centrifugation—can be used to separate different cell compartments and organelles.

The proteins of the sample can be separated using gel electrophoresis, using such characteristics as isoelectric point (pI), molecular weight, electric charge, or a combination of these. The nature of the separation depends on the treatment of the sample and the nature of the gel. This is a very useful way to identify a protein.

Many modern embodiments of this technique are available, such as that disclosed for example in Silva, J. M., McMahon, M. The Fastest Western in Town: A Contemporary Twist on the Classic Western Blot Analysis. *J. Vis. Exp.* (84), e51149, doi:10.3791/51149 (2014).

(iii) Immunoprecipitation

As used herein, the term "immunoprecipitation" refers to a technique for precipitating a protein antigen out of solution using an antibody that specifically binds to that particular protein. This process can be used to isolate and concentrate a particular protein from a sample containing a multitude of different proteins. Immunoprecipitation requires that the antibody be coupled to a solid substrate at some point in the procedure.

Immunoprecipitation can be used to detect SMARCA4 mutations because often loss-of-function mutations in SMARCA4 are associated with the loss of amino acids, with the gain of amino acids, and with the change of amino acids of SMARCA4 that result in the change of SMARCA4's immunoreactivity to certain antibodies.

Individual protein immunoprecipitation involves using an antibody that is specific for a known protein, e.g., SMARCA4, to isolate that particular protein out of a solution containing many different proteins. These solutions will often be in the form of a crude lysate of a tissue sample.

(iv) Immunohistochemical Detection

As used herein, the terms "immunohistochemistry" or "IHC" refer to the detection of SMARCA4 protein in a cell or a tissue section by exploiting the specific binding of a SMARCA4 antibody to corresponding protein in a cancer cell or tissue. Immunohistochemical staining is widely used in the diagnosis of abnormal cells such as those found in cancerous tumors and to determine the distribution and localization of biomarkers and differentially expressed proteins in different parts of a biological tissue. Immunohistochemical detection is described for example in *Am J. Physiol Regul Integr Comp Physiol.* 2011 September; 301(3): R632-R640.

Visualizing an antibody-antigen interaction can be accomplished in a number of ways. In the most common instance, an antibody is conjugated to an enzyme, such as peroxidase, that can catalyze a color-producing reaction. Alternatively, the antibody can also be tagged to a fluorophore, such as fluorescein or rhodamine.

The antibodies used for specific detection of SMARCA4 can be polyclonal or monoclonal. Polyclonal antibodies are made by injecting animals with peptide Ag and, after a secondary immune response is stimulated, isolating antibodies from whole serum. Thus, polyclonal antibodies are a heterogeneous mix of antibodies that recognize several epitopes. Monoclonal antibodies show specificity for a single epitope and are therefore considered more specific to the target antigen than polyclonal antibodies.

For IHC detection strategies, antibodies are classified as primary or secondary recompounds. Primary antibodies are raised against an antigen of interest and are typically unconjugated (unlabeled), while secondary antibodies are raised against immunoglobulins of the primary antibody species. The secondary antibody is usually conjugated to a linker molecule, such as biotin, that then recruits reporter molecules, or the secondary antibody itself is directly bound to the reporter molecule.

Reporter molecules vary based on the nature of the detection method, the most popular being chromogenic and fluorescence detection mediated by an enzyme or a fluorophore, respectively. With chromogenic reporters, an enzyme label is reacted with a substrate to yield an intensely colored product that can be analyzed with an ordinary light microscope. While the list of enzyme substrates is extensive, alkaline phosphatase (AP) and horseradish peroxidase (HRP) are the two enzymes used most extensively as labels for protein detection. An array of chromogenic, fluorogenic and chemiluminescent substrates is available for use with either enzyme, including DAB or BCIP/NBT, which produce a brown or purple staining, respectively, wherever the enzymes are bound.

Reaction with DAB can be enhanced using nickel, producing a deep purple/black staining. Fluorescent reporters are small, organic molecules used for IHC detection and traditionally include FITC, TRITC, and AMCA, while commercial derivatives, including the Alexa Fluors and Dylight Fluors, show similar enhanced performance but vary in price. For chromogenic and fluorescent detection methods, densitometric analysis of the signal can provide semi- and fully quantitative data, respectively, to correlate the level of reporter signal to the level of protein expression or localization.

The direct method is a one-step staining method and involves a labeled antibody (e.g., FITC-conjugated antiserum reacting directly with the antigen in tissue sections. While this technique utilizes only one antibody and therefore is simple and rapid, the sensitivity is lower due to little signal amplification, in contrast to indirect approaches.

The indirect method involves an unlabeled primary antibody (first layer) that binds to the target antigen in the tissue and a labeled secondary (second layer) that reacts with the primary antibody. As disclosed, herein, the secondary antibody must be raised against the IgG of the animal species in which the primary antibody has been raised. This method is more sensitive than direct detection strategies because of signal amplification due to the binding of several secondary antibodies to each primary antibody if the secondary antibody is conjugated to the fluorescent or enzyme reporter.

Further amplification can be achieved if the secondary antibody is conjugated to several biotin molecules, which can recruit complexes of avidin-streptavidin, or NeutrAvidin protein bound-enzyme. The difference between these three biotin-binding proteins is their individual binding affinity to endogenous tissue targets leading to nonspecific binding and high background; the ranking of these proteins based on their nonspecific binding affinities, from highest to lowest, is: 1) avidin, 2) streptavidin and 3) Neutravidin protein.

The indirect method, aside from its greater sensitivity, also has the advantage that only a relatively small number of standard conjugated (labeled) secondary antibodies needs to be generated. For example, a labeled secondary antibody raised against rabbit IgG, which can be purchased "off the shelf," is useful with any primary antibody raised in rabbit. With the direct method, it would be necessary to label each primary antibody for every antigen of interest.

After immunohistochemical staining of the target antigen, a second stain is often applied to provide contrast that helps the primary stain stand out. Many of these stains show specificity for discrete cellular compartments or antigens, while others will stain the whole cell. Both chromogenic and fluorescent dyes are available for IHC to provide a vast array of recompounds to fit every experimental design, and include: hematoxylin, Hoechst stain, and DAPI are commonly used.

(v) Immunofluorescent Detection

As used herein, the term "immunofluorescence" refers to a technique used for light microscopy with a fluorescence microscope is used primarily on microbiological samples. This technique uses the specificity of antibodies to their antigen to target fluorescent dyes to specific biomolecule targets within a cell, and therefore allows visualization of the distribution of the target molecule through the sample. Immunofluorescence is a widely used example of immunostaining and is a specific example of immunohistochemistry that makes use of fluorophores to visualize the location of the antibodies. Immunofluorescent detection is described in *Am J Physiol Regul Integr Comp Physiol* 301(3): R632-R640 (2011).

Immunofluorescence can be used on tissue sections, cultured cell lines, or individual cells, and may be used to analyze the distribution of proteins, glycans, and small biological and non-biological molecules. Immunofluorescence can be used in combination with other, non-antibody methods of fluorescent staining, for example, use of DAPI to label DNA. Several microscope designs can be used for analysis of immunofluorescence samples; the simplest is the epifluorescence microscope, and the confocal microscope is also widely used. Various super-resolution microscope designs that are capable of much higher resolution can also be used.

There are two classes of immunofluorescence techniques, primary (or direct) and secondary (or indirect). Primary, or direct, immunofluorescence uses a single antibody that is chemically linked to a fluorophore. The antibody recognizes the target molecule and binds to it, and the fluorophore it carries can be detected via microscopy. This technique has several advantages over the secondary (or indirect) protocol below because of the direct conjugation of the antibody to the fluorophore. This reduces the number of steps in the staining procedure making the process faster and can reduce background signal by avoiding some issues with antibody cross-reactivity or non-specificity. However, since the number of fluorescent molecules that can be bound to the primary antibody is limited, direct immunofluorescence is less sensitive than indirect immunofluorescence.

Secondary, or indirect, immunofluorescence uses two antibodies; the unlabeled first (primary) antibody specifically binds the target molecule, i.e. SMARCA4, and the secondary antibody, which carries the fluorophore, recognizes the primary antibody and binds to it. Multiple secondary antibodies can bind a single primary antibody. This provides signal amplification by increasing the number of fluorophore molecules per antigen. This protocol is more complex and time consuming than the primary (or direct) protocol above, but it allows more flexibility because a variety of different secondary antibodies and detection techniques can be used for a given primary antibody.

(b) Detection of Mutations Through Proteomic Analysis

Mass spectrometry-based proteomics can be employed to detect SMARCA4 protein mutations and post-translational modifications (PTM). Recent technological advances allow thousands of proteins to be routinely identified from sub-milligram quantities of tissues or cells. More important, targeted-proteomics with prespecified protein candidates have been used to study protein mutation and PTM in a variety of proteins. Increased depth of proteome coverage lends itself to the investigation of molecular signatures. For instance, in cancer, thousands of mutations have been identified but the precise relationship between genomic variation and cancer phenotype remains largely unclear. Individual mutations may bring about proteomic changes that otherwise would not be predicted based on known gene function.

Several choices of instrumentation exist for proteomics-based analysis. The first, shotgun proteomics, employs liquid chromatography-tandem mass spectrometry (LC-MS/MS) and provides a nondirected, global inventory of proteomes, together with quantitative assessments of protein abundances. The second proteomics approach is targeted analysis of individual proteins by multiple reaction monitoring (MRM) mass spectrometry intensity measurement of their constituent peptides.

In a typical experiment, a cancer cell and a non-cancer control cell are cultured separately. Cells are then lysed, and cellular total protein is collected. In some instances, this protein mixture undergoes further purification, e.g. immunoprecipitation to isolating certain proteins(s) or isoelectric focusing electrophoresis. However, because the improved equipment sensitivity, this may not be required. Usually proteins are then digested (e.g., trypsin digestion) and the resultant peptides are lyophilized to be used for mass spec analysis.

LC-MS/MS shotgun proteomic analyses can be performed on mass spectrometer (e.g., an LTQ XL by Thermo Fisher Scientific) equipped with a nanospray source. For example, peptides from a protein mixture containing SMARCA4 can be separated on a packed capillary tip (Polymicro Technologies, 100 mm×11 cm) with Jupiter C18 resin (5 mm, 300 Å, Phenomenex) using an in-line solid-phase extraction column (100 mm×6 cm) packed with the same C18 resin using a flit generated with liquid silicate Kasil 1.18 Mobile phase A consisted of 0.1% formic acid and mobile phase B consisted of 0.1% formic acid in 90% acetonitrile. A 90-min gradient is carried out with a 30-min washing period (100% A) to allow for solid-phase extraction and removal of any residual salts. Following the washing period, the gradient is increased to 25% B by 35 min, followed by an increase to 90% B by 50 min and held for 9 min before returning 95% A. MS/MS spectra of the peptides are acquired using data-dependent scanning in which one full MS spectrum (mass range 400-2000 m/z) is followed by five MS/MS spectra. MS/MS spectra are recorded using dynamic exclusion of previously analyzed precursors for 60 s with a repeat of 1 and a repeat duration of 1. MS/MS spectra were generated by collision-induced dissociation of the peptide ions at normalized collision energy of 35% to generate a series of b- and y-ions as major fragments. Biological samples from 3 independent cell cultures were injected in duplicate for a total of 6 replicate measurements for a cancer cell culture and a non-cancer cell culture.

Data from LC-MS/MS can be analyzed by a variety of methods by those skilled in the art. For example, MS/MS scans are transferred to mzML file. The resulting mzML files are then searched against the Human IPI database using commercially available software. The database search is configured to look for both fully tryptic and semitryptic peptides with a precursor mass/charge (m/z) tolerance of 1.25 and a fragment m/z tolerance of 0.5. Carboxamidomethylation of cysteines is included as static modification, and oxidation of methionine as a dynamic modification in the search criteria, while any number of missed cleavages was allowed. The IDpicker algorithm is used to assemble the set of peptides identified into a minimal list of proteins that could explain the observed spectral data set. A minimum of two peptides per protein is required for valid protein identification with a peptide false discovery rate (FDR) of 5%. Statistically significant differences in protein spectral counts between different groups (i.e., tumor cells and normal cells from a SCCOHT patient) are calculated using commercially available software.

Similarly, targeted proteomics can be done with LCMRM-MS. Cell line samples for LCMRM-MS are prepared as outlined above for LC-MS/MS proteomics, except peptide extracts are not subjected to further fractionation by IP or IEF. Peptide samples from each cell line are resuspended in 0.1% formic acid at 0.25 µg/µL and analyzed in triplicate (2 µL injection volume) on a triple quadrupole mass spectrometer (e.g. TSQ Vantage from Thermo-Fisher) equipped with a nanospray source. The mobile phase consists of 0.1% formic acid in either HPLC grade water (A) or 90% acetonitrile (B). An 80-min gradient is carried out with a 15-min washing period (100% A). Following the washing period, the gradient is increased to 60% B by 43 min, followed by an increase to 95% B by 49 min and held for 11 min before returning 97% A. Usually, a stable isotope labeled peptide (e.g. β-actin peptide GYSFTTTAER (SEQ ID NO: 17)) is used as an internal standard (60 fmol/injection) for relative quantification of target proteins by the Labeled Reference Peptide (LRP) method. The integrated chromatographic peak areas for the transitions of each targeted peptide were obtained from Skyline, and summed, normalized to summed peak areas for the (β-actin internal standard.

For either LC-MS/MS or LC-MRM-MS, peptide sequence of SMARCA4 protein will be obtained for both cancer cell sample and non-cancer normal cell sample. Comparison of SMARCA4 peptide sequence between the two samples, and comparing both against reference sequences, can detect somatic and germline mutations in SMARCA4 amino acid sequence. Further analysis of the sequence can detect mutations for insertion, deletion or point mutations.

3. Methodologies for Measuring SMARCA4 Gene Expression

Reduced expression of the SMARCA4 gene results in reduced cellular availability of SMARCA4 and, as reported herein, causes growth a cancer cell. Because of this and because SMARCA4 loss of expression characterizes SCCOHT, expression of SMARCA4 can be used a diagnostic marker for SCCOHT.

SMARCA4 gene expression levels (i.e., mRNA levels) can be measured by employing such methodology as real-time PCR and electrophoresis. SMARCA4 protein levels can be readily measured by ELISA, western blot, and proteomics. SMARCA4 expression can also be quantified in a tumor sample from a cancer patient through IHC and PCR.

In addition to the expression of SMARCA4, the same methods of measuring cellular gene and protein levels can also be to evaluate SMARCA4 downstream target genes including CDH1, CDH3, EHF, RRAD and ML-IAP.

4. Methodologies for Measuring SMARCA4 Complex Formation

SMARCA4 may exert its effects on cancer cell proliferation through its participation in the protein-protein complexes such as SWI/SNF and BAF complexes. Therefore, in addition to SMARCA4 expression, cellular levels of downstream SWI/SNF and BAF can also be used as diagnostic factors for SCCOHT.

Protein-protein complexes can be quantified by a variety of methods by those skilled in the art, including ELISA with antibodies recognizing different components of the complex, preferably with one antibody recognizing SMARCA4 in the complex. Protein-protein complexes can also be measured in situ by molecular imaging methods using immunofluorescent- or immunoradioactive-probes. Double or triple staining with such probes can be analyzed by standard imaging software to quantify the cellular or tissue levels of intact protein-protein complexes such as SWI/SNF and BAF.

Additionally, protein-protein complexes can be detected and quantified in cell culture or in a tumor tissue sample with fluorescence resonance energy transfer (FRET) which relies on the proximity of two immunofluorescent probes, and can be performed by those skilled in the art.

Methods for Inhibiting the Growth of an SCCOHT Cancer Cell and for the Treatment of a Patient Afflicted with Ovarian Cancer The present disclosure provides methods for inhibiting the growth of cancer cells and for the treatment of cancers, including ovarian cancers, such as small cell carcinomas of the ovary (SCCO), in particular SCCO hypercalcemic type (SCCOHT), which cancers are associated with a cancer cell exhibiting reduced or undetectable SMARCA4 gene expression and/or with reduced or undetectable SMARCA4 protein levels and/or protein function, which methods include contacting a cancer cell or administering to patient afflicted with a cancer, such as an ovarian cancer, in particular SCCOHT, one or more compounds, including one or more polynucleotides, polypeptides, and/or small molecules, such as, for example, one or more EZH2 (histone methyltransferase enhancer of Zeste homolog 2) inhibitors (Such as GSK-343, EPZ-6438-additional such inhibitors such as GSK 126 are described in the literature or can be identified using methodology of e.g., Garapathy—Rao et al. Chem. Biol. 2013, Nov. 21; 20(11):1329-39 incorporated herein by reference in its entirety for all purposes and Qi, W. et al PNAS, 2013, www.pnas.org/cgi/doi/10.1073/pnas.1210371110 incorporated herein by reference in its entirety for all purposes) or bromodomain inhibitors (Miller, S. Med. Chem Commun. 2014, 5, 288-296 incorporated herein by reference in its entirety for all purposes) that can restore SMARCA4 gene expression and/or SMARCA4 protein levels and/or protein function and/or can otherwise inhibit the tumorigenic effect of a SMARCA4 gene mutation, or events triggered thereby, thereby, slowing or stopping the growth of the cancer cell. Indeed it is hypothesized and anticipated in light of evidence and experiments described herein that reduction or elimination of SMARCA4 renders these tumors more sensitive to such drugs. Exemplary EZH2 inhibitor compounds which are commercially available (e.g., from Active Biochem, or Selleckchem or Epizyme and other such specialty suppliers) are disclosed below:

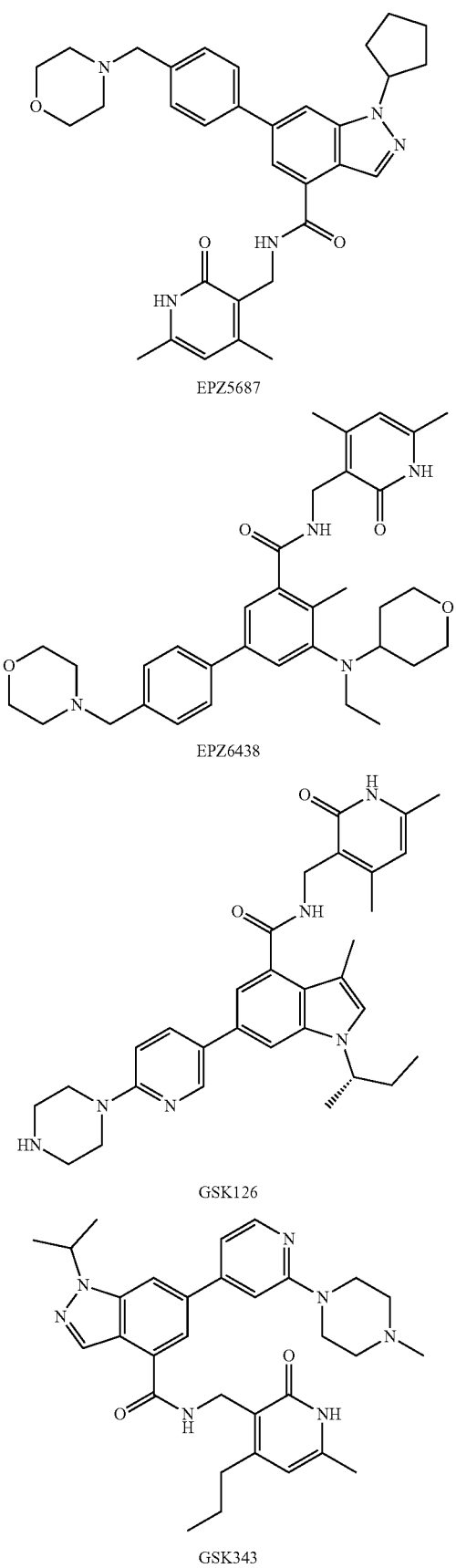

EPZ5687

EPZ6438

GSK126

GSK343

Exemplary Structures of EZH2 Small Molecule Inhibitors Identified by Garapaty-Rao (Chem Biol. 2013 Nov. 21; 20(11): 1329-39)

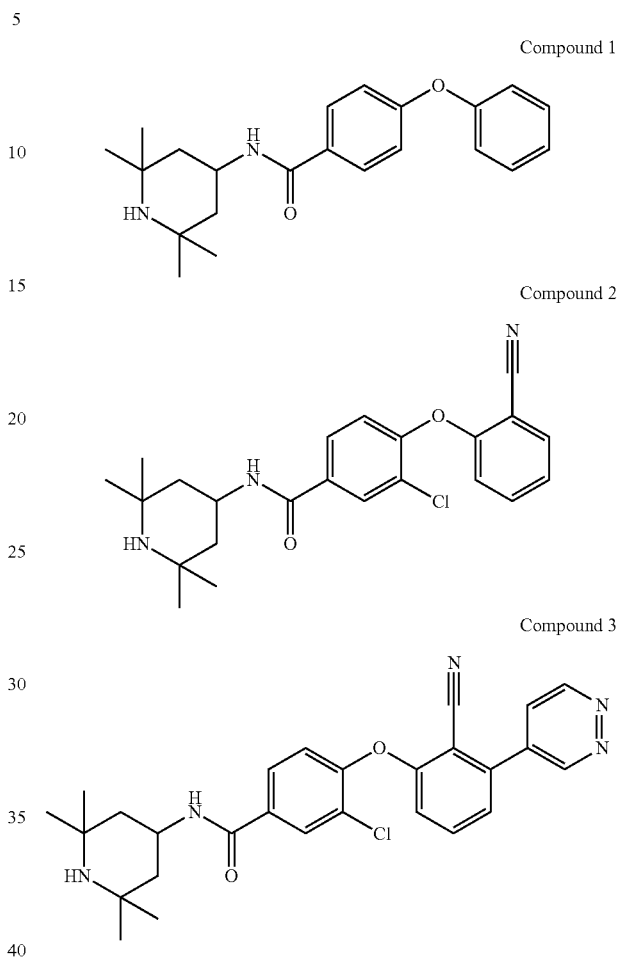

Compound 1

Compound 2

Compound 3

As described herein, mutations, including loss-of-function mutations, within the SMARCA4 gene were identified in tissue samples from SCCOHT patients. Those mutations were found to cause the SMARCA4 gene to either encode reduced or undetectable levels of SMARCA4 mRNA, to encode SMARCA4 mRNA that cannot be transcribed into SMARCA4 protein, and/or to encode mRNA that does not encode functional SMARCA4 protein. Such SMARCA4 gene mutations include insertion mutations, deletion mutations, frame shift mutations, splice site mutations, nonsense mutations, and missense mutations, which result in reduced or undetectable levels of SMARCA4 protein or SMARCA4 protein having reduced or undetectable functionality. For example most of the mutations characterized in the tissue samples from the 12 SCCOHT patients studied included non-sense, frameshift, and slice site mutations all of which were predicted to generate non-functional carboxy-terminal truncations of the SMARCA4 protein lacking in one or more critical domains for protein functionality including, for example the SNF2_N and helicase domains that are essential for SMARCA4 functionality.

Based in part upon these observations, the present disclosure provides therapeutic regimen that in some embodiments employ one or more compound, such as a small molecule, polynucleotide, or polypeptide that when contacted with a cell from a SCCOHT patient or when administered in vivo to a SCCOHT patient is capable of restoring the expression of one or both SMARCA4 alleles and or restoring levels and/or functionality of SMARCA4 protein.

Thus, the present disclosure provides compounds and compositions, including pharmaceutical compositions, containing those compounds, which compounds and compositions may be advantageously employed in the presently-disclosed methods for inhibiting the growth of cancer cells and for the treatment of cancers, including ovarian cancers, such as small cell carcinomas of the ovary (SCCO), in particular SCCO hypercalcemic type (SCCOHT), which cancers are associated with a cancer cell exhibiting reduced or undetectable SMARCA4 gene expression and/or with reduced or undetectable SMARCA4 protein levels and/or protein function. Exemplified herein are compounds, including polynucleotides, polypeptides, and small molecules that can be used to restore SMARCA4 gene expression and/or function and/or restore SMARCA4 protein level and/or function and, thereby, slow or stop the growth of a cancer cell.

A wide variety of methodologies are known in the art that can be adapted advantageously to permit at least the partial restoration of SMARCA4 gene and/or protein functionality. For example, the present disclosure contemplates that suitable therapeutic regimen can include gene therapy, protein therapy, cell therapy in addition to or in place of traditional drug therapies, including conventional chemotherapies, such as intraperitoneal (IP) chemotherapy (e.g., carboplatin, paclitaxel (Taxol), liposomal doxorubicin (Caelyx, Myocet or Doxil), Gemcitabine, cisplatin, topotecan, etoposide, cyclophosphamide)), immunotherapies (e.g., bevacizumab (Avastin)), and/or radiation therapies. These therapies can be used independently or together with one or more ezh2 inhibitors and/or one or more JQ1 bromodomain inhibitors, in addition to and/or instead of one or more traditional cancer treatments such as chemotherapy, immunotherapy, and radiation therapy.

Three types of CRISPR/Cas systems have been described (Makarova et al., Nat. Rev. Microbiol. 9, 467 (2011); Makarova et al., Biol. Direct 1, 7 (2006); Makarova et al., Biol. Direct 6, 38 (2011)). Recent work has shown that Type II CRISPR/Cas systems can be engineered to direct targeted double-stranded DNA breaks in vitro to specific sequences by using a single "guide RNA" with complementarity to the DNA target site and a Cas9 nuclease (Jinek et al., Science 2012; 337:816-821). This targetable Cas9-based system also works efficiently in cultured human cells (Mali et al., Science. 2013 Feb. 15; 339(6121):823-6; Cong et al., Science. 2013 Feb. 15; 339(6121):819-23) and in vivo in zebra fish (Hwang and Fu et al., Nat Biotechnol. 2013 March; 31(3): 227-9) for inducing targeted alterations into endogenous genes. Recently, it has been reported to have been successful in mice (Yin, H. et al, Nature Biotechnology 32, 551-553 (2014); doi:10.1038/nbt.2884). these methods can be used to correct the defects in SMARCA4 genes.

Further work described in U.S. Published Patent Applications 20140377868; 20140357530; 20140356958; 20140342457 and 20140356959 involves targeting specific sequences in eukaryotic cells in vivo in order to alter their sequence and/or upregulating their expression.

It is contemplated that nucleic acids, in particular polynucleotides including cDNAs, which encode the wild-type SMARCA4 protein can be employed to complement the defective SMARCA4 gene. Such gene therapy approaches include delivery technologies that permit the targeting, cellular uptake, and expression of a wild-type SMARCA4 cDNA. Such delivery technologies include, for example, retroviral vectors, adeno-viral vectors, a vaccinia-viral vectors, liposomes, and/or nano-particles that containing SMARCA4 gene.

The present disclosure also contemplates that wild-type SMARCA4 protein can be delivered directly to a cell through the targeting of one or more liposomes or a nanoparticles that contain a SMARCA4 protein alone or in combination with a targeting moiety that facilitates the delivery of the SMARCA4 protein payload to the desired cells, in particular to ovarian carcinoma cells, including SCCOHT cells.

Alternatively cells can be generated by employing recombinant DNA technology to engineer them to express a wild-type SMARCA4 protein. Within certain aspects, the nucleic acid encoding a wild-type SMARCA4 protein can be modified by the addition of a secretory signal, regulatory sequence, and targeting moieties so that the SMARCA4 protein can be specifically targeted to the SCCOHT cells, so that the expression of the SMARCA4 protein can be regulated to ensure that it is delivered at an appropriate time or when it reaches a desired target site, and so that the SMARCA4 protein can exit the cell by exploiting native intracellular protein transport machinery.

Within still further aspects, the present disclosure provides small molecules, antibodies, antisense, shRNA, siRNA, and other RNAi-based technologies that permit the delivery of target specific molecules that can promote the up or downregulation of genes and/or mRNAs of interest. By way of example, not limitation, it has been observed that the expression of SMARCA2 and SMARCA4 are closely associated and that the down-regulation of SMARCA2 can promote the up-regulation of SMARCA4. Thus, it is contemplated that suitable therapeutics for enhancing the expression of SMARCA4 can include such small molecules, antibodies, antisense, shRNA, siRNA, and other RNAi-based technologies that facilitate the downregulation of SMARCA2.

In a similar fashion, it is well known that wild-type SMARCA4 plays a primary role in regulating the expression of downstream genes including, for example, the CDH1, CDH3, EHF, RRAD, and ML-IAP genes. Thus, the present disclosure contemplates therapeutics, including small molecule, polynucleotide, and polypeptide therapeutics that can complement the lost gene regulatory function of mutated SMARCA4 in ovarian cancer cells, especially SCCOHT cells by facilitating the upregulation of the CDH1, CDH3, EHF, RRAD, and/or ML-IAP genes. Exemplary suitable such compounds include small molecules, antibodies, antisense, shRNA, siRNA, and other RNAi technologies that can modulate the expression of one or more genes that encode factors that can be exploited to induce the upregulation of the CDH1, CDH3, EHF, RRAD, and/or ML-IAP genes.

Therapeutic compounds can be administered according to therapeutic protocols well known in the art. It will be apparent to those skilled in the art that the administration of the disclosed therapeutic compound can be varied depending on the disease being treated and the known effects of such therapeutic compounds on that disease. Also, in accordance with the knowledge of the skilled clinician, the therapeutic protocols (e.g., dosage amounts and times of administration) can be varied in view of the observed effects of the administered therapeutic compounds on the patient, and in view of the observed responses of the disease to the administered therapeutic compounds.

The amount of a therapeutic compound that will be effective in the treatment, inhibition, and/or prevention of a cancer associated with dysfunctional or deficient SMARCA4 can be determined by standard clinical techniques. In vitro assays may optionally be employed to help identify optimal dosage ranges. The precise dose to be employed in the formulation will also depend on the route of administration, and the seriousness of the condition being treated. Effective doses may be extrapolated from dose-response curves derived from in vitro or animal model test systems.

The compounds or compositions of the present disclosure can be tested in vitro, and then in vivo for the desired therapeutic or prophylactic activity, prior to use in humans. For example, in vitro assays to demonstrate the therapeutic or prophylactic utility of a SMARCA4-promoting therapeutic compound include the effect of the therapeutic compound on a cell line or on a patient tissue sample, wherein the compound restores a direct or indirect function of SMARCA4. The effect of a SMARCA4-promoting therapeutic compound on the cell line and/or tissue sample can be determined utilizing techniques known to those of skill in the art including, but not limited to proliferation and survival assays. In accordance with the present disclosure, in vitro assays that can be used to determine whether administration of a specific SMARCA4-promoting therapeutic compound is indicated, include in vitro cell culture assays in which a patient tissue sample is grown in culture, and exposed to or otherwise administered a cytotoxic compound, and the effect of such SMARCA4-promoting therapeutic compound upon the tissue sample is observed.

The present disclosure provides methods of treatment and inhibition by administration to a patient of an effective amount of a SMARCA4-promoting therapeutic compound or composition as described herein. In one aspect, the SMARCA4-promoting therapeutic compound is substantially purified such that the compound is substantially free from substances that limit its effect or produce undesired side-effects.

Various delivery systems are known and can be used to administer a composition of the present disclosure, for example, encapsulation in liposomes, microparticles, microcapsules, receptor-mediated endocytosis (see, e.g., Elsabahy et al., *Current Drug Delivery* 8(3):235-244 (2011) for a general description of viral and non-viral nucleic acid delivery methodologies, Wu and Wu, *J. Biol. Chem.* 262:4429-4432 (1987)), and the like as will be known by one of skill in the art.

Liposomal delivery methodologies are described in Metselaar et al., *Mini Rev. Med. Chem.* 2(4):319-29 (2002); O'Hagen et al., *Expert Rev. Vaccines* 2_(2:269-83 (2003); O'Hagan, *Curr. Drug Targets Infect. Disord.* 1(3):273-86 (2001); Zho et al., *Biosci Rep.* 22(2):355-69 (2002); Chikh et al., *Biosci Rep.* 22(2):339-53 (2002); Bungener et al., *Biosci. Rep.* 22(2):323-38 (2002); Park, *Biosci Rep.* 22(2):267-81 (2002); Ulrich, *Biosci. Rep.* 22(2):129-50; Lofthouse, *Adv. Drug Deliv. Rev.* 54(6):863-70 (2002); Zhou et al., *J. Immunother.* 25(4):289-303 (2002); Singh et al., *Pharm Res.* 19(6):715-28 (2002); Wong et al., *Curr. Med. Chem.* 8(9):1123-36 (2001); and Zhou et al., *Immunomethods* (3):229-35 (1994).

Nanoparticle delivery methodologies, including gold, iron oxide, titanium, hydrogel, and calcium phosphate nanoparticle delivery methodologies, are described in Wagner and Bhaduri, *Tissue Engineering* 18(1): 1-14 (2012) (describing inorganic nanoparticles); Ding et al., *Mol Ther* e-pub (2014) (describing gold nanoparticles); Zhang et al., *Langmuir* 30(3):839-45 (2014) (describing titanium dioxide nanoparticles); Xie et al., *Curr Pharm Biotechnol* 14(10):918-25 (2014) (describing biodegradable calcium phosphate nanoparticles); Sizovs et al., *J Am Chem Soc* 136(1):234-40 (2014) (describing sub-30 monodisperse oligonucleotide nanoparticles).

Herpes Simplex Virus vectors for the delivery of nucleic acids to target cells have been reviewed in Anesti and Coffin, *Expert Opin Biol Ther* 10(1):89-103 (2010); Marconi et al., Adv Exp Med Biol 655:118-44 (2009); and Kasai and Saeki, *Curr Gene Ther* 6(3):303-14 (2006). Lentiviral vectors for the delivery of nucleic acids to target cells have been reviewed in Primo et al., *Exp Dermatol* 21(3):162-70 (2012); Staunstrup and Mikkelsen, *Curr Gene Ther* 11(5): 350-62 (2011); and Dreyer, *Mol Biotechnol* 47(2): 169-87 (2011). Adenovirus vectors for the delivery of nucleic acids to target cells have been reviewed in Huang and Kamihira, *Biotechnol Adv.* 31(2):208-23 (2013); Alemany, *Adv Cancer Res* 115:93-114 (2012); Kaufmann and Nettelbeck, *Trends Mol Med* 18(7):365-76 (2012); and Mowa et al., *Expert Opin Drug Deliv* 7(12):1373-85 (2010). Adeno-associated virus (AAV) vectors for the delivery of nucleic acids to target cells have been reviewed in Li et al., *J. Control Release* 172(2):589-600 (2013); Hajitou, *Adv Genet* 69:65-82 (2010); McCarty, *Mol Ther* 16(10):1648-56 (2008); and Grimm et al., *Methods Enzymol* 392:381-405 (2005).

Methods of systemic administration include, but are not limited to, intradermal, intramuscular, intraperitoneal, intravenous, subcutaneous, intranasal, and oral routes. The SMARCA4-promoting therapeutic compounds or compositions may be administered by any convenient route, for example by infusion or bolus injection, by absorption through epithelial or mucocutaneous linings (e.g., oral mucosa, rectal and intestinal mucosa, etc.) and may be administered together with other therapeutically effective compounds. Pulmonary administration can also be employed, for example, by use of an inhaler or nebulizer, and formulation with an aerosolizing compound.

Local modes of administration are also contemplated. For example, it may be desirable to introduce the SMARCA4-promoting therapeutic compounds or compositions into the tumor by any suitable means, including in situ depot administration or injection. In situ depot administration may be facilitated by an intraventricular catheter, for example, attached to a reservoir, such as an Ommaya reservoir. Other localized administration methods include without limitation local infusion during surgery, topical application, by injection, by means of a an implant, said implant being for example made from a porous, non-porous, or gelatinous material, including membranes, such as sialastic membranes, or fibers.

The SMARCA4-promoting therapeutic compounds can be delivered in a vesicle, such as a liposome (Langer, *Science* 249:1527-1533 (1990)) or in a controlled release system. A controlled release system can be placed in proximity of the therapeutic target, thus requiring only a fraction of the systemic dose (see, e.g., Goodson, in *Medical Applications of Controlled Release*, Vol. 2, pp. 115-138 (1984)).

It will be understood that, unless indicated to the contrary, terms intended to be "open" (e.g., the term "including" should be interpreted as "including but not limited to," the term "having" should be interpreted as "having at least," the term "includes" should be interpreted as "includes but is not limited to," etc.). Phrases such as "at least one," and "one or more," and terms such as "a" or "an" include both the singular and the plural.

It will be further understood that where features or aspects of the disclosure are described in terms of Markush groups, the disclosure is also intended to be described in terms of any individual member or subgroup of members of the Markush group. Similarly, all ranges disclosed herein also encompass all possible sub-ranges and combinations of sub-ranges and that language such as "between," "up to," "at least," "greater than," "less than," and the like include the number recited in the range and includes each individual member.

All references cited herein, whether supra or infra, including, but not limited to, patents, patent applications, and patent publications, whether U.S., PCT, or non-U.S. foreign, and all technical and/or scientific publications are hereby incorporated by reference in their entirety.

While various embodiments have been disclosed herein, other embodiments will be apparent to those skilled in the art. The various embodiments disclosed herein are for purposes of illustration and are not intended to be limiting, with the true scope and spirit being indicated by the claims.

Figure 10:
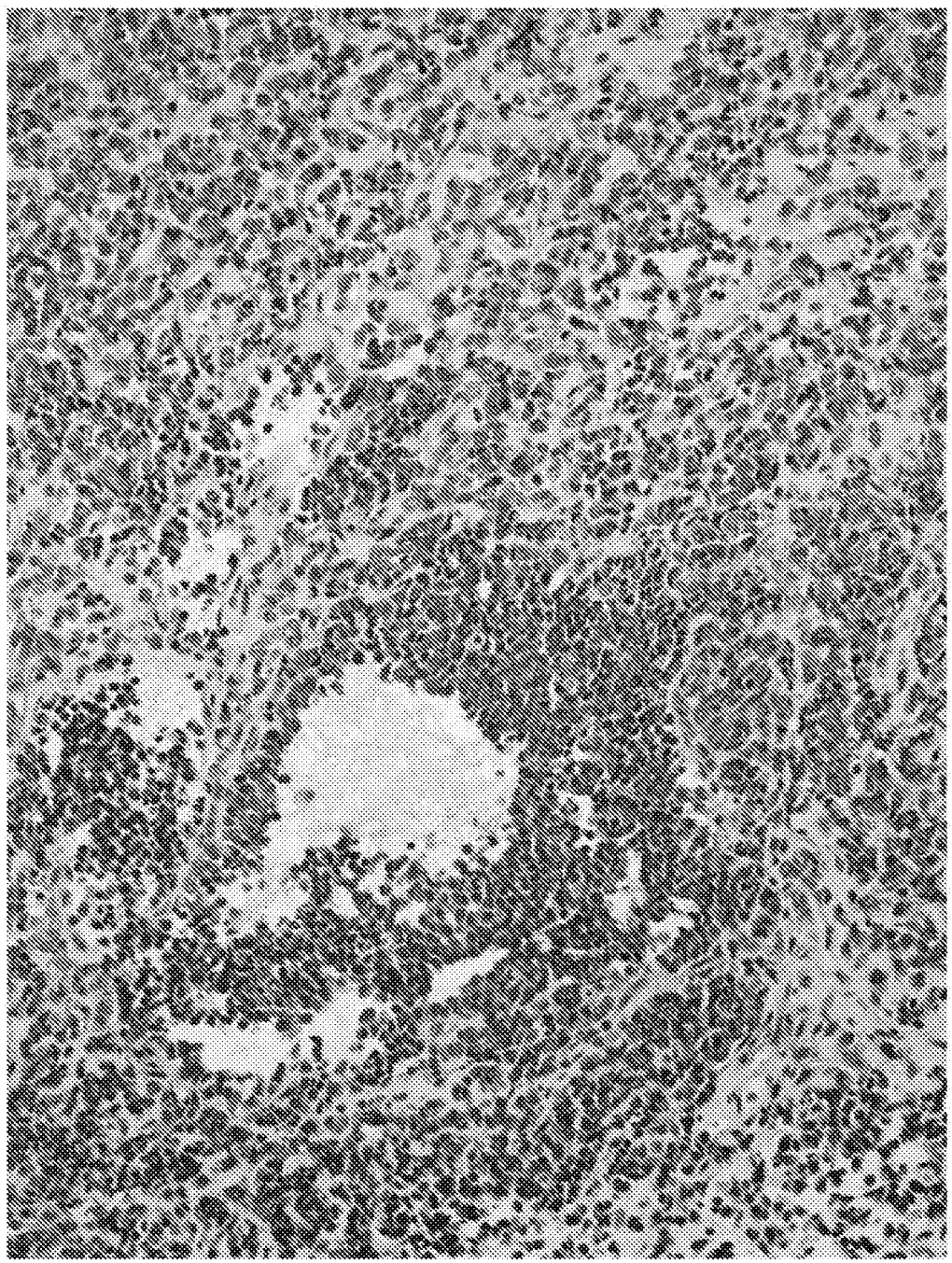
FIG. 10 is an immunohistochemistry (IHC) image showing histopathological features of a small cell carcinoma of the ovary, hypercalcemic type (SCCOHT). The typical histopathological features of SCCOHT, including a combination of small neoplastic cells forming a pseudofollicular space and larger rhabdoid cells, are visible in a sample obtained from 1 of 12 tumors that were subjected to target capture and massively parallel DNA sequencing (staining with hematoxylin and eosin).

The present disclosure will be further described with reference to the following non-limiting examples. The teaching of all patents, patent applications and all other publications cited herein are incorporated by reference in their entirety.

cologic pathologist to confirm the diagnosis of SCCOHT, which is characterized by a highly cellular and highly proliferative small cell malignancy with minimal stroma with follicle-like spaces. FIG. 10 shows the typical histopathological features of SCCOHT, including a combination of small neoplastic cells forming a pseudofollicular space and larger rhabdoid cells, are visible in a sample obtained from 1 of 12 tumors that were subjected to target capture and massively parallel DNA sequencing (hematoxylin and eosin). The presence of a large cell or rhabdoid component was accepted as part of the spectrum of this disease. The following entities were excluded from consideration with a combination of morphologic examination and immunohistochemistry (IHC): small cell neuroendocrine carcinoma, juvenile granulosa cell tumor, poorly differentiated Sertoli-Leydig cell tumor, desmoplastic small round cell tumor, metastatic melanoma, lymphoma, and rhabdomyosarcoma. Clinical data collection was limited to only age and year of diagnosis due to HIPAA regulations. No family history was available. Diagnosis of SCCOHT was also facilitated by IHC of common markers including EMA, p53, cytokeratin, LCA, inhibin, CD10, S100, desmin and WT1 (Table 2).

TABLE 2

Summary of Immunohistochemistry Studies Performed to Assist with Diagnostic Interpretation

| Case | EMA | P53 | Cytokeratin | Inhibin | LCA | CD10 | S100 | Desmin | WT1 |
|---|---|---|---|---|---|---|---|---|---|
| 101 | ND | ND | + | ND | ND | ND | ND | − | + |
| 102 | − | + | + | − | − | + | − | − | ND |
| 103 | + | + | + | − | − | + | − | − | ND |
| 104 | ND | ND | + | ND | ND | ND | ND | ND | ND |
| 105 | + | + | ND | − | − |   | − | − | + |
| 106 | + | + | + | − | − | + | − | ND | ND |
| 107 | + | ND | ND | − | ND | ND | − | − | + |
| 108 | + | + | + | − | − | + | − | − | + |
| 109 | − | + | − | − | − | ND | − | − | + |
| 110 | ND | ND | ND | ND | ND | ND | ND | ND | ND |
| 111 | + | + | + | − | ND | ND | ND | − | ND |
| 112 | − | ND | − | − | − | ND | − | − | + |

EXAMPLES

Example 1

Unbiased Screening of 279 Cancer Genes Identities SMARCA4 as a Novel Gene Underlying Small Cell Ovarian Cancer This Example demonstrates that an unbiased screening of 279 cancer genes in 12 ovarian cancer patients identifies the gene coding SMARCA4 protein, a member of several key tumor suppressor complexes, as a novel marker for a variant of ovarian cancer, namely small cell carcinoma of the ovary, hypercalcemic type (SCCOHT). Mutations of SMARCA4 were detected in 100% of patients examined, making SMARCA4 an excellent diagnostic marker for this type of rare and aggressive ovarian cancer affecting young women.

SCCOHT is a rare, aggressive form of ovarian cancer diagnosed in young women that is generally fatal when spread beyond the ovary. Most patients relapse and die within 2 years of diagnosis, regardless of stage, with a long-term survival rate of only 33%, even when disease is confined to the ovary at diagnosis. Seidman et al., *Gynecol Oncol* 59: 283-7 (1995). Thus, a genetic marker is urgently needed for the early diagnosis and treatment of this aggressive disease.

Tissue samples from twelve patients that had been diagnosed with SCCOHT were reviewed by a specialty gyne- DNA and RNA were extracted from paired formalin-fixed, paraffin-embedded (FFPE) tumors from these 12 patients with at least 50% tumor cell nuclei and normal tissue samples according to standard protocols. Germline DNA was derived from either peripheral lymphocytes or FFPE blocks of anatomically distant tissues, such as benign lymph nodes, and used as the source of normal tissue.

To identify key genes underpinning SCCOHT, paired normal and tumor samples were sequenced to a depth of at least 100× using target capture and massively parallel sequencing. The inventors profiled genomic alterations in 279 key cancer-associated genes using IMPACT (Integrated Mutation Profiling of Actionable Cancer Targets), a custom hybrid capture-based deep sequencing assay. Won et al., *J Vis Exp* October 18(80):e50710 (2013). The selected genes encompass all well-established oncogenes and tumor suppressor genes including all druggable targets of FDA-approved therapies and investigational compounds in clinical trials at MSKCC. Custom oligonucleotide probes were designed to capture all protein-coding exons and select introns of these 279 commonly implicated oncogenes, tumor suppressor genes, and members of pathways deemed actionable by targeted therapies.

Barcoded sequence libraries were prepared (New England Biolabs, Kapa Biosystems) and exon capture was performed on barcoded pools by hybridization (Nimblegen SeqCap)

using an input of 97-250 ng DNA, as previously described. Wagle et al., *Cancer Discov* 2:82-93 (2012). Captured pools were sequenced on an Illumina HiSeq 2000 (2×75 bp reads), and reads were aligned to the reference human genome (hg19) using the Burrows-Wheeler Alignment tool. Li and Durbin, *Bioinformatics* 25:1754-60 (2009). Duplicate filtering, local multiple sequence alignment and base quality score recalibration were performed using the Genome Analysis Toolkit (GATK) according to GATK best practices. DePristo et al., *Nat Genet* 41:491-8 (2011). Sequence data were analyzed to identify 3 classes of somatic alterations: single-nucleotide variants using MuTect, (Cibulskis et al., *Nat Biotechnol* 31:213-9 (2013)) small indels using SomaticIndelDetector (DePristo et al., *Nat Genet* 43:491-8 (2011)), and copy number alterations, as previously described. Wagle et al., *Cancer Discov* 2:82-93 (2012). All candidate mutations and indels were manually reviewed using the Integrative Genomics Viewer. Robinson et al., *Nat Biotechnol* 29:24-6 (2011). All mutations were validated using Sanger sequencing in both genomic DNA and RNA transcripts (cDNA) to confirm the somatic nature of the alteration and transcript expression. Primers spanning exon/intron 18, 24 and 28 were constructed for cases 101, 102 and 112, respectively, to determine the presence of retained introns. For cDNA synthesis, the SuperScript III One-Step RT-PCR System (Invitrogen) was used according to the manufacturer's instructions.

Computational and biostatical analyses were performed. Mutation frequencies across The Cancer Genome Atlas (TCGA) tumor types were collated from data contained within the cBioPortal for Cancer Genomics (http://cbioportal.org). Cerami et al., *Cancer Discov* 2:401-4 (2012); Gao et al., *Sci Signal* 6:11 (2013). Background mutation frequencies for the 279 genes sequenced as part of this study were also obtained for TCGA tumor types, excluding hypermutated cases that carry more than 1,000 nonsynonymous mutations.

Results from target capture and massively parallel sequencing revealed that SMARCA4 mutations occurred throughout various exons and included nonsense, frameshift, and splice site mutations as well as a homozygous intragenic deletion of two exons summarized in FIG. 1A. No SMARCA4 missense mutations were identified. Sequence variants from all 12 cases were further validated using Sanger sequencing. cDNA was sequenced in seven samples, and all were found to have mutations expressed within RNA transcripts. Next-generation sequencing data and sequence-specific electropherograms were obtained for all 12 cases (data not shown).

One case contained a germline mutation (case 111, Table 1), which is consistent with prior reports suggesting a hereditary component to this disease. Longy et al., *J Med Genet* 33:333-5 (1996); McDonald et al. *J Pediatr Surg* 47:588-92 (2012).

The probability of finding one gene mutated in all 12 samples when 279 genes are sequenced is given by 1-(1-p12)279. This assumes that mutation of a given gene in a patient is a Bernoulli trial with probability p, the gene mutations are exchangeable, and also independently and identically distributed across patients. We used p=0.015, derived from TCGA samples as explained above. The tumor and normal samples were sequenced to a mean depth of 442× across all genes. A minimum depth of 100× was achieved in 97% of target exons in tumors. The SMARCA4 somatic mutations identified in all tumor samples are shown in Table 1.

Figure 1B:
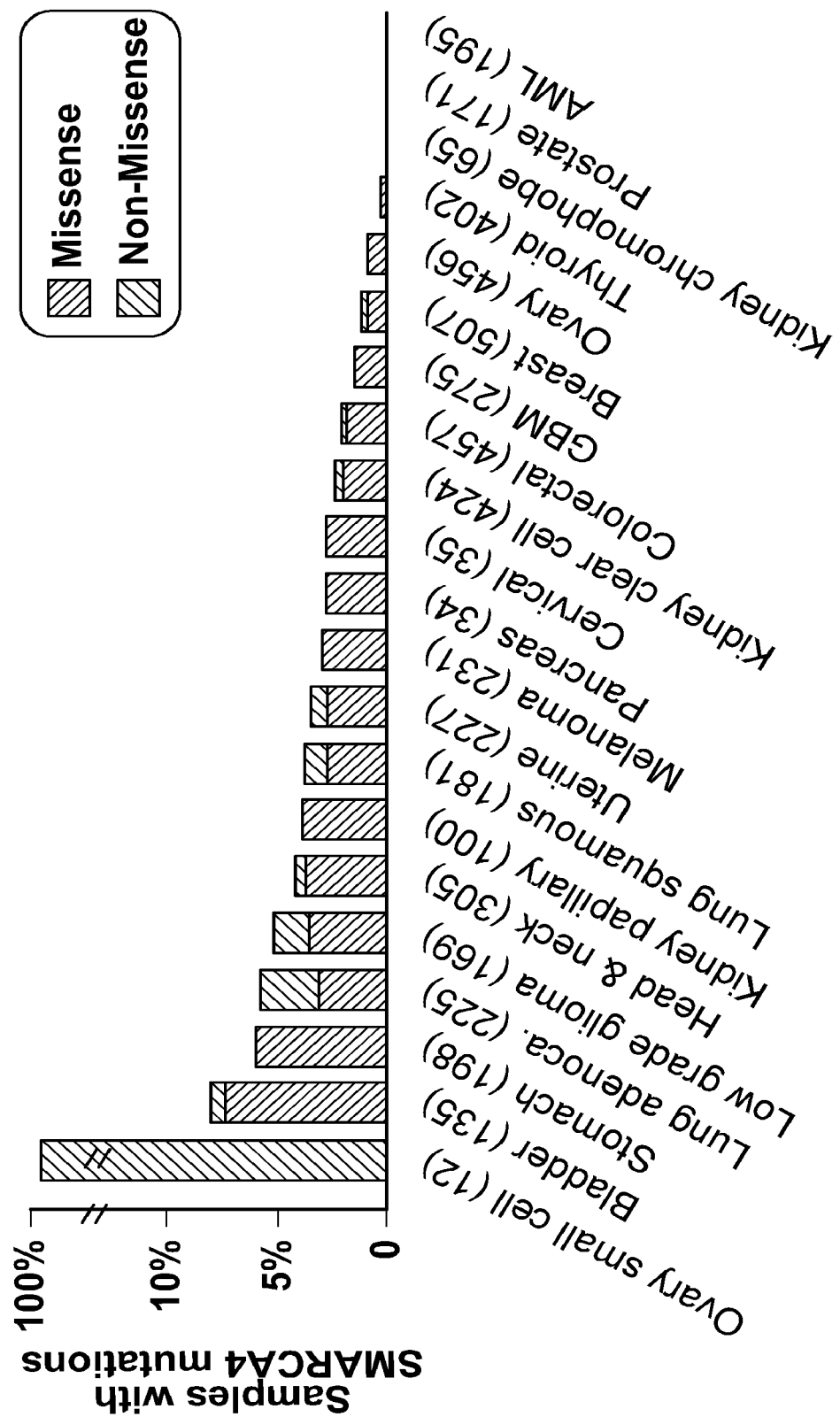
FIG. 1B is a bar graph showing the percentages of samples with non-synonymous SMARCA4 mutations in the SCCOHT and TCGA non-hypermutated samples (numbers of samples per study in parentheses). The darker bars (bar corresponding to case No. 12 and upper portions of two-tone bars) represent samples with missense-only mutations, and the lighter bars (bars corresponding to case Nos 100, 231, 34, 35, 275 and 456 and 402 as well as the lower portion of two-tone bars) represent samples with non-missense (including nonsense, frameshift, splice site, and indel) mutations.

In conclusion, among all 279 cancer-related genes screened among the 12 SCCOHT cases, one gene remarkably stood out: SMARCA4 mutations were identified in each case (FIG. 1B). The probability of identifying SMARCA4 mutations in all 12 samples is less than $2.22 \times 10^{-16}$. Only four additional non-recurrent somatic mutations were identified in any of the other 278 genes sequenced across all 12 samples. In contrast, an analysis of 4,784 non-hypermutated tumors across The Cancer Genome Atlas (TCGA) revealed somatic mutations in an average of 4.3 of these 279 genes (STD 4.4) per tumor. TCGA samples with inactivating SMARCA4 mutations had more mutations in the other 278 genes sequenced (mean=14) in contrast to the SCCOHT cases. Thus, SMARCA4 is a novel marker for ovarian cancer, especially SCCOHT.

Example 2

Mutations that Reduce SMARCA4 Gene Expression and/or SMARCA4 Protein Expression are Associated with SCCOHT This Example demonstrates that the SMARCA4 mutations identified among 12 SCCOHT patients in Example 1 are all loss-of-function mutations, thus suggesting SMARCA4 may be causatively linked to ovarian cancer, especially SCCOHT.

Examination of the SMARCA4 mutations demonstrated that they occurred throughout various exons and included nonsense, frameshift, and splice site mutations as well as a homozygous intragenic deletion of two exons. FIG. 1A summarizes the mutations among all 12 SCCOHT patients. Interestingly, no SMARCA4 missense mutations were identified in these 12 patients.

To confirm the results obtained from IMPACT, sequence variants from all 12 cases were validated using Sanger sequencing. cDNA was sequenced in 7 samples, and all were found to have mutations expressed within RNA transcripts. Next-generation sequencing data and sequence-specific Sanger electropherogram validation results were obtained for all 12 cases. 4 cases harbored two inactivating mutations each in SMARCA4 (cases 104, 105, 106, 109). The remaining eight cases harbored single inactivating mutations accompanied by loss of heterozygosity at the SMARCA4 locus (supported by adjacent single nucleotide polymorphisms [SNPs]); in each case, the mutant allele frequency was 0.75 or greater.

Figure 6A:
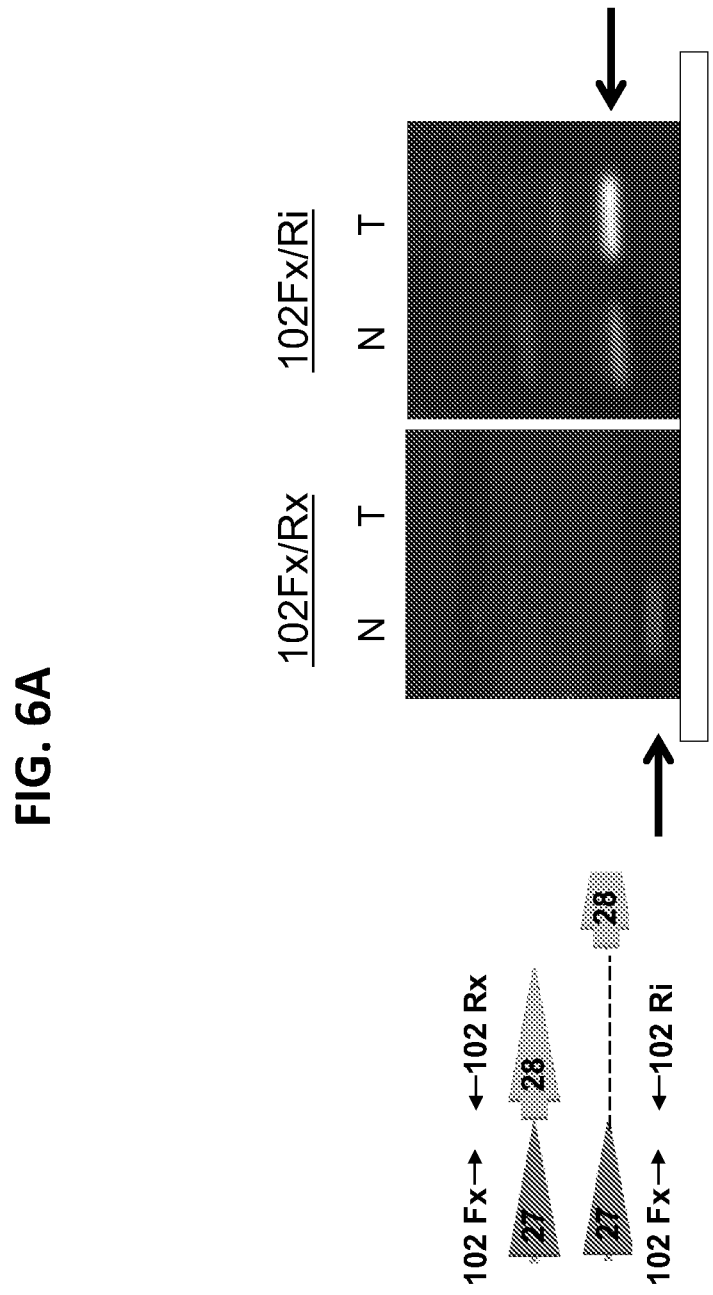
FIG. 6A is a digital image of a DNA gel and a diagram showing analysis of splice site variant in tumor tissue from case 102. One-step RT-PCR confirms that the exon/intron band is preferentially expressed over the exon/exon band in tumor tissue. The exon-exon primers detected weaker bands, reflecting loss of expression in tumor tissues compared with normal tissues in cases with splice site mutations. Immunoblots showing much reduced SMARCA4 protein levels are shown in FIG. 2B. The exon-intron primers demonstrated equivalent to greater expression of retained intron in the tumor tissues. Since SMARCA4 introns may be retained in non-cancer tissues, some intronic expression is expected in normal tissues. These data taken together indicate preferential intronic expression, as expected, in cDNA sequenced from tumor samples with splice site mutations.
Figure 6B:
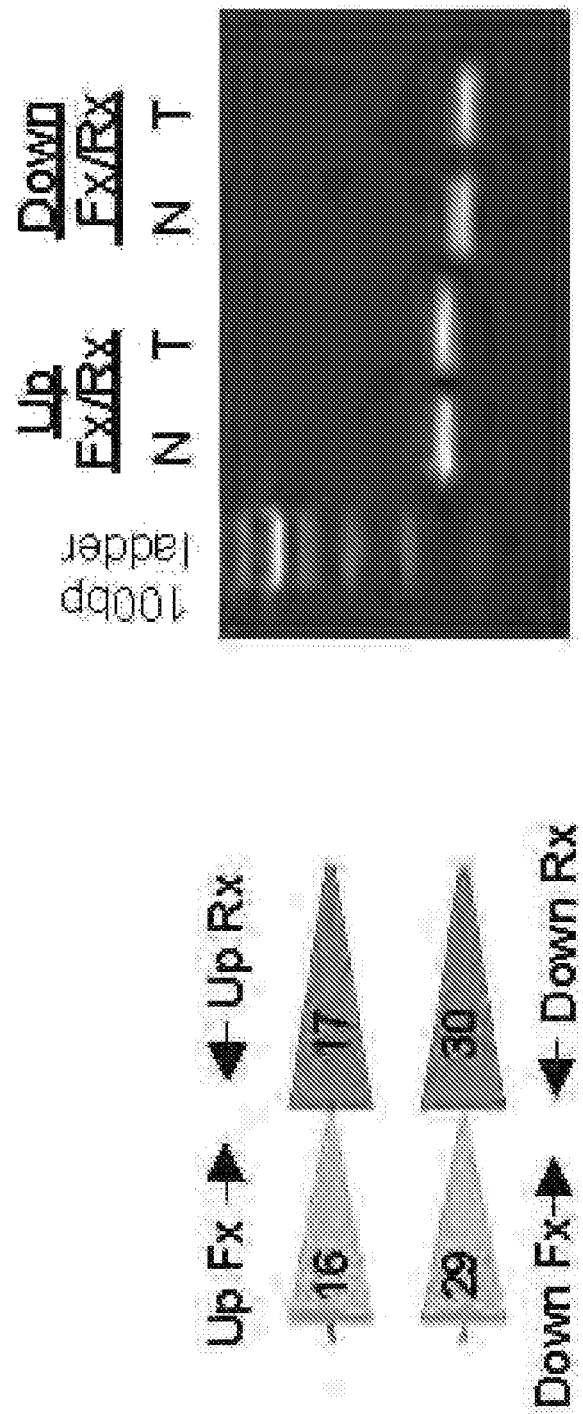
FIG. 6B is a digital image of a DNA gel and a diagram showing that one-step RT-PCR with primers targeting regions upstream and downstream from the mutation site in tumor tissue from case 102 show equal expression demonstrating continuation of transcription downstream from the mutation.

Due to the precise location of biallelic splice site mutations within intronic sequence at the highly conserved AG donor region, we tested whether introns in cases 101, 102, and 112 were retained. We identified preferential intronic expression, as expected, in cDNA sequenced from a representative tumor sample with a splice site mutation (case 102, FIG. 6A). One step RT-PCR confirmed continuation of transcription downstream from the splice site mutations, suggesting that the splice site mutations do not cause mRNA truncation (case 102, FIG. 6B).

Figure 5A:
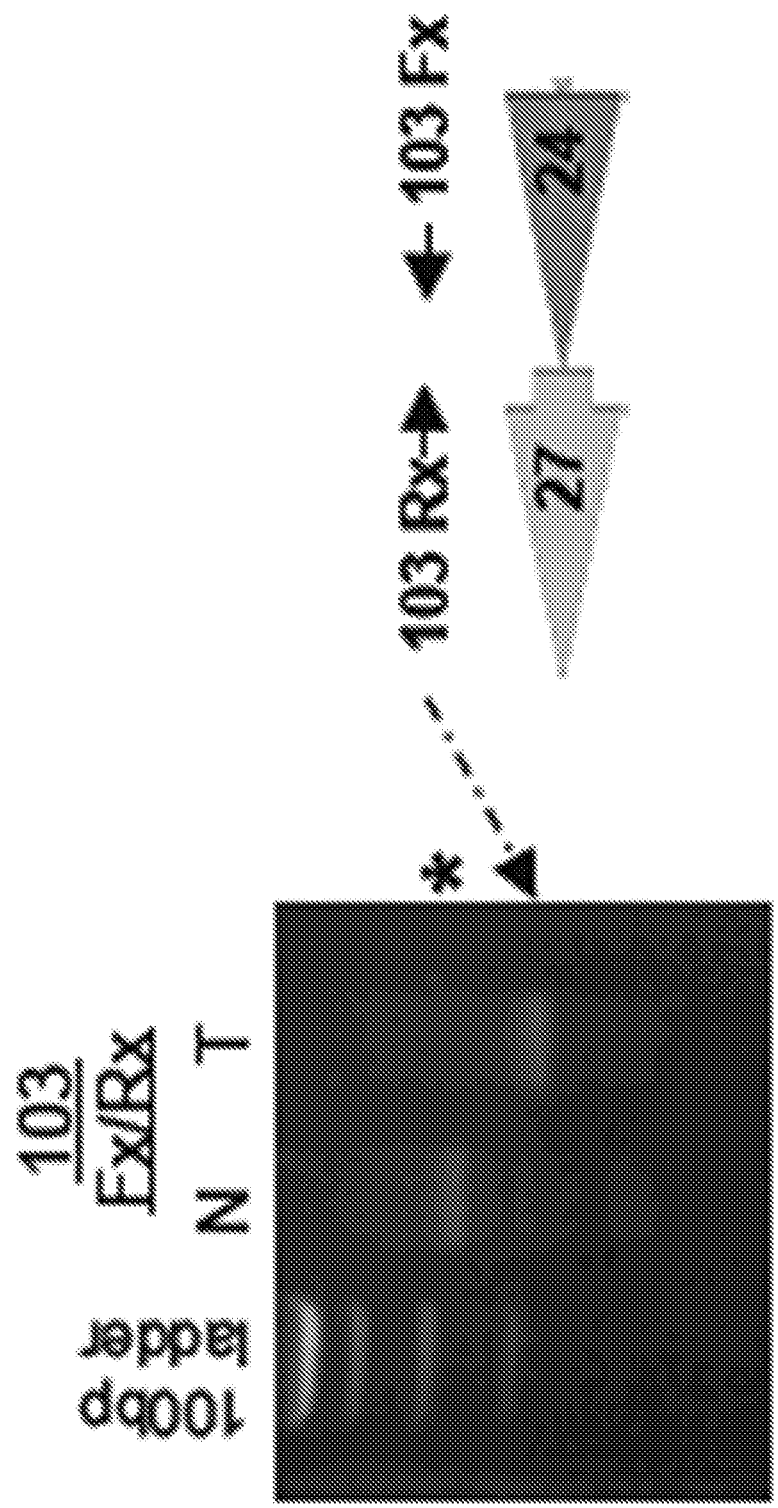
FIG. 5A is a digital image of a DNA gel and a diagram showing that one-step RT-PCR confirms that tumor tissue from case 103, which exhibits a deletion of exons 25 and 26, yields a single band with primers that span exons 24 and 27 (*denotes a nonspecific band).
Figure 5B:
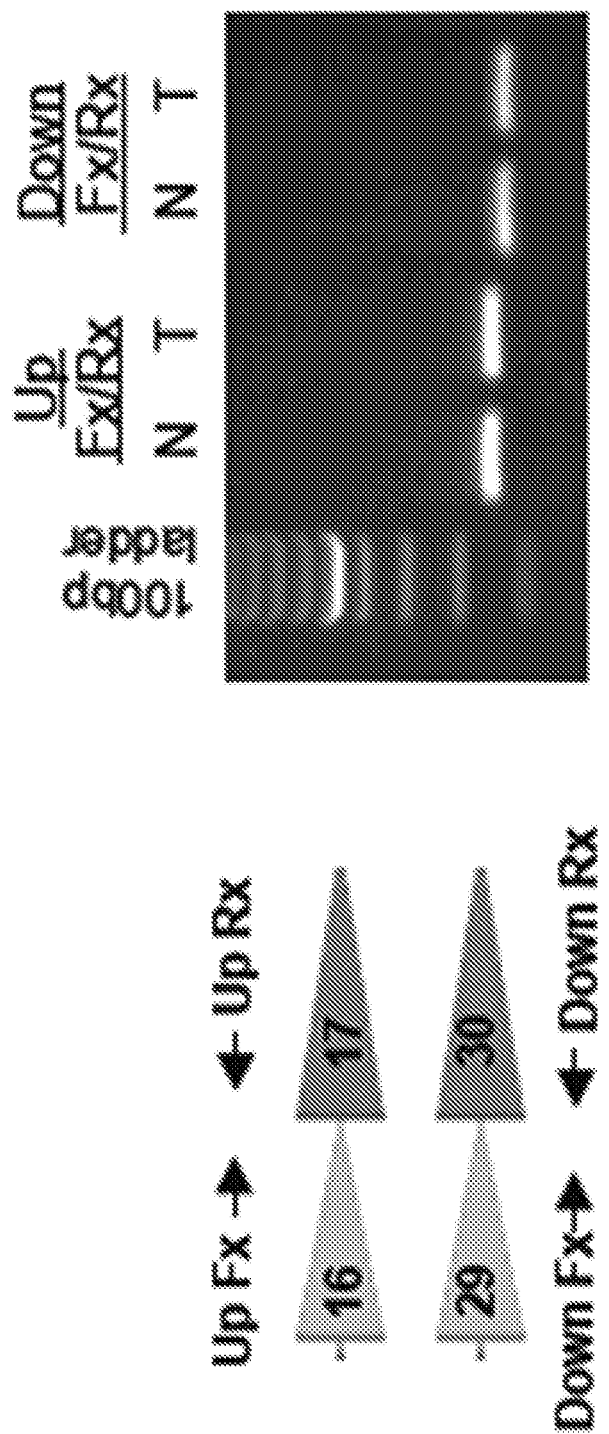
FIG. 5B is a digital image of a DNA gel and a diagram illustrating that one-step RT-PCR with primers targeting regions upstream and downstream from the deletion site in tumor tissue from case 103 show equal expression demonstrating continuation of transcription downstream from the deletion.

A homozygous in-frame deletion of 102 amino acids from exons 25 and 26 detected in case 103 was confirmed by Sanger sequencing of cDNA, which resulted in partial deletion of the helicase domain. One-step RT-PCR confirms that tumor tissue yields a single band with primers that span exons 24 and 27 (FIG. 5A). Upstream and downstream primer pairs confirmed that transcription continued downstream of this deletion (FIG. 5B). IHC showed the retention of protein expression. However, sequencing data confirming an impaired C-terminal helicase domain suggests that this deletion results in translation of a truncated non-functional catalytically dead product. A homozygous in-frame four amino acid (ETVN (SEQ ID NO: 10)) deletion within exon 27 was detected in case 107. No additional tissue was available to demonstrate the effect on protein expression.

In addition to the 12 SCCOHT patients, the inventors also examined the association of SMARCA4 mutations and its expression in other types of cancers. FIG. 3 shows grouped data demonstrating SMARCA4 gene expression across TCGA tumors for cases with available mutation and RNA sequence data (RSEM). A correlation is seen between inactivating SMARCA4 mutations and decreased gene expression across various solid tumors.

In summary, among all 12 patients (Table 1), inactivating biallelic mutations of SMARCA4 gene are found in each case. Inactivating mutations include insertions and deletions, frame shift, splice site and nonsense mutations. The SCCOHT tumors had few other mutations in the panel of 278 sequenced genes. Though the study is limited by a modest samples size due to the rarity of this disease, the identification of inactivating mutations in a single gene in all 12 tumors studied is consistent with the characteristics of a tumor suppressor. Most of the identified mutations reside within the known helicase catalytic domains of SMARCA4, suggesting a potential role in tumorigenesis.

Example 3

SCCOHT Patients Exhibit Dysfunctional or Deficient SMARCA4 Protein

This Example demonstrates that the inactivating mutations of SMARCA4 identified among 12 SCCOHT patients in Example 2 also result in the loss of protein expression and function. This observation strongly suggests SMARCA4 is not merely a marker of the disease, but it may be causatively linked to SCCOHT.

SMARCA4 (BRG1) immunohistochemistry (IHC) was performed in the nine cases with available tissue samples. The IHC staining method for SMARCA4 was optimized using several antibodies in a variety of different conditions until one was chosen on the basis of its ability to demonstrate consistent nuclear staining patterns in a small group of high-grade serous ovarian cancers serving as positive controls. One whole FFPE section from each of the available SCCOHT cases was evaluated with a commercially available polyclonal antibody against SMARCA4 (Upstate cell signaling solutions, Cat #07-478). Whole sections underwent epitope retrieval using heat by steaming with EDTA at pH 8 for 30 minutes. This was followed by overnight incubation with the primary antibody at 4° C. (dilution 1:4000). Detection of bound antibody was accomplished with biotinylated anti-rabbit IgG (dilution 1:500, Vector Laboratories, Cat # BA-1000) and ABC (Vector Laboratories, Cat # PK-6100). DAB was used as the chromogen. For tumors with mutant SMARCA4 and loss of SMARCA4 protein expression, positive staining of blood vessels and stromal cells was used as an internal positive control. The absence of nuclear staining in tumor cells in the presence of an internal positive control was scored as "loss of expression."

Figure 4:
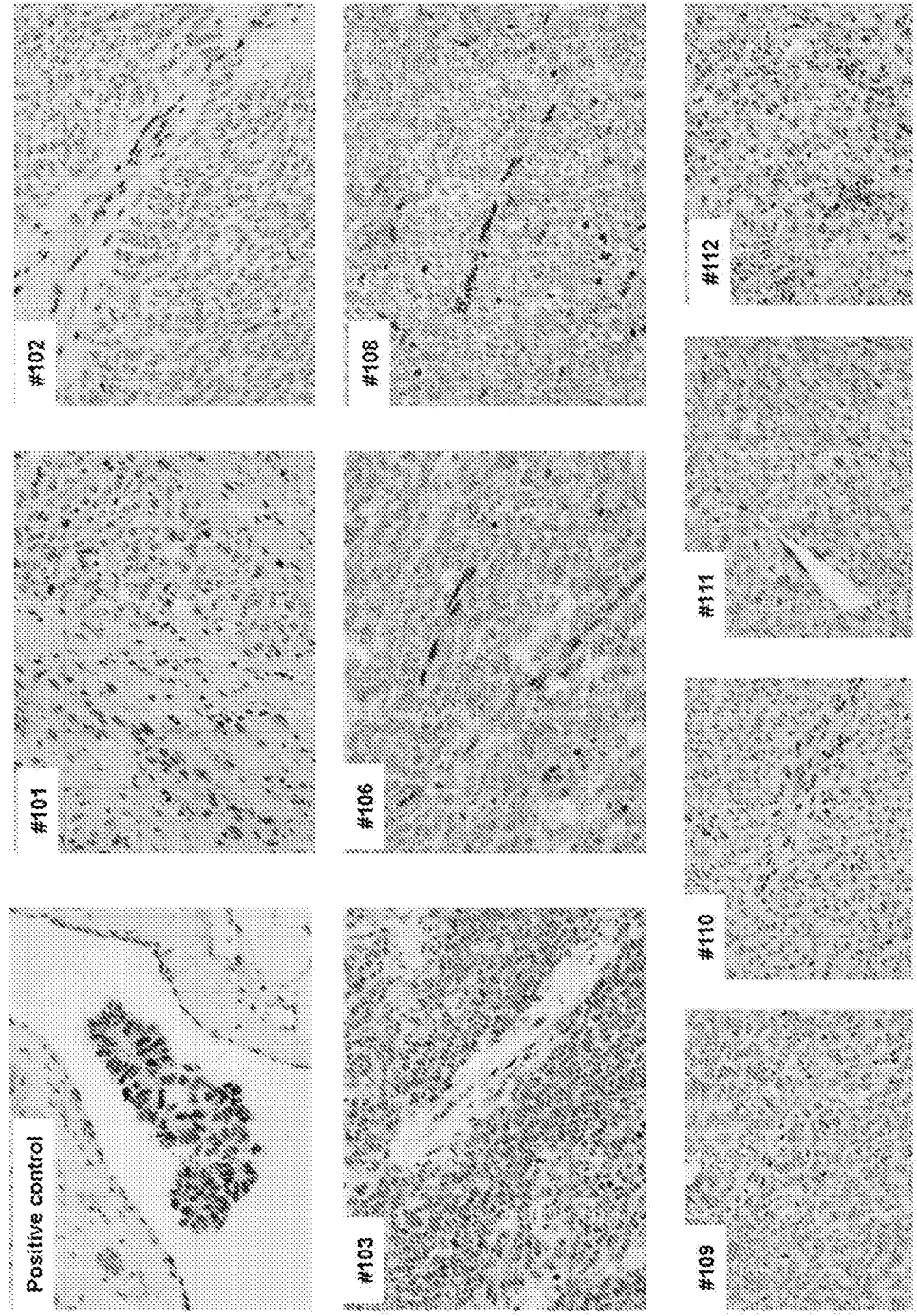
FIG. 4 is an immunohistochemistry (IHC) image showing results of SMARCA4 staining in SCCOHT cases. High-grade serous ovarian carcinoma is used as a positive control. Case numbers are indicated in each panel. Note the intense staining of blood vessels and stromal cell nuclei as internal controls.

High-grade serous ovarian cancer with wild-type SMARCA4 sequence served as a positive control. In cases 104, 105, 106, 108, 109 and 110, nonsense mutations resulted in a premature stop codon within the open reading frame of the mRNA transcript. In cases 104, 105, 106 and 109, the nonsense mutation was heterozygous with a concurrent frameshift or splice site mutation. IHC demonstrated loss of SMARCA4 nuclear staining and retention of staining in the internal positive control cells in all four cases with nonsense mutations that had available tissue (FIG. 4). Compared to the strong SMARCA4 staining in the positive control sample (top left panel, FIG. 4), all the cases with tumor tissue samples processed by IHC showed significantly less staining intensity. Case 111 was found to have a heterozygous germline nonsense mutation with loss of the wild-type somatic allele and associated loss of IHC protein expression. This case had a paucity of pseudofollicular spaces that were more common in the remainder of the study cohort.

Immunoblotting was also used to validate the results from IHC in representative patients. Frozen tumor samples were available from 2 cases (101 and 102). Prior to protein extraction, cells were washed with ice-cold PBS. Cells were lysed in RIPA buffer. Extracted proteins were resolved by SDS-PAGE electrophoresis, transferred on nitrocellulose, and blotted with polyclonal anti-Brg-1 (dilution 1:1000; Santa Cruz Biotechnology, Cat # sc-10768) and anti-α-tubulin (Santa Cruz Biotechnology, Cat # sc-5546) as a loading control.

Figure 2A:
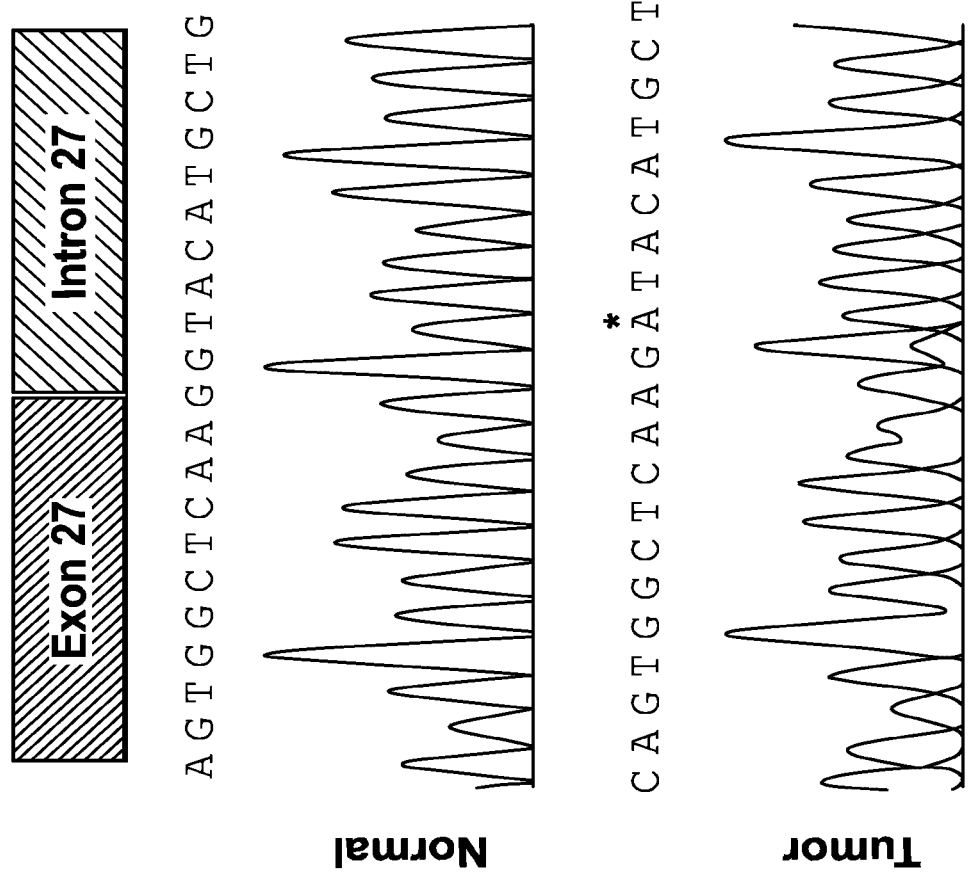
FIG. 2A is a Sanger sequence trace chromatogram showing analysis of an exemplary SMARCA4 mutation, which, in this case (No. 102) was a single nucleotide (G>A) somatic mutation within the intron 27 donor splice site region. Similar analyses were performed for each of the case Nos 101 and 103-112 (data not shown). Figure discloses SEQ ID NOs: 11 and 12, respectively, in order of appearance.
Figure 2B:
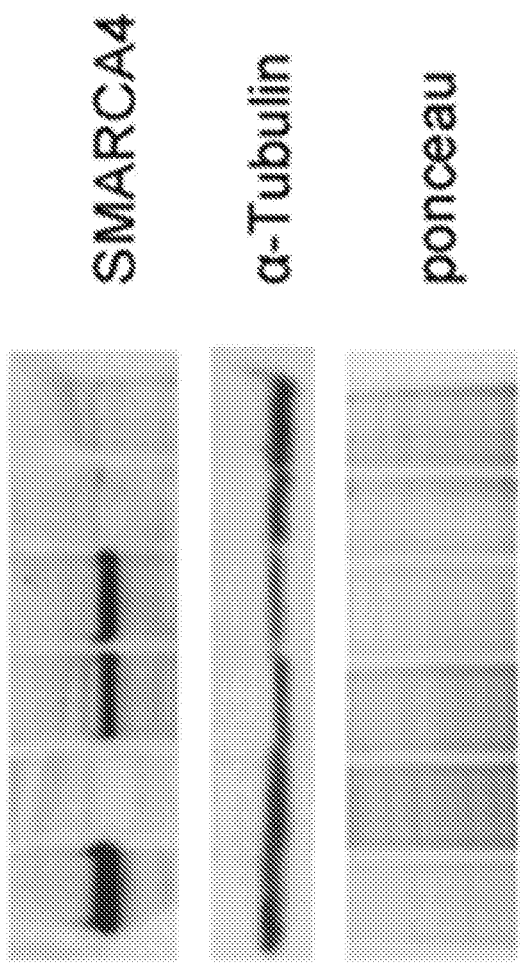
FIG. 2B is an immunoblot with an anti-SMARCA4 N-terminal antibody. A high-grade serous ovarian cancer cell line (PEO4) and frozen tumor samples from 2 patients with high-grade serous ovarian cancer (HGOC #1 and HGOC #2) were used as positive controls and show retained protein expression. Protein extracted from H1299 non-small cell lung cancer cells, deficient in SMARCA4, served as a negative control. Protein extracted from cases 101 and 102 (SCCO #101 and SCCO #102), each with a donor site splice site mutation, exhibit loss of SMARCA4 protein expression.
Figure 2C:
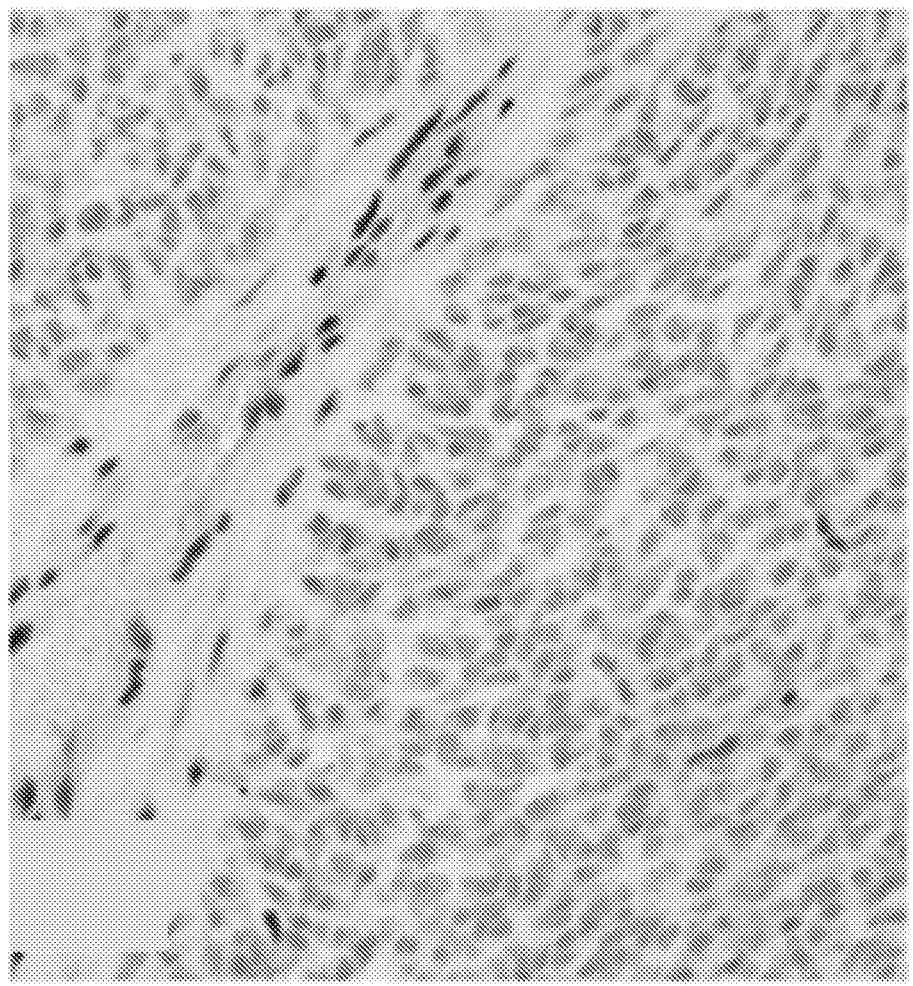
FIG. 2C is an immunohistochemistry (IHC) image showing loss of protein expression from archival SCCOHT tissue stained with a polyclonal SMARCA4 antibody. The intense staining of blood vessels and stromal cell nuclei serve as internal controls.

Both immunoblots and IHC showed clear loss of SMARCA4 protein in cases 101 and 102 (FIG. 2B and FIG. 4). Case 112 had equivocal loss of IHC protein expression with tumor cells staining less intensely than normal tissue elements. A homozygous in-frame deletion of 102 amino acids from exons 25 and 26 detected in case 103 was confirmed by Sanger sequencing of cDNA, which resulted in partial deletion of the helicase domain. Upstream and downstream primer pairs confirmed that transcription continued downstream of this deletion. IHC showed the retention of protein expression. However, sequencing data confirming an impaired C-terminal helicase domain suggests that this deletion results in translation of a truncated non-functional catalytically dead product. A homozygous in-frame four amino acid (ETVN (SEQ ID NO: 10)) deletion within exon 27 was detected in case 107. No additional tissue was available to demonstrate the effect on protein expression.

In conclusion, protein studies of tumor tissue samples from SCCOHT patients demonstrate the loss of protein expression and immunoreactivity of SMARCA4. These results are consistent with the nucleotide analysis of SMARCA4 gene shown in Example 2. Thus, SCCOHT patients exhibit mutations of SMARCA4 genes that result in dysfunctional or deficient SMARCA4 protein, suggesting important oncogenic and therefore targetable functions.

Example 4

SMARCA4 Regulates Cell Proliferation, Demonstrating SMARCA4 as a Therapeutic Target This Example demonstrates that SMARCA4 is not only a marker for SCCOHT, but its absence or dysfunction is likely to contribute to the development of SCCOHT. Functional gain-of-function and loss-of-function studies demonstrate that SMARCA4 is essential for regulating cell proliferation.

To determine the functional effects of SMARCA4 loss, SMARCA4 was ectopically re-introduced through electroporation in SMARCA4-null H1299 human non-small cell lung adenocarcinoma cells (available as CRL-5803™ from ATCC®, Manassas, Va.). SMARCA4 is not a marker for this cancer but this cell line is SMARCA4 null. The H1299 cell line was authenticated in June 2013 by STR DNA profiling method (Genetica DNA Laboratories) using DSMZ database. H1299 cells were cultured in RPMI media supplemented with 10% FCS. 293T cells were obtained from ATCC in September 2011. The cells were cultured in DME-HG media supplemented with 10% FCS. All cells were tested negative for the mycoplasma. Plasmid containing SMARCA4 cDNA (pCMV6-XL5; Origene Cat # SC323288) was transfected in H1299 cells by electroporation using Nucleofector (Amaxa). 24 h post-electroporation cells were counted using TC10 Automated Cell Counter (BioRad), proteins were extracted and analyzed by immunoblotting.

Figure 7:
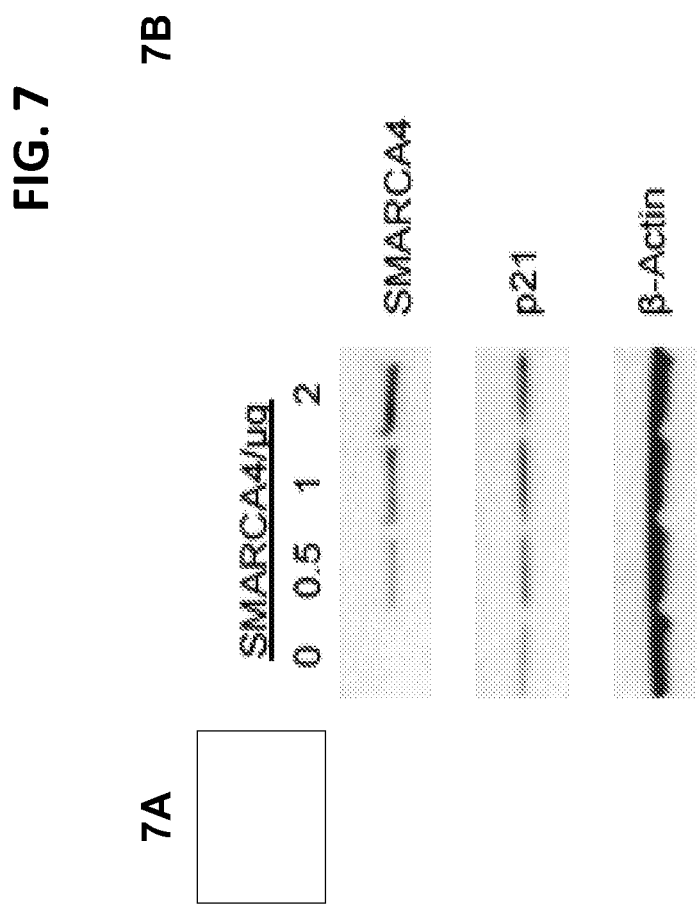
FIG. 7A is a digital image of immunoblots showing SMARCA4 over-expression in H1299 cells. Representative immunoblots from three biologic replicates demonstrate a correlation between increased SMARCA4 and p21 expression.
FIG. 7B is a bar graph showing cell growth assessment in H1299 cells over-expressing SMARCA4. Mean cell number counts from three biologic replicates are shown.
FIG. 7C is a digital image showing representative immunoblot confirming SMARCA4 knock-down in 293T cells using shRNA. As a control, shNTC (Non-Targeting Control) was used.
FIG. 7D is a line graph showing results from XTT proliferation assay in 293T cells depleted of SMARCA4. Means represent three independent experiments.

H1299 cells lack SMARCA4 expression as validated by western blot (FIG. 2B). After the introduction of SMARCA4 cDNA, SMARCA4 protein was detected in H1299 in a dose-dependent manner (FIG. 7A). Re-expression of SMARCA4 resulted in a dose-dependent suppression of cell growth (FIG. 7B). The expression of p21 also increased consistent with prior reports of SMARCA4's effect on cell cycle arrest (FIG. 7A). Hendricks et al., *Mol Cell Biol* 24:362-76 (2004); Napolitano et al., *J Cell Sci* 120:2904-11 (2007).

In addition to gain-of-functions in SMARCA4-deficient cells, we also performed loss-of-function studies in cells normally expressing SMARCA4.

To knock-down SMARCA4 GIPZ SMARCA4 shRNA Viral Particle Starter Kit was used (Thermo Scientific). Transduction was performed according to manufacturer's suggestions. A stable knock-down was obtained by selection with 2 µg/mL puromycin. XTT proliferation assay (ATCC; Cat #30-1011K) was performed according to manufacturer's suggestions. 40,000 cells were seeded in 24-well dish and absorbance was measured at different time points after the seeding (24-96 h) using Synergy™ HT Plate Reader (BioTek) and used to report relative cell proliferation.

The shRNA against SMARCA4 was able to significant knock down its expression, as validated by western blot (FIG. 7C), which led to an increase in cell proliferation as measured by an XTT proliferation assay (FIG. 7D).

Results from these functional experiments with cultured cells demonstrating the crucial role of SMARCA4 in cell proliferation are consistent with the putative functions of SMARCA4. SMARCA4 and other members of the SMARCA4, especially SMARCA2, are key components of protein-protein complexes with tumor suppressing abilities. The highly homologous SMARCA4 (BRG1) and SMARCA2 (BRM) proteins are mutually exclusive ATP-dependent catalytic subunits within the BAF complex and co-exist with ARID1A (BAF250A) or ARID1B (BAF250B). Reisman et al., *Oncogene* 28:1653-68 (2009); Wilson and Roberts, *Nat Rev Cancer* 11:481-92 (2011). SMARCA4 in the PBAF complex is associated with the PBRM1 (BAF180) subunit, which is absent from the BAF complex. Recent studies have demonstrated that the silencing of SMARCA2 through RNA interference suppresses growth of SMARCA4-deficient lung cancer cell lines and xenografts, suggesting a synthetic lethal relationship. Oike et al., *Cancer Res* 23:5508-18 (2013). ARID1A loss has recently been shown to be tumorigenic in an ovarian cancer lineage, suggesting that SMARCA4 loss may be sufficient for transformation through BAF complex p53-dependent mechanisms. Guan et al., *Cancer Res* 71:6718-27 (2011). SMARCA2-ATPase inhibitors may be an effective approach for treating SMARCA4-deficient tumors. Improved understanding of the SWI/SNF complex function and characteristics are now opening therapeutic opportunities for affected tumors. Since SMARCA2 and SMARCA4 are mutually exclusive subunits, we examined the co-occurrence of SMARCA2 and SMARCA4 inactivating mutations among all non-hypermutated TCGA tumors. We found only one case with an inactivating SMARCA4 mutation and a SMARCA2 missense mutation.

In conclusion, both gain-of-function and loss-of-function experiments demonstrate that SMARCA4 plays a critical role in regulating cell proliferation. While a decrease in SMARCA4 expression promotes cell proliferation, an increase in its expression suppresses cell proliferation. These results are consistent with the clinical data that loss-of-function SMARCA4 mutations identified from 12 SCCOHT patients are associated with tumor growth. Taken together, the association between SMARCA4 and SCCOHT is likely a causal one; that is, loss of function in SMARCA4 by inactivating mutations may be one cause of tumorigenesis in SCCOHT patients, and likely also plays a role in tumor growth and disease progression. Thus, SMARCA4 emerges as a novel target for intervention for the prevention and treatment of ovarian cancer, especially SCCOHT. In addition, the knowledge gained from gain-of-function studies with SMARCA4 expression vector can also be used to for developing gene and cell therapies that promote SMARCA4 expression.

Example 5

Use of SMARCA4 to Regulate Tumor Growth

This Example describes experiments that have indicated or will demonstrate SMARCA4 may also be used as a therapeutic or therapeutic target for other types of cancer.

SMARCA4 mutations have been previously reported at low frequency in other solid tumors. Across all tumors characterized by TCGA to date, SMARCA4 mutations have been detected in 3% of 4,787 non-hypermutated samples (FIG. 1B and FIG. 10). Mutation frequencies of 5-8% are present in bladder carcinoma, stomach adenocarcinoma, lung adenocarcinoma, and lower grade glioma. Of the 128 somatic SMARCA4 mutations in the TCGA samples, 84% were missense variants of uncertain functional significance (FIG. 1B).

For all TCGA samples, the mean RSEM (2050, std: 1760) was less in samples with non-missense mutations than other samples without mutations or with only missense mutations (3724, std: 1692; $P=8.7\times10^{-4}$) (FIG. 3). For TCGA lung adenocarcinoma samples, the mean RSEM (601, std: 370) was less in samples with non-missense mutations than other samples without mutations or with only missense mutations (3330, std: 1524; $P=2\times10^{-8}$) (FIG. 3).

Figure 8:
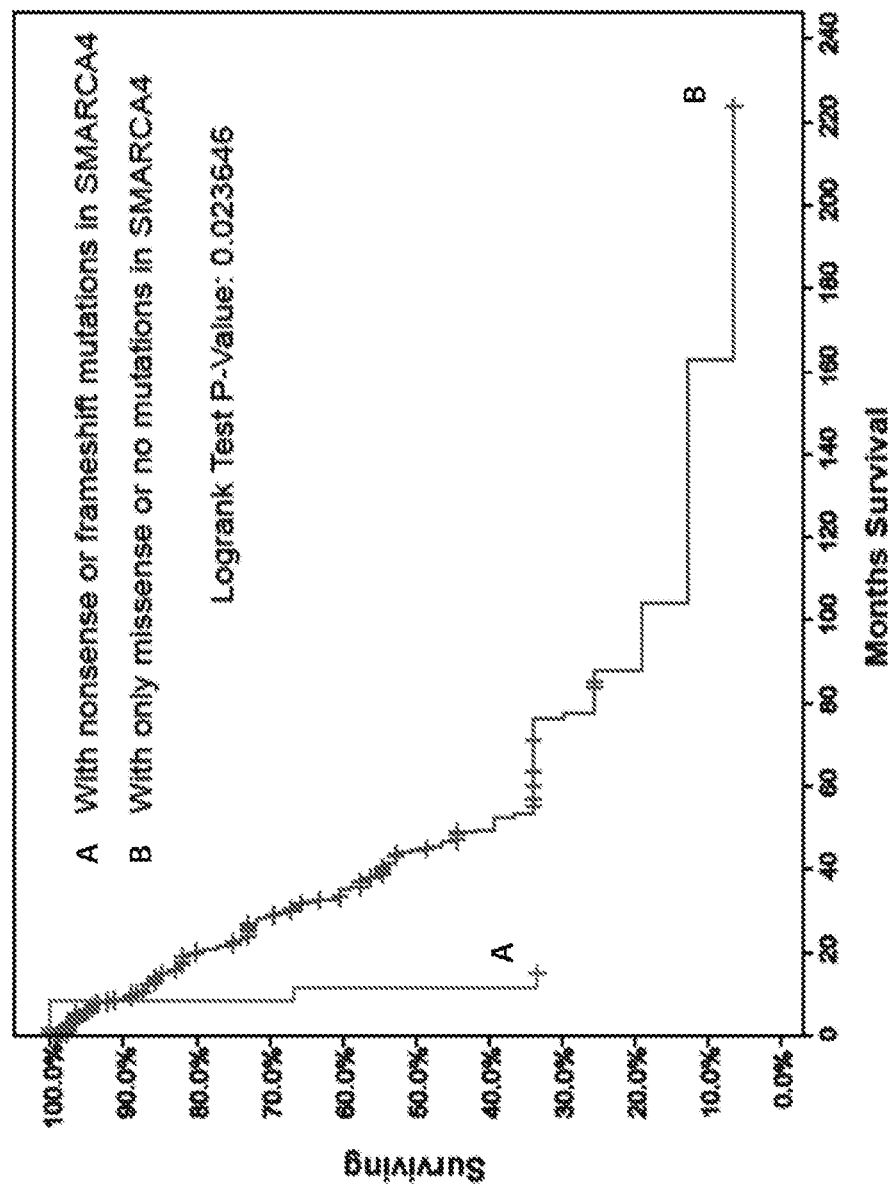
FIG. 8 is a Kaplan-Meier survival plot showing overall survival among lung adenocarcinoma TCGA cases based on SMARCA4 mutations. Median overall survival was 11.6 months among 6 patients with inactivating SMARCA4 mutations compared with 44.6 months for 197 patients without inactivating mutations.
Figure 9:
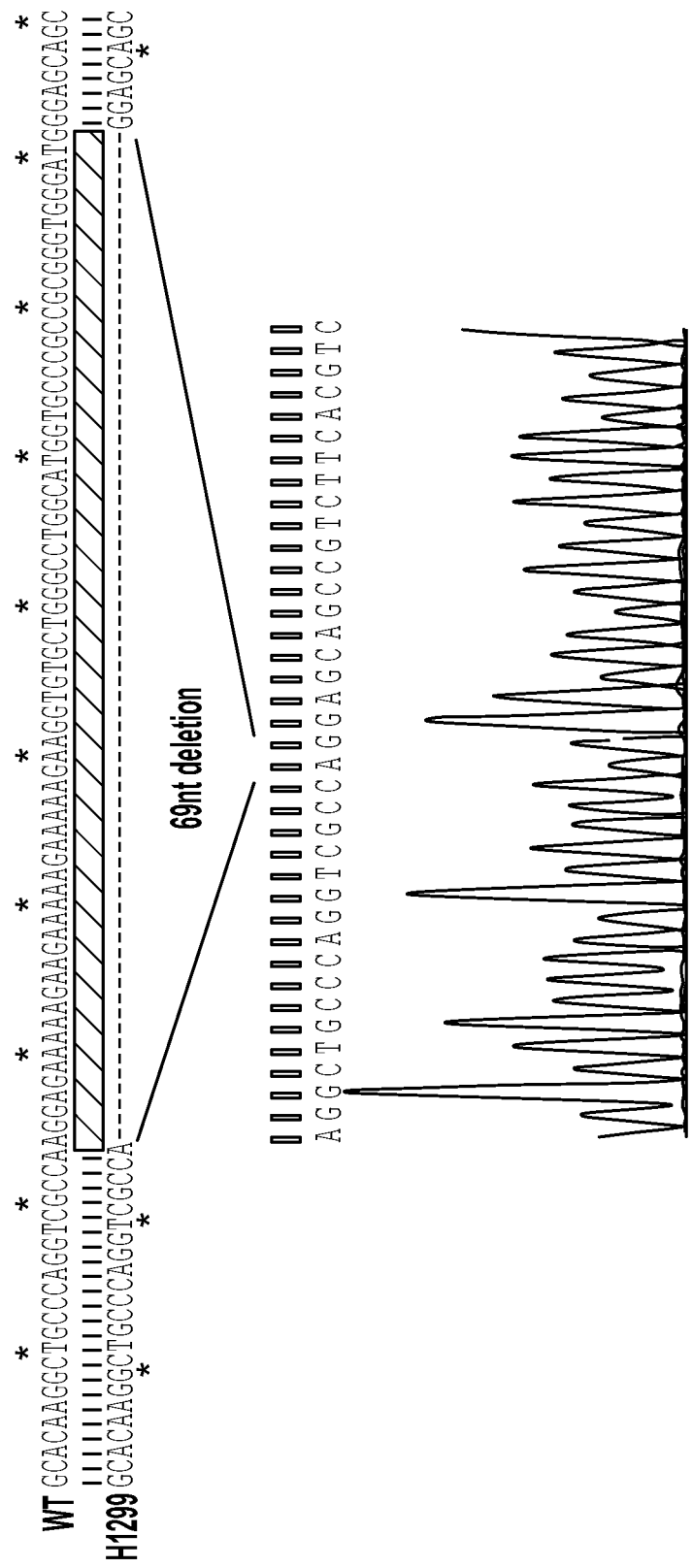
FIG. 9 is a sequence map and a Sanger chromatograph showing sequence analyses for SMARCA4 in H1299 cell line. An electropherogram from Sanger sequencing of genomic DNA validating a 69 nucleotide deletion in the open reading frame of this control cell line that results in loss of protein expression, as shown in FIG. 2B. Figure discloses SEQ ID NOs: 13-15, respectively, in order of appearance.

Examination of SMARCA4 in various cancers identifies that in addition to ovarian cancer, especially SCCOHT, inactivating SMARCA4 mutation is also frequently found in lung adenocarcinoma, and lower grade glioma among other cancers. The association between inactivating mutations in SMARCA4 and lung adenocarcinoma was analyzed and it was discovered that patients with inactivating SMARCA4 mutations exhibited poor outcome (FIG. 8). Their survival rate was significantly lower compared to patients without inactivating SMARCA4 mutations (p=0.02). This suggests that the role of SMARCA4 in controlling proliferation has therapeutic implications beyond SCCOHT (where SMARCA4 is a diagnostic marker) to other cancer populations (even cancers where loss of SMARCA4 has an incidence too low to serve diagnostically). A therapeutic intervention restorative of SMARCA4 expression and function for the SMARCA4 deficient patient subpopulation may be useful to control tumor growth and therefore reduce tumor burden. Indeed, overexpression of SMARCA4 both in SMARCA4 deficient and SMARCA4 competent tumors may control tumor growth.

In conclusion, the evidence linking SMARCA4 to ovarian cancer, especially SCCOHT, is strong. But the epidemiological evidence presented here, coupled with the observation that SMARCA4 regulates cell proliferation, suggests that SMARCA4 may be a candidate for a therapeutic target for other types of cancers, such as lung adenocarcinoma, and lower grade glioma.

Example 6

Recurrent SMARCA4 Mutations in Small Cell Carcinoma of the Ovary

Figure 11:
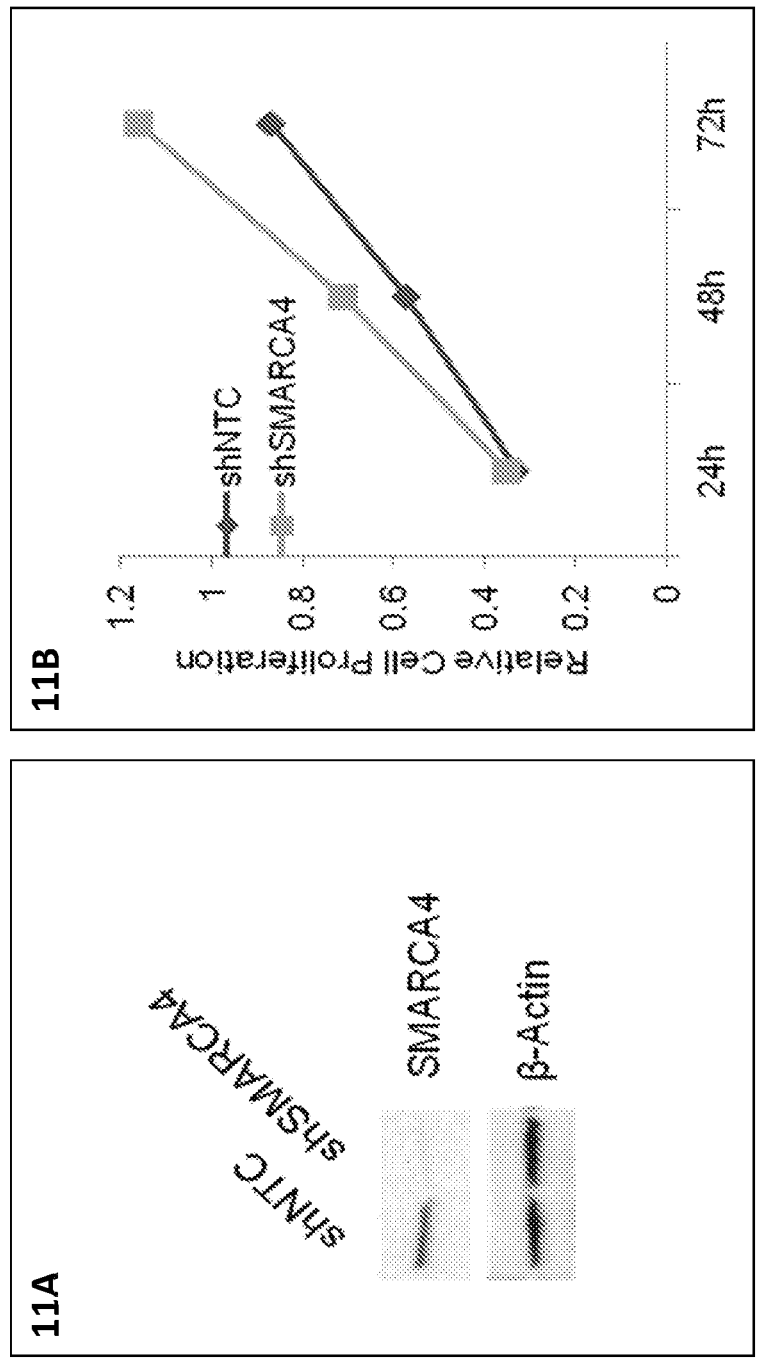
FIG. 11A is a western blot confirming SMARCA4 knock-down (β-Actin is a loading control and shNTC is a non-targeting control).
FIG. 11B is a graph of relative cell proliferation as a function of time. These data demonstrate that depletion of SMARCA4 in T80 cells increases cell growth.

It has been suggested that SMARCA4 acts as a tumor suppressor. To confirm SMARCA4's tumor suppressor role in small cell carcinoma of the ovary hypercalcemic type (SCCOHT), SMARCA4 gene has been knocked down and is planned to be knocked down in target cell lines and measure tumorigenic effects. Although it remains speculative, it has been suggested that SCCOHT originates from ovarian epithelial cells. Therefore, as model cell lines we will use a panel of normal ovarian epithelial cell lines such as T80, HOSE 6-7, OSE. To knock-down SMARCA4, we will use the same approach as in our preliminary studies where we successfully depleted SMARCA4 in T80 cells and demonstrated an increase in cell growth reflective of SMARCA4's tumor suppressor activity (FIGS. 11A and 11B).

GIPZ SMARCA4 Viral Starter Kit (Thermo Scientific) provides purified shRNA viral particles with appropriate negative and positive controls. Target cell lines can be transduced with these particles according to manufacturer's suggestions. Briefly, at day 0, cells can be seeded to approximate 80% confluence and the following day the viruses can be applied. To achieve stable knock-down and select for successfully transduced cells, the cells can be treated with puromycin. Knock-down can be tested on both RNA and protein levels utilizing Real-Time PCR Taqman (Applied Biosystems) and Western blotting assays, respectively.

Once knock-down is confirmed, assays that are traditionally used to measure malignant transformation, such as cell proliferation (XTT assay from ATCC), cell migration and invasion assays (BD Biosciences) can be performed. The Soft Agar Assay can be used for Colony Formation (Cell Biolabs), which is considered the most stringent assay for measuring malignant transformation of cells. All assays can be performed according to manufactures' suggestions.

As shown in preliminary studies in T80 cells, cell growth increases upon SMARCA4 depletion. Given that it has been demonstrated that BIN-67 cells, a SCCOHT cell line, is capable of forming spheroids (Gamwell L F et al. *Orphanet Journal of Rare Diseases*; 2013 Feb. 21; 8:33) colony formation in a Soft Agar Assay can be used to demonstrate that SMARCA4 knock-down results in increased cell growth.

The BIN-67 cell line can also be used to complement knock-down studies, by showing the reduction in cell growth upon SMARCA4 re-introduction into those cells. The lack of SMARCA4 expression can first be confirmed in those cells and SMARCA4 can be overexpressed with a plasmid containing SMARCA4 cDNA (pCMV6-XL5; OriGene). Over-expression can be confirmed by western blot. In this way, it can be demonstrated that SMARCA4 overexpression reduces cell growth and, thereby, reverses the malignant phenotype.

Example 7

A Xenograft Animal Model for Testing Potentially Therapeutic Drugs.

Ongoing and future studies involve using mouse xenografts. This will permit confirmation of SMARCA4's tumor suppressor activity in vivo as well as to explore potential therapies. A preliminary xenografting study has been conducted using 293T cells depleted of SMARCA4 (FIG. 12A). Briefly, 5-6 weeks old athymic females were and will be used with n=5 for each experimental group. Five million cells were and will be subcutaneously injected in both the left and right flank. Tumor growth was and will be monitored over the course of a couple of weeks. Preliminary data (FIGS. 12A and 12B.) confirm that depletion of SMARCA4 in 293T cells leads to more aggressive growth in mice, further supporting previously adduced data that SMARCA4 is a tumor suppressor. These studies will be expanded using more cell lines that we plan to deplete of SMARCA4 as described above.

Similarly, xenografting will be used to explore potential therapies. Several drugs could be promising for targeting SMARCA4 mutant tumors, such as EZH2 inhibitors and drugs that target DNA damage repair pathways. EZH2 hyperactivity has been explored as a therapeutic target and several EZH2 inhibitors have been tested in preclinical and clinical studies. Given that SMARCA4 and EZH2 have an antagonistic relationship, and it has been suggested that SMARCA4 depletion can cause EZH2 hyperactivity, we anticipate that SMARCA4-depleted tumors will be sensitive to EZH2 inhibitors. In our initial studies, we will use the EZH2 inhibitors GSK126, EPZ-6438 and GSK343. We will also explore the sensitivity of SMARCA4 depleted cells to DNA damage repair targeting drugs. The most recent studies suggest SMARCA4's role in DNA damage repair pathways. Depletion of SMARCA4 would render cells sensitive to the DNA damage repair pathway targeting drugs, such as PARP inhibitors (e.g. BSI 201 or BMN 673 by way of nonlimiting example).

Exemplary PARP inhibitor compounds are disclosed below:

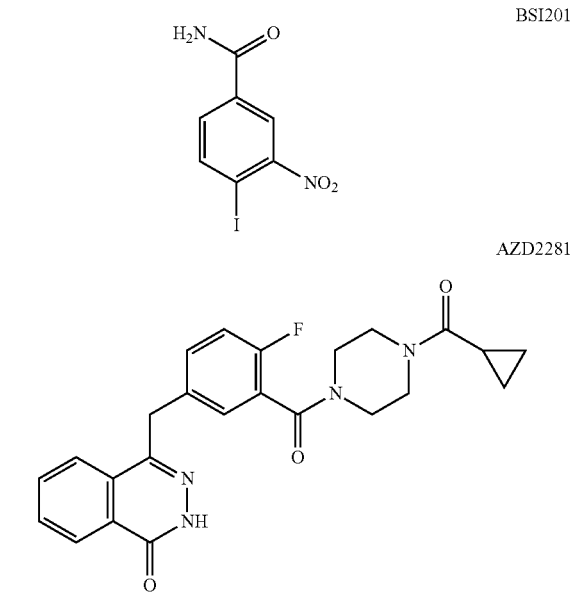

Preliminary data in SMARCA4-null SCCOHT cell line Bin67 confirm the sensitivity to the PARP inhibitor BMN-673 and camptothecin (CPT), a DNA damaging agent. This will be further tested in vivo using mouse xenografts. We anticipate that SMARCA4-depleted cells will be sensitive to drugs targeting DNA damage repair pathways as well as combinations of such drugs with more traditional chemotherapeutic drugs. In addition, combination therapies using EZH2 inhibitors and DNA repair drugs or conventional chemotherapeutics can thus be tested.

All mouse xenografting will be performed as described above. Initially, we will use 293T cells that are either WT or SMARCA4-depleted. Drug administration will be performed according to manufacturers' directions. For those drugs that are not already tested in mice, we will perform dose-escalation studies to test for drug toxicity. The drugs that specifically kill SMARCA4-depleted cells will be used in future studies.

TABLE 3

Sequences Listed

| Sequence ID Number | GenBank ID Match |
| --- | --- |
| SEQ ID NO: 1 | *Homo sapiens* SMARCA4 isoform 1 mRNA (GenBank EU430759.1) |
| SEQ ID NO: 2 | *Homo sapiens* SMARCA4 isoform 1 Protein (GenBank EU430759.1) |
| SEQ ID NO: 3 | *Homo sapiens* SMARCA4 isoform 2 mRNA (GenBank EU430757.1) |
| SEQ ID NO: 4 | *Homo sapiens* SMARCA4 isoform 2 Protein (GenBank EU430757.1) |
| SEQ ID NO: 5 | *Homo sapiens* SMARCA4 isoform 3 mRNA (EU430756.1) |
| SEQ ID NO: 6 | *Homo sapiens* SMARCA4 isoform 3 Protein (EU430756.1) |
| SEQ ID NO: 7 | *Homo sapiens* SMARCA4 isoform 4 mRNA (EU430758.1) |
| SEQ ID NO: 8 | *Homo sapiens* SMARCA4 isoform 4 Protein (EU430758.1) |

What is claimed is:

1. A method for treating ovarian cancer characterized by ovarian cancer cells having reduced or undetectable SMARCA4 protein levels and/or protein function in a subject in need thereof, the method comprising administering to the subject one or more EZH2 inhibitors, wherein the ovarian cancer cells are a small cell carcinoma of the ovary hypercalcemic type.

2. A method for treating a patient previously diagnosed with ovarian cancer that is associated with ovarian cancer cells exhibiting reduced or undetectable SMARCA4 protein levels and/or protein function, the method comprising administering to the patient one or more EZH2 inhibitors, wherein the ovarian cancer is small cell carcinoma of the ovary hypercalcemic type.

3. A method for diagnosing and treating small cell carcinoma of the ovary hypercalcemic type (SCCOHT) in a patient in need thereof, the method comprising:
   (i) detecting in an ovarian tumor sample from the patient one or more loss-of-function mutations in a SMARCA4 gene;
   (ii) diagnosing the patient with SCCOHT when the presence of the one or more loss-of-function mutations in a SMARCA4 gene is detected; and
   (iii) administering to the patient an effective amount of one or more EZH2 inhibitors.

* * * * *